US011071548B2

(12) United States Patent
Auld et al.

(10) Patent No.: US 11,071,548 B2
(45) Date of Patent: Jul. 27, 2021

(54) POWERED CIRCULAR STAPLER WITH RECIPROCATING DRIVE MEMBER TO PROVIDE INDEPENDENT STAPLING AND CUTTING OF TISSUE

(71) Applicant: ETHICON LLC, Guaynabo, PR (US)

(72) Inventors: Michael D. Auld, Blue Ash, OH (US); Brett E. Swensgard, West Chester, OH (US); Sol Posada, Cincinnati, OH (US); Michael J. Vendely, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 772 days.

(21) Appl. No.: 15/634,556

(22) Filed: Jun. 27, 2017

(65) Prior Publication Data

US 2018/0368851 A1  Dec. 27, 2018

(51) Int. Cl.
*A61B 17/115* (2006.01)
*A61B 17/00* (2006.01)
(Continued)

(52) U.S. Cl.
CPC .... *A61B 17/1155* (2013.01); *A61B 17/00234* (2013.01); *A61B 17/07207* (2013.01); *A61B 17/1114* (2013.01); *A61B 17/3476* (2013.01); *A61B 17/072* (2013.01); *A61B 90/98* (2016.02); *A61B 2017/00017* (2013.01); *A61B 2017/0046* (2013.01); *A61B 2017/00115* (2013.01);
(Continued)

(58) Field of Classification Search
CPC .............. A61B 17/072; A61B 17/1155; A61B 2017/00398; A61B 2017/07242; A61B 17/07207
See application file for complete search history.

(56) References Cited

U.S. PATENT DOCUMENTS 5,104,025 A * 4/1992 Main ..................... A61B 17/115
227/175.1
5,271,543 A * 12/1993 Grant ................... A61B 17/115
227/179.1
(Continued)

OTHER PUBLICATIONS

U.S. Appl. No. 15/634,385, filed Jun. 27, 2017.
(Continued)

*Primary Examiner* — Andrew M Tecco
*Assistant Examiner* — Nicholas E Igbokwe
(74) *Attorney, Agent, or Firm* — Frost Brown Todd LLC

(57) ABSTRACT

An apparatus includes a shaft assembly and an end effector. The shaft assembly includes an outer sheath and a staple driving mechanism. The end effector includes a staple deck, an anvil, a first staple driver, and a second staple driver. The staple deck defines a plurality of staple openings in at least one annular array. Each staple opening in the plurality of staple openings houses a staple. The anvil is configured to actuate relative to the staple deck to compress tissue between the staple deck and the anvil. The staple driving mechanism is configured to actuate the first staple driver to fire a first staple of the plurality of staples against the anvil. The staple driving mechanism is further configured to actuate the second staple driver independently of the first staple driver to fire a second staple of the plurality of staples against the anvil.

20 Claims, 65 Drawing Sheets

(51) Int. Cl.
*A61B 17/072* (2006.01)
*A61B 17/11* (2006.01)
*A61B 17/34* (2006.01)
*A61B 90/00* (2016.01)
*A61B 90/98* (2016.01)

(52) U.S. Cl.
CPC ............ *A61B 2017/00398* (2013.01); *A61B 2017/00464* (2013.01); *A61B 2017/00477* (2013.01); *A61B 2017/00734* (2013.01); *A61B 2017/07242* (2013.01); *A61B 2017/07264* (2013.01); *A61B 2017/07278* (2013.01); *A61B 2017/07285* (2013.01); *A61B 2017/1132* (2013.01); *A61B 2090/034* (2016.02); *A61B 2090/0808* (2016.02)

(56) References Cited

U.S. PATENT DOCUMENTS

| | | | |
|---|---|---|---|
| 5,314,436 A * | 5/1994 | Wilk | A61B 17/1114 227/179.1 |
| 6,716,233 B1 * | 4/2004 | Whitman | A61B 17/07207 606/219 |
| 6,783,524 B2 | 8/2004 | Anderson et al. | |
| 7,000,818 B2 | 2/2006 | Shelton, IV et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,430,292 B2 * | 4/2013 | Patel | A61B 17/1155 227/181.1 |
| 8,453,914 B2 | 6/2013 | Laurent et al. | |
| 8,556,918 B2 * | 10/2013 | Bauman | A61B 17/072 606/151 |
| 9,072,535 B2 | 7/2015 | Shelton, IV et al. | |
| 9,186,142 B2 | 11/2015 | Fanelli et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 2007/0027473 A1 * | 2/2007 | Vresh | A61B 17/1114 606/219 |
| 2007/0034667 A1 * | 2/2007 | Holsten | A61B 17/07207 227/176.1 |
| 2009/0120994 A1 * | 5/2009 | Murray | A61B 17/115 227/180.1 |
| 2014/0166727 A1 * | 6/2014 | Swayze | A61B 17/115 227/179.1 |
| 2014/0263541 A1 | 9/2014 | Leimbach et al. | |
| 2015/0127029 A1 * | 5/2015 | Raza | A61B 17/1155 606/153 |
| 2015/0209032 A1 * | 7/2015 | Olson | A61B 17/068 227/175.1 |
| 2015/0272575 A1 | 10/2015 | Leimbach et al. | |
| 2015/0280384 A1 * | 10/2015 | Leimbach | A61B 90/98 227/175.1 |
| 2017/0086823 A1 | 3/2017 | Leimbach et al. | |
| 2017/0281162 A1 * | 10/2017 | Shelton, IV | A61B 17/0686 |

OTHER PUBLICATIONS

U.S. Appl. No. 15/634,418, filed Jun. 27, 2017.
U.S. Appl. No. 15/634,436, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,589, filed Jun. 27, 2017.
U.S. Appl. No. 15/634,620, filed Jun. 27, 2017.
European Search Report and Written Opinion dated Oct. 19, 2018 for Application No. EP 181799271.1, 11 pgs.
International Search Report and Written Opinion dated Oct. 18, 2018 for Application No. PCT/US2018/039698, 13 pgs.

\* cited by examiner

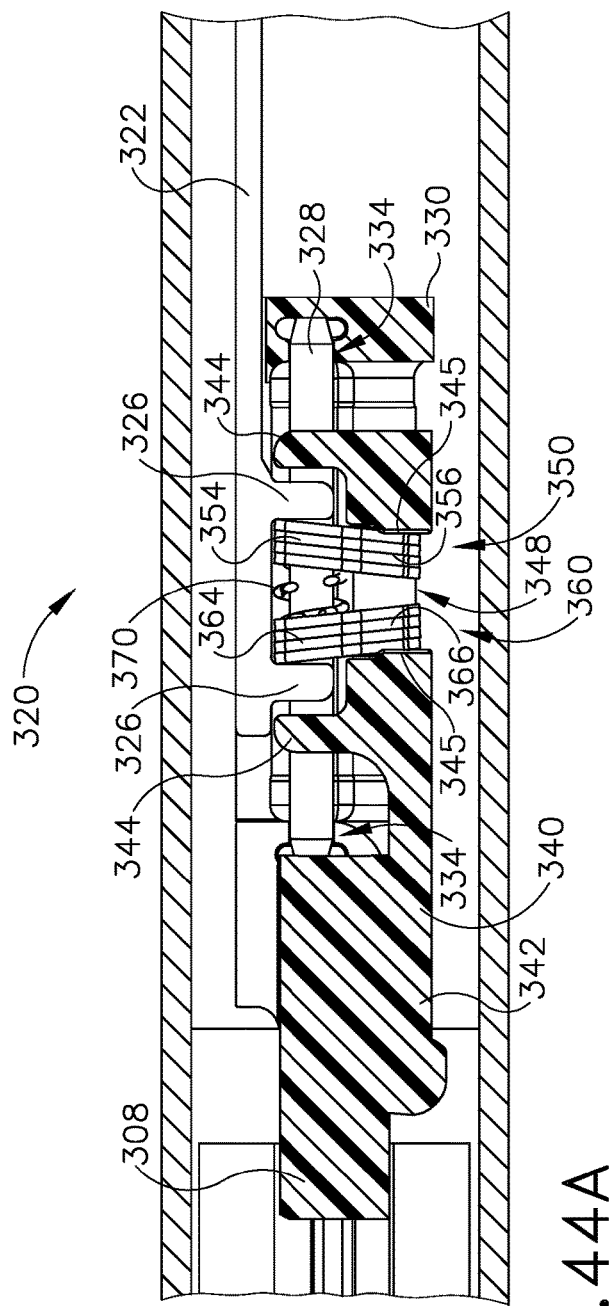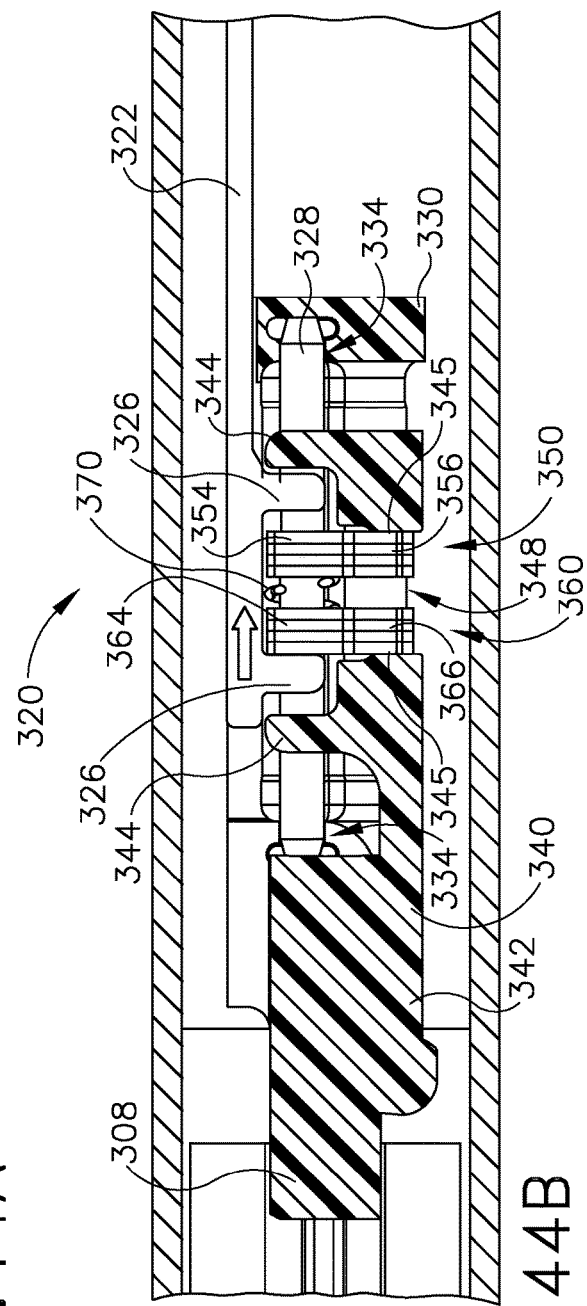

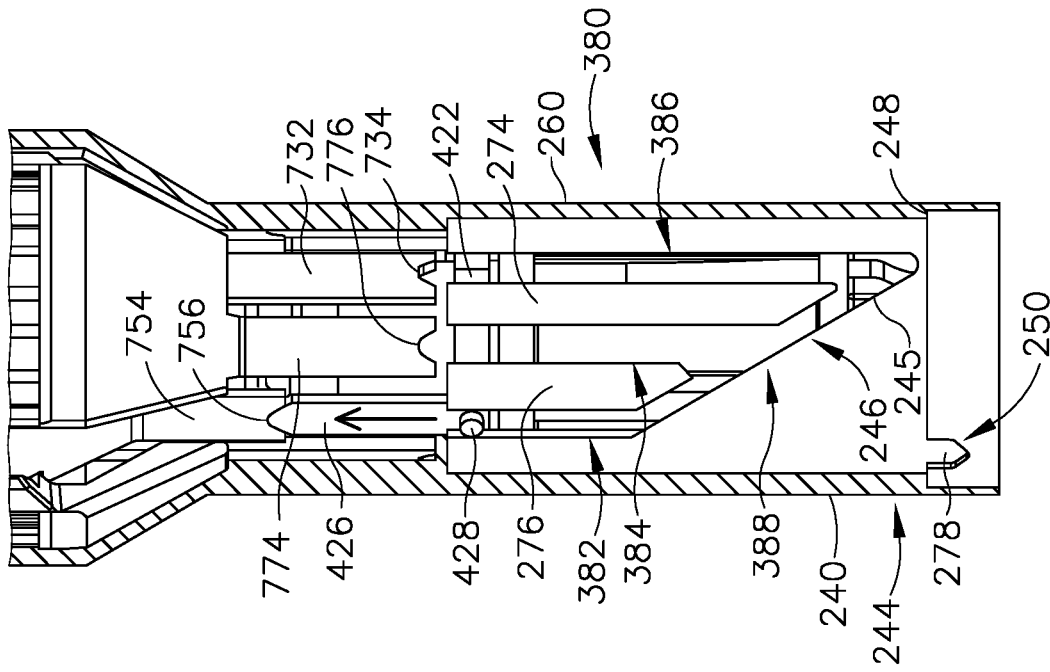
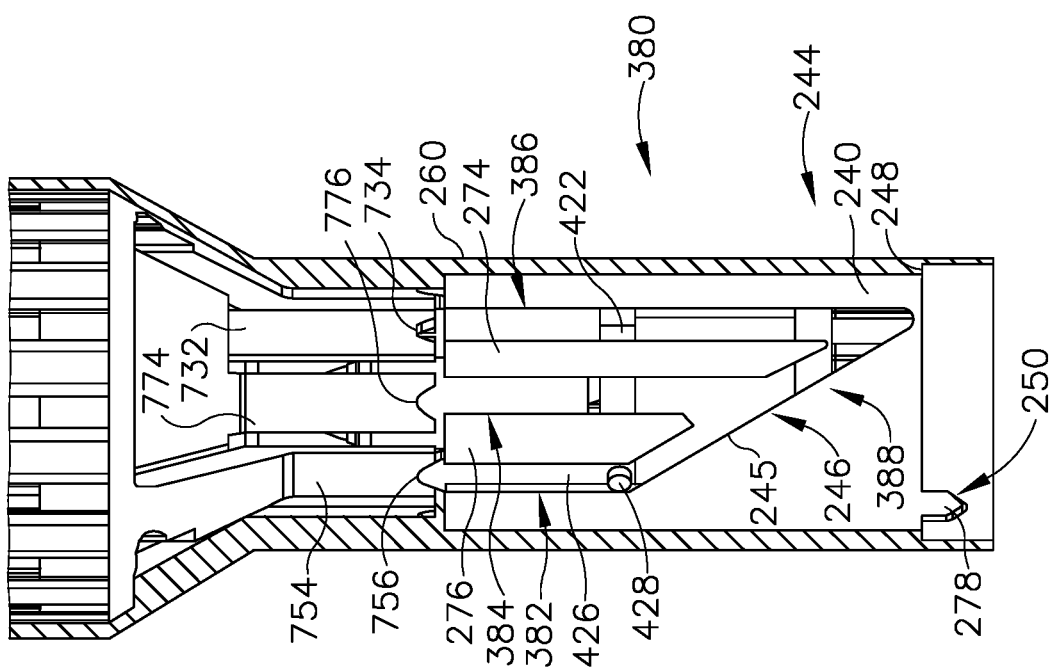
Fig.50A
Fig.50B

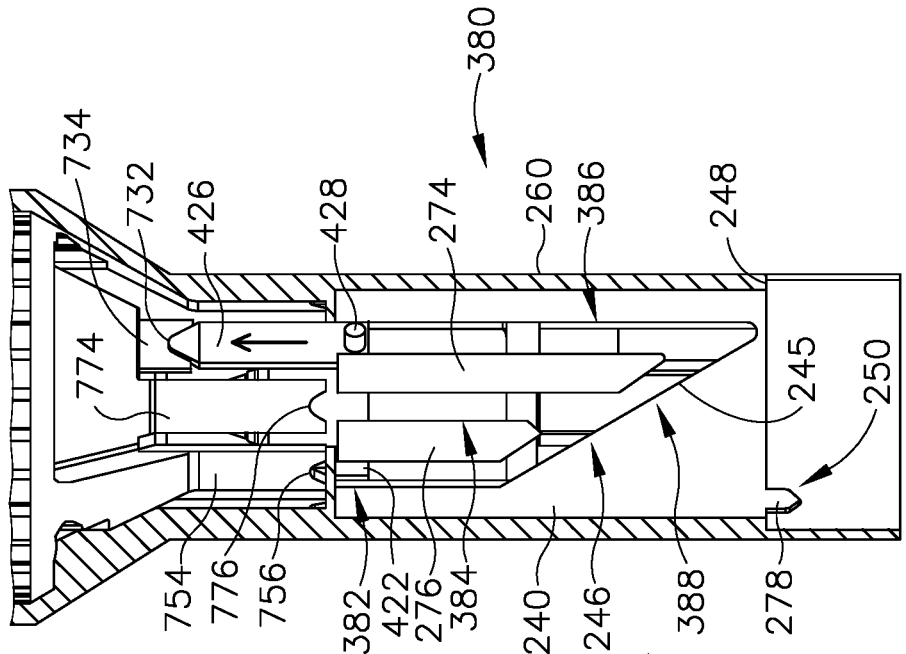
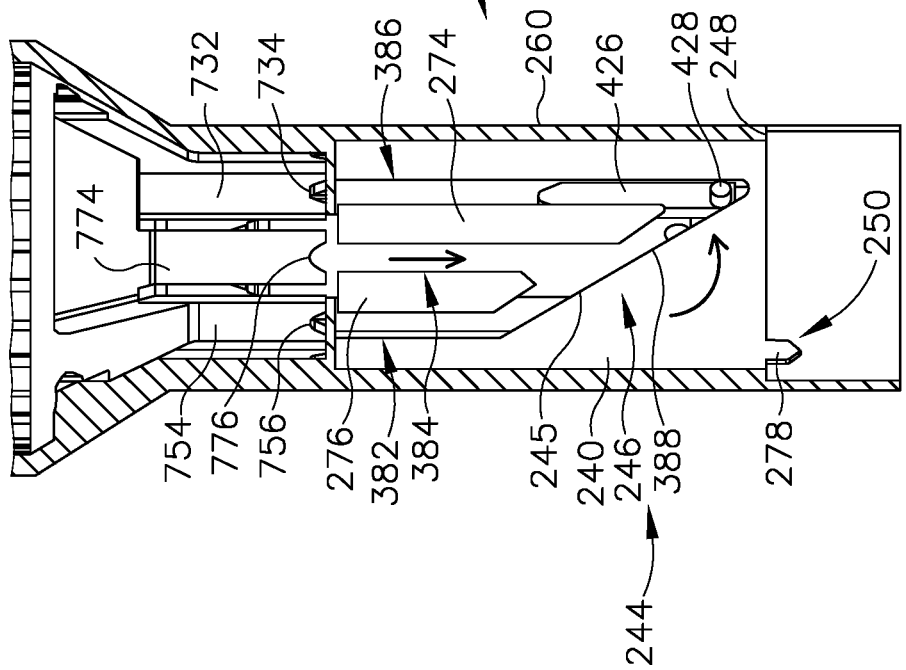

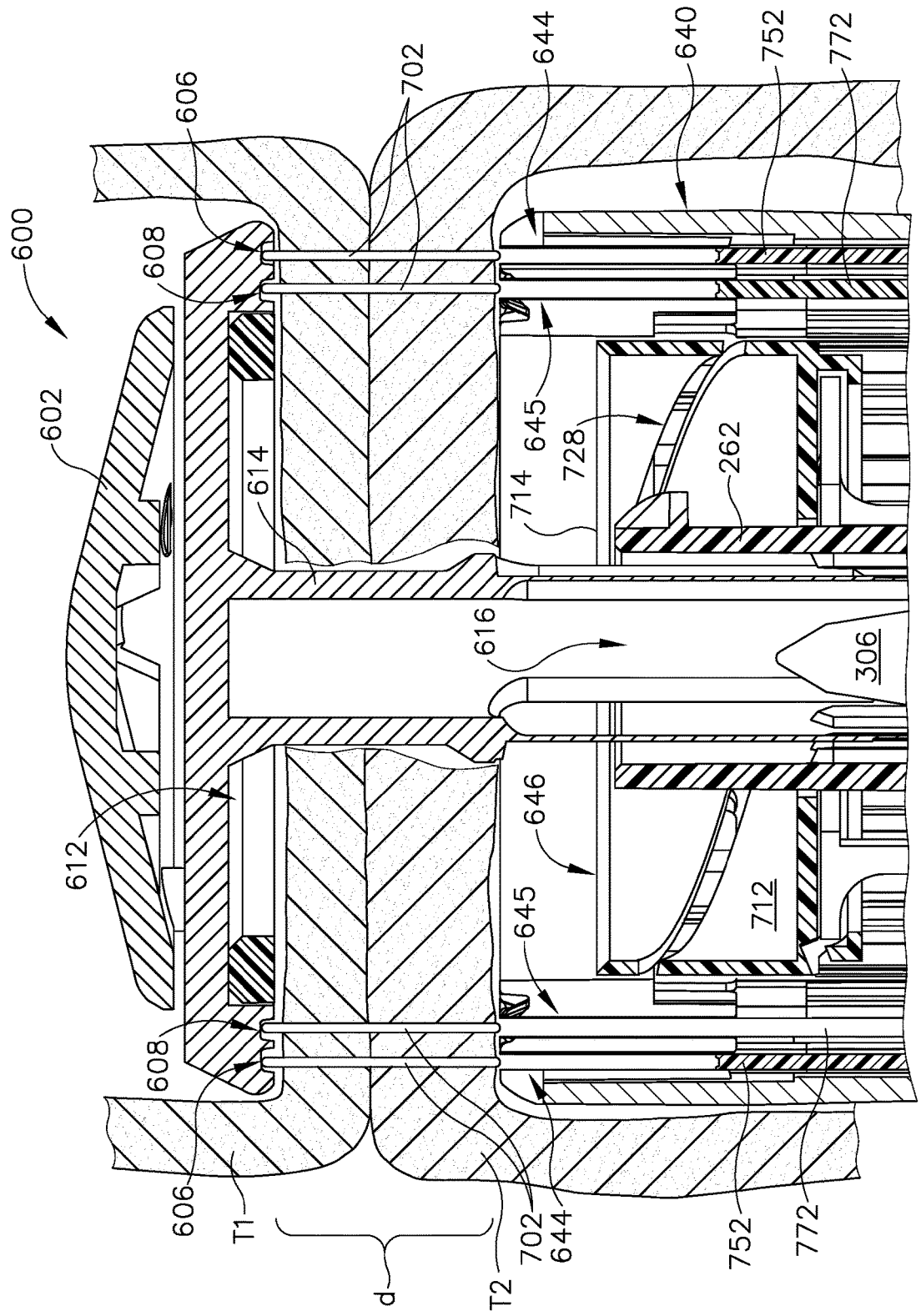

POWERED CIRCULAR STAPLER WITH RECIPROCATING DRIVE MEMBER TO PROVIDE INDEPENDENT STAPLING AND CUTTING OF TISSUE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 44A depicts a cross-sectional view of the longitudinal locking assembly of FIG. 38, taken along line 44-44 of FIG. 38, where the longitudinal locking assembly is in a locked configuration and the drive arm of FIG. 33 is in a first longitudinal position;

FIG. 44B depicts a cross-sectional view of the longitudinal locking assembly of FIG. 38, taken along line 44-44 of FIG. 38, where the longitudinal locking assembly is in an unlocked configuration and the drive arm of FIG. 33 is in a second longitudinal position;

FIG. 50A depicts an elevational side view of a portion of the shaft assembly of FIG. 11 and the end effector of FIG. 11, with certain portions omitted for clarity, where a driving member of the reciprocating drive assembly of FIG. 45 is in a first rotational position aligned with the outer staple driver of FIG. 17, where the outer staple driver is in a pre-fired position;

FIG. 50B depicts an elevational side view of a portion of the shaft assembly of FIG. 11 and the end effector of FIG. 11, with certain portions omitted for clarity, where the driving member of FIG. 50A is in the first rotational position aligned with the outer staple driver of FIG. 17, where the outer staple driver is in a fired position;

FIG. 50E depicts an elevational side view of a portion of the shaft assembly of FIG. 11 and the end effector of FIG. 11, with certain portions omitted for clarity, where the driving member of FIG. 50A is in a third rotational position aligned with the blade assembly of FIG. 20, where the blade assembly is in a pre-fired position;

FIG. 50F depicts an elevational side view of a portion of the shaft assembly of FIG. 11 and the end effector of FIG. 11, with certain portions omitted for clarity, where the driving member of FIG. 50A is in the third rotational position aligned with the blade assembly of FIG. 20, where the blade assembly is in a fired position;

FIG. 51E depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the inner staple driver assembly of FIG. 18 has driven staples through the first and second anatomical passageways to help form an anastomosis;

Figure 1:
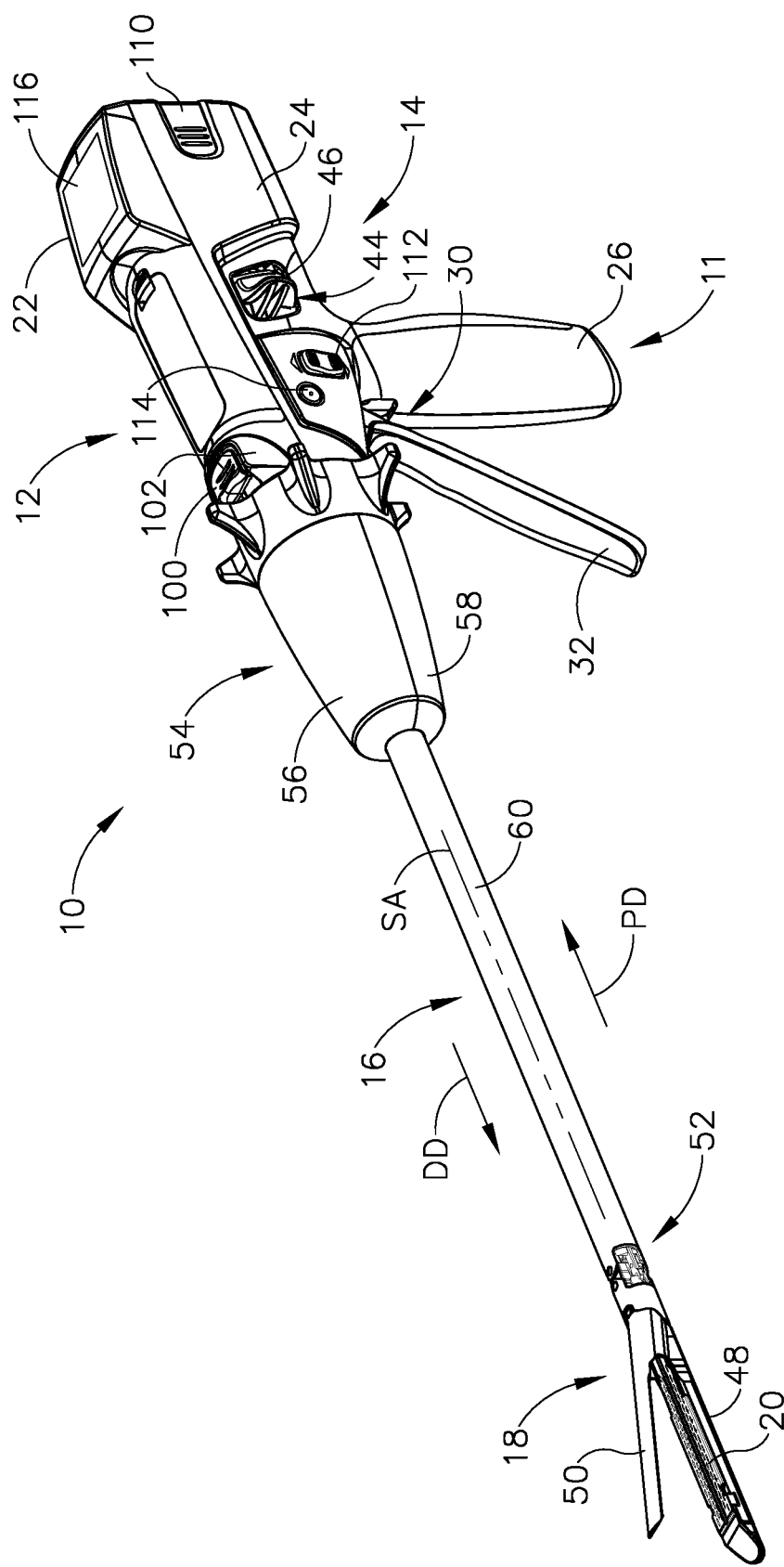
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though this is just one merely illustrative example.

Figure 2:
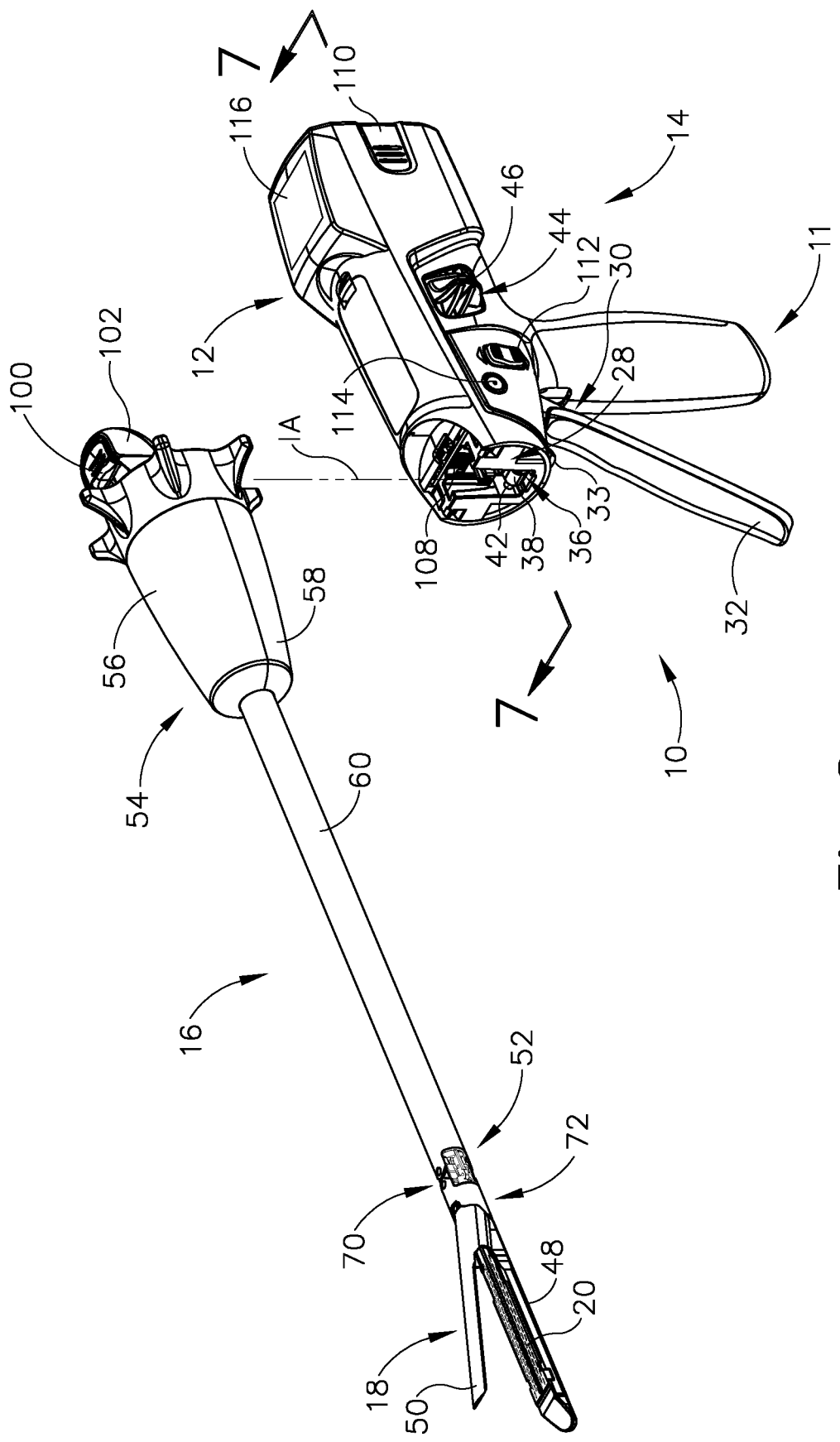
FIG. 2 depicts a perspective view of the instrument of FIG. 1, showing the shaft assembly disassembled from the handle assembly of the instrument.
Figure 3:
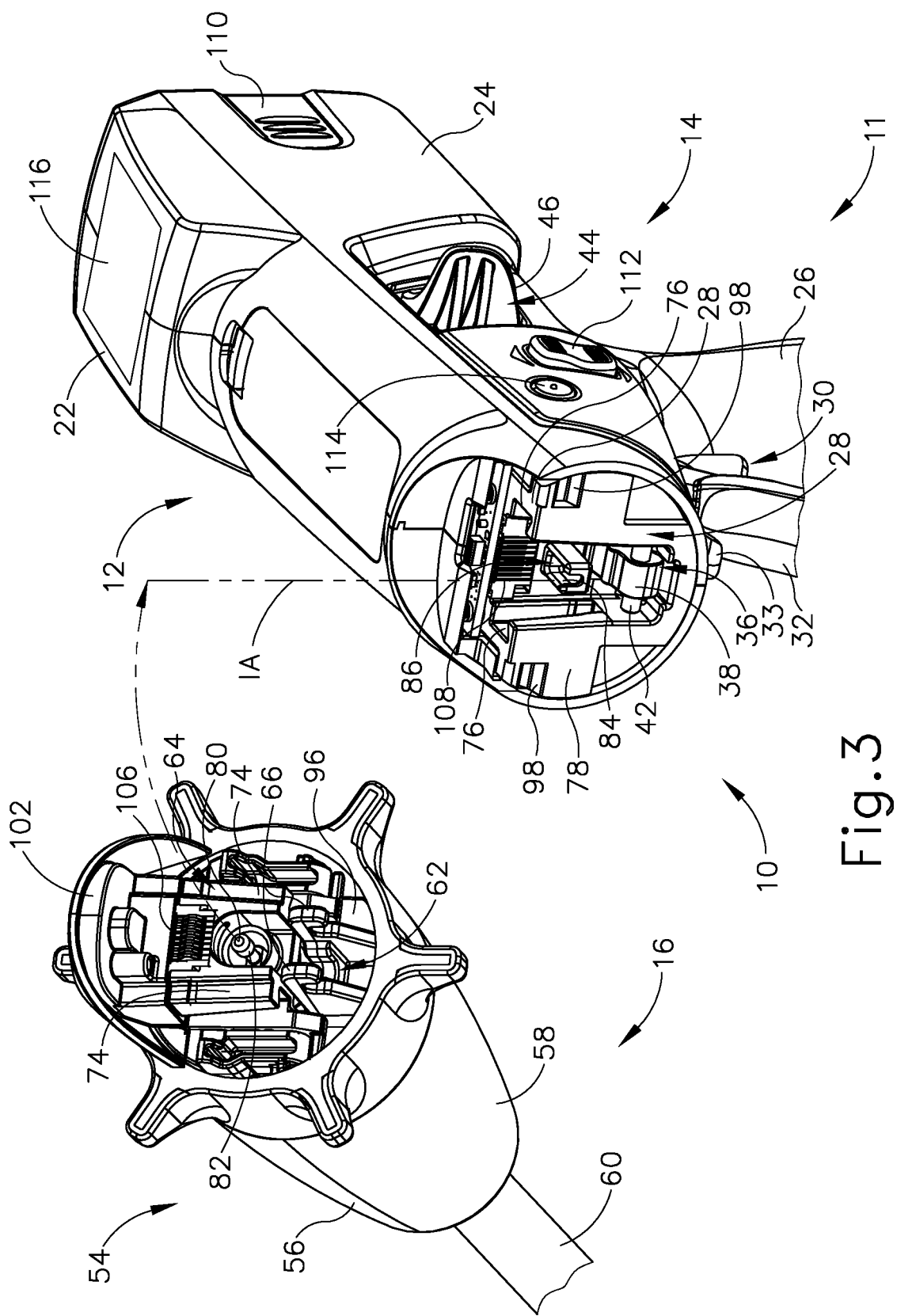
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
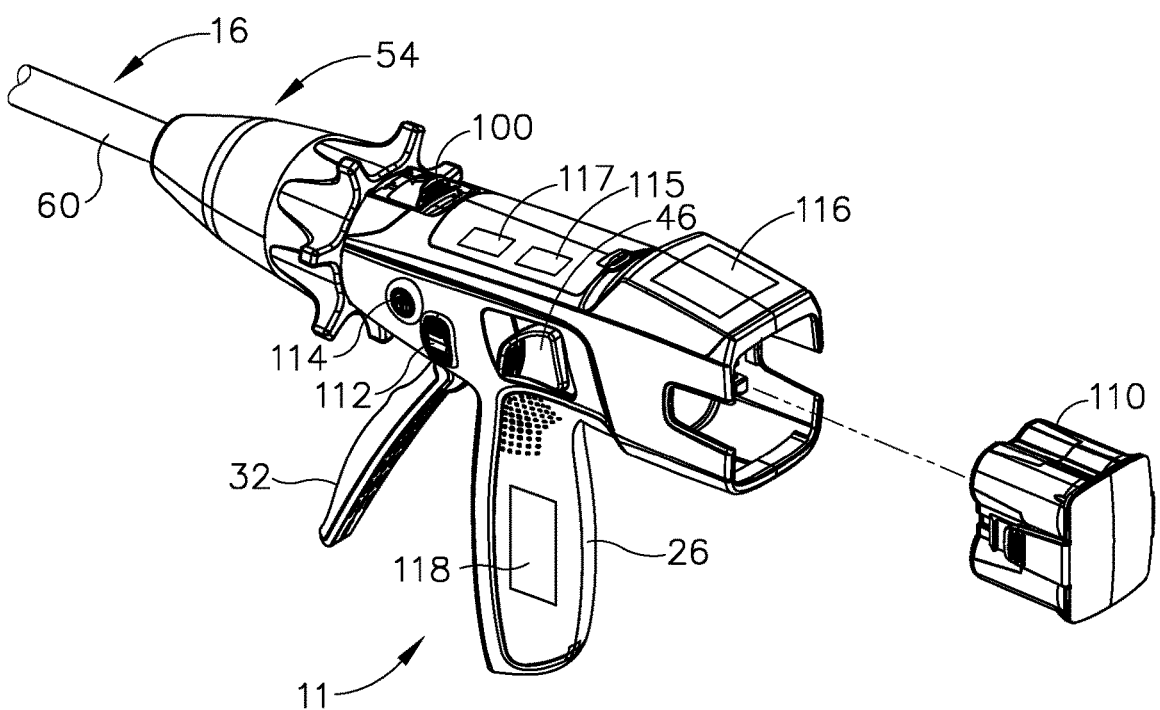
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

Figure 7:
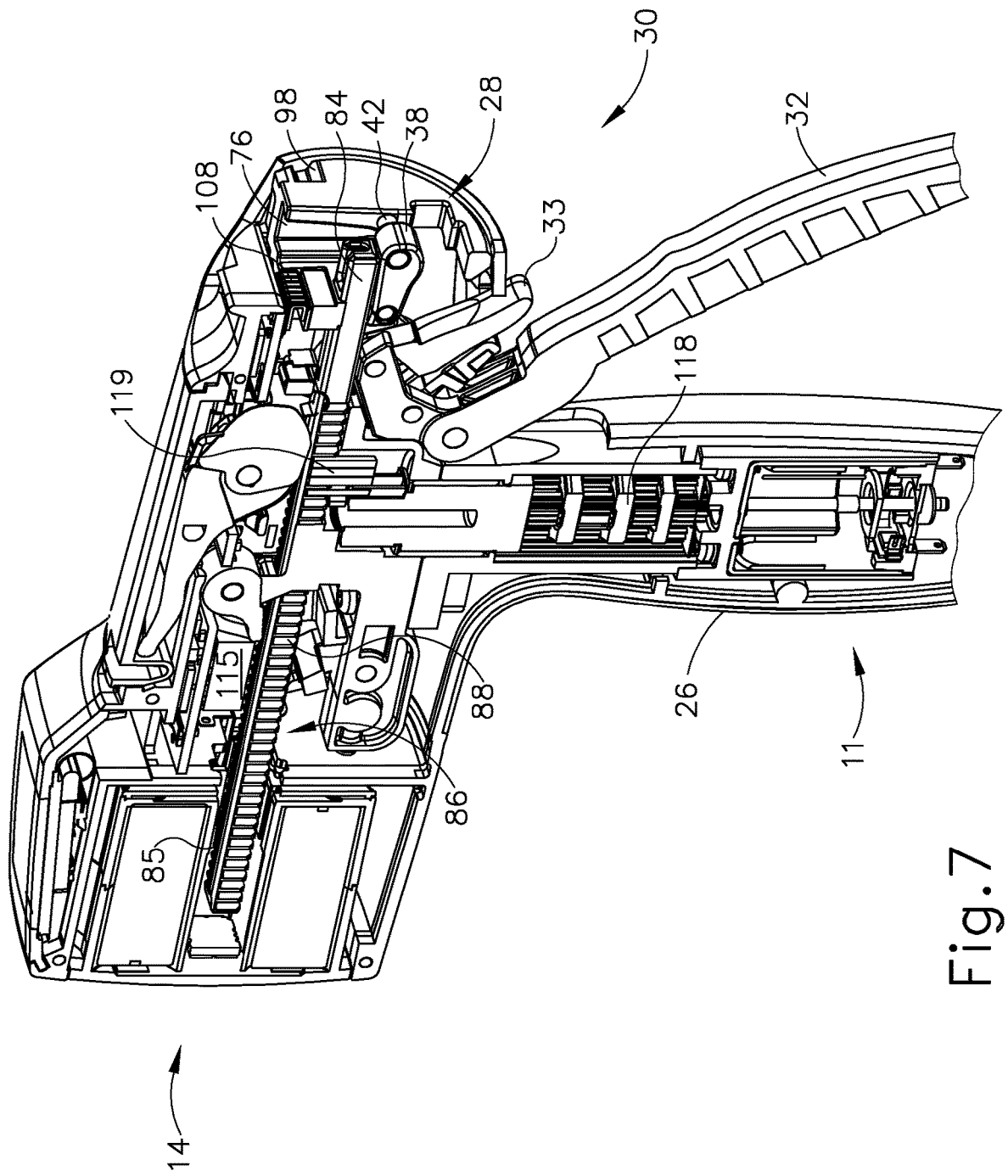
FIG. 7 depicts a cross-sectional view of the handle assembly of FIG. 1, taken along line 7-7 of FIG. 2.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). As also shown in FIG. 5 and FIG. 7, handle (14) includes an encoder (115) in communication with control circuit (117). Encoder (115) is configured to read a plurality of markings (85) located on longitudinal drive member (86). Each marking (85) is associated with a corresponding longitudinal position of longitudinal drive member (86). Additionally, as mentioned above, motor (118) is operable to actuate longitudinal drive member (86). For example, as motor (118) rotates, motor (118) may rotate an idler gear (119), which in turn may mesh with teeth (88) of longitudinal drive member (86), thereby actuating longitudinal drive member (86) in a linear direction. Therefore, as motor (118) actuates longitudinal drive member (86), encoder (115) may read markings (85) on longitudinal drive member (86) to track and determine the longitudinal position of longitudinal drive member (86). Encoder (115) may communicate this information to control circuit (117) to appropriately execute control algorithms.

While in the current example, encoder (115) and markings (85) are used to determine the longitudinal position of longitudinal drive member (86), any other suitable components may be used in order track and determine the longitudinal position of longitudinal drive member (86). By way of further example only, a stepper motor may be utilized to drive longitudinal drive member (86) in a manner that provides precise control of the longitudinal position of longitudinal drive member (86).

Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (H). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019 the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. Double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,264 on Feb. 12, 2019, The disclosure of which is incorporated by reference herein; and/or in accordance with the teachings of various other references cited herein.

Figure 4A:
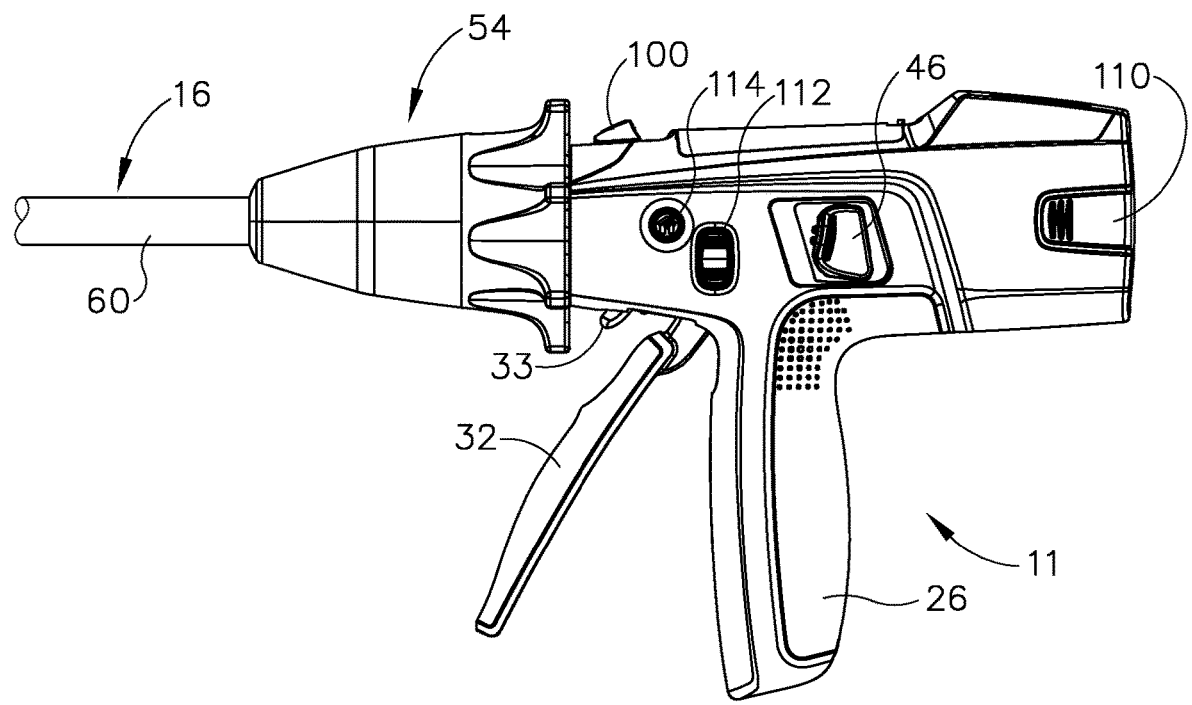
FIG. 4A depicts a side elevational view of a proximal portion of the instrument of FIG. 1, with a closure trigger in a first pivotal position and a firing trigger in a first pivotal position.
Figure 4B:
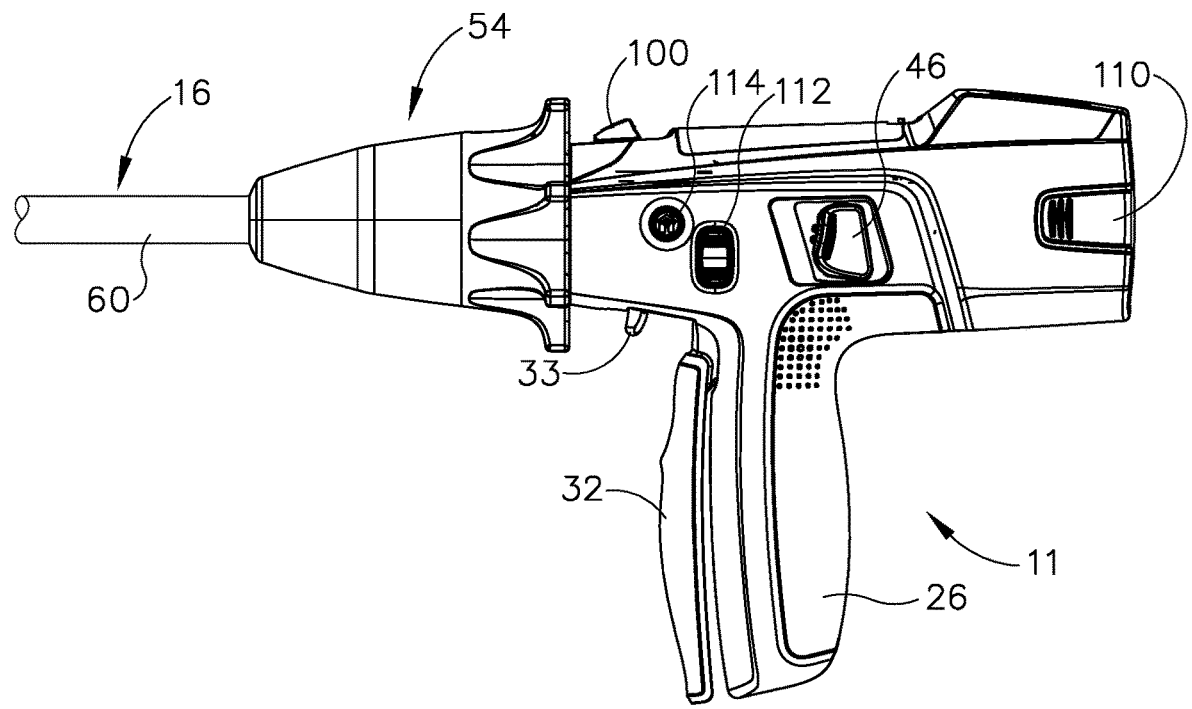
FIG. 4B depicts a side elevational view of a proximal portion of the instrument of FIG. 1, with the closure trigger in a second pivotal position and the firing trigger in a second pivotal position.
Figure 4C:
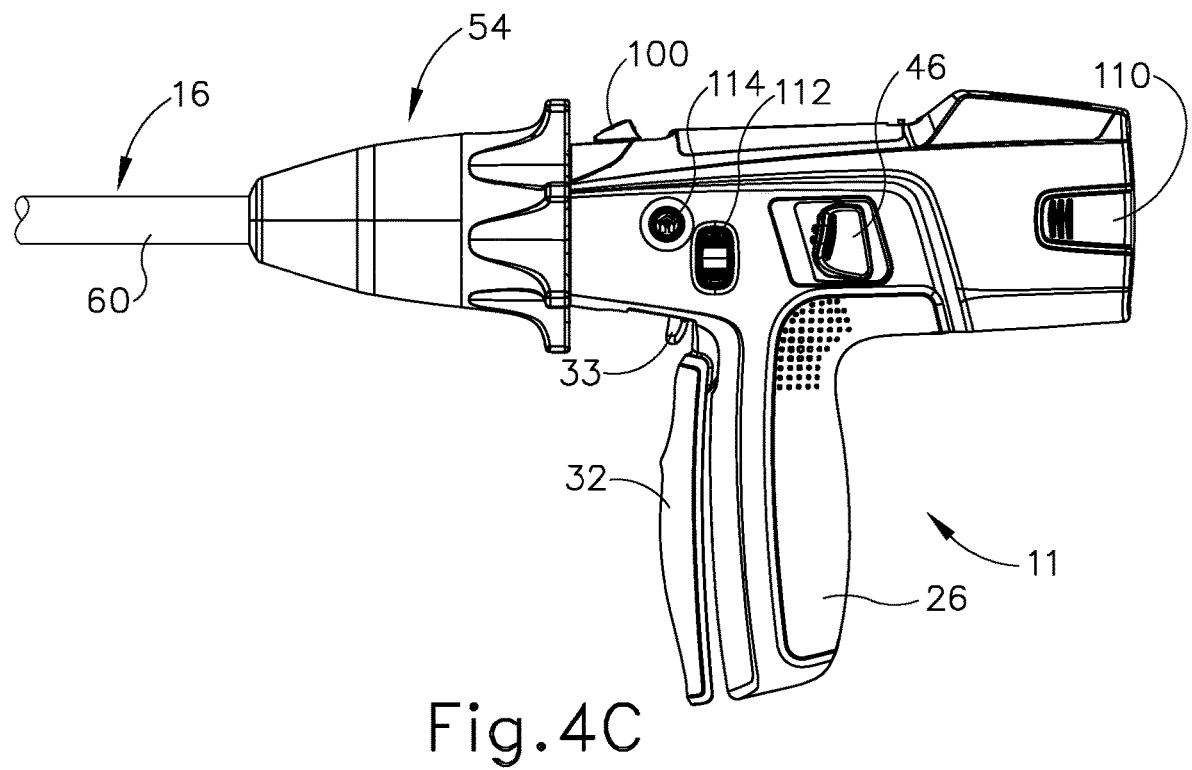
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). The presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364 on Feb. 12, 2019, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," filed Sep. 29, 2015, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
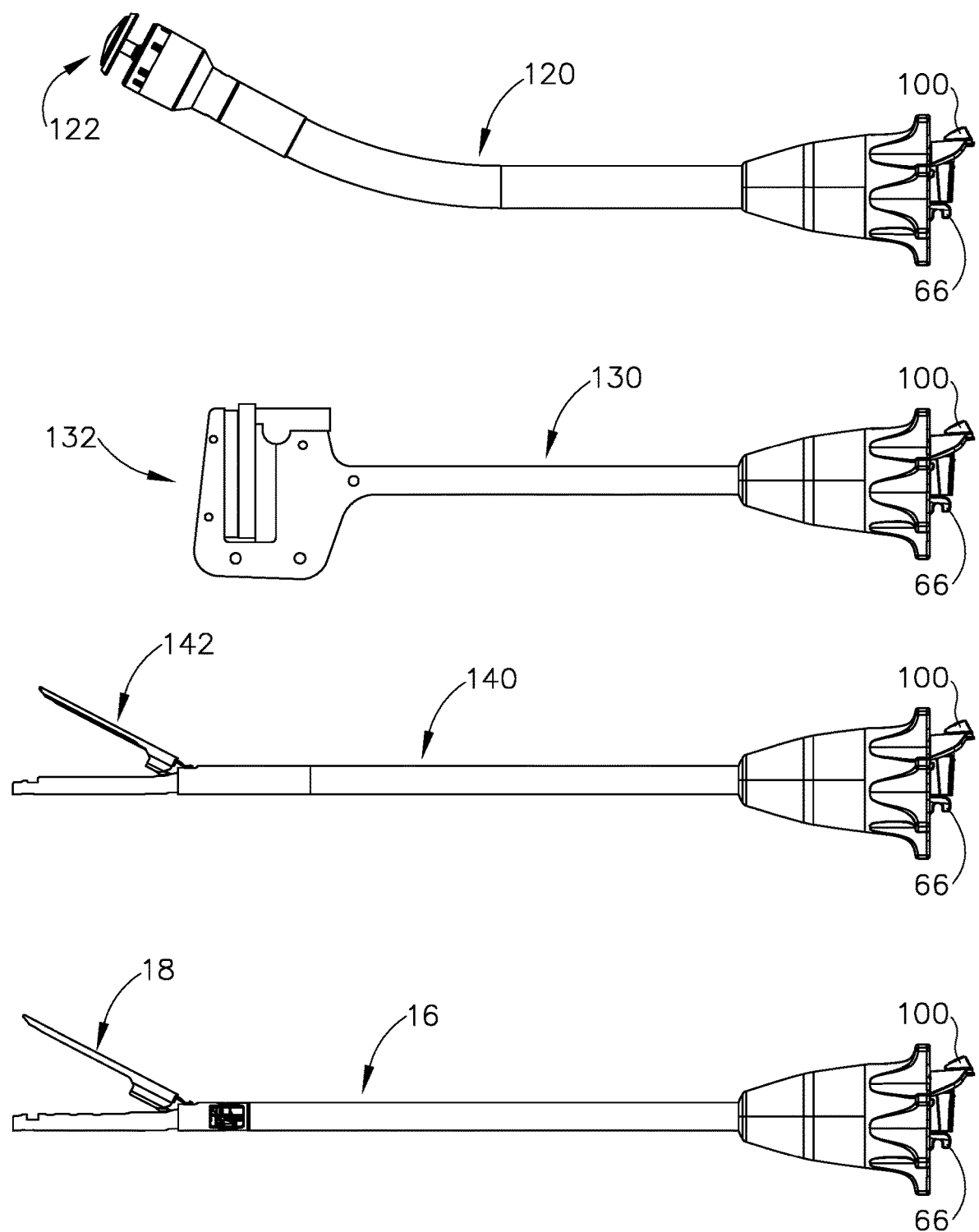
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). These various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642 on Mar. 13, 2018, the disclosure of which is incorporated by reference herein. In addition, or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued July 7, 2015, the disclosure of which is incorporated by reference herein.

II. Exemplary Circular Stapler Attachment with Independent Stapling and Cutting Features As described above, handle assembly (11) may be configured for use in connection with interchangeable shaft assemblies that include various end effectors, such as circular stapler shaft assembly (120) and end effector (122) to form an end-to-end anastomosis. For example, in some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis using a circular stapler similar to that of circular stapler shaft assembly (120) and end effector (122). The end-to-end anastomosis may provide a substantially unobstructed flow path from one portion of the digestive tract to the other portion of the digestive tract, without also providing any kind of leaking at the site of the anastomosis.

For instance, a circular stapler may be operable to clamp down on layers of tissue, drive staples through the clamped layers of tissue, and cut through the clamped layers of tissue to substantially seal the layers of tissue together near the severed ends of the tissue layers, thereby joining the two severed ends of the anatomical lumen together. In particular, the circular stapler may sever excess tissue that is interior to an annular array of staples at an anastomosis, to provide a substantially smooth transition between the anatomical lumen sections that are joined at the anastomosis.

In some instances, when using a circular stapler to form an end-to-end anastomosis, staple formation and anastomosis integrity may be inadvertently and negatively affected. It may therefore be desirable to reduce inadvertent and negative effects of staple formation during an end-to-end anastomosis. Additionally, it may be desirable to reduce to amount to tissue trauma caused during staple formation.

For example, staple formation may be negatively affected by initially driving an annular row of staples through tissue while simultaneously severing excess tissue. For instance, when an initial row of staples is forming simultaneously during excess tissue severing, stapled tissue may begin to move due to forces absorbed from severing of excess tissue before staples are fully formed. Movement of stapled tissue before full formation of an initial row of staples may adversely impact the quality of an end-to-end anastomosis. Therefore, it may be desirable to fire a first row of staples into tissue before severing excess tissue. Firing a first row of staples into tissue before severing tissue may prevent unwanted movement of stapled tissue before completion of staple formation, which may increase the integrity of staple formation in an end-to end anastomosis.

Additionally, staple formation may be negatively affected by simultaneously driving multiple annular staple rows to form an end-to-end anastomosis. Therefore, it may also be desirable to fire a first annular row of staples into tissue, then fire an additional annular row(s) of staples into tissue sequentially before severing excess tissue. Alternatively, it may be desirable to fire a first annular row of staples into tissue before severing excess tissue, then fire a second annular row of staples into tissue while simultaneously severing excess tissue. Firing a first row of staples into tissue may allow for the general shape of an end-to-end anastomosis for form, while sequentially firing a second row of staples into tissue may allow for a finer cinching of the end-to-end anastomosis to develop.

It may therefore be desirable to have a circular stapler with capabilities of independently firing annular rows of staples, and/or independently firing a blade assembly to sever excess tissue.

Figure 8:
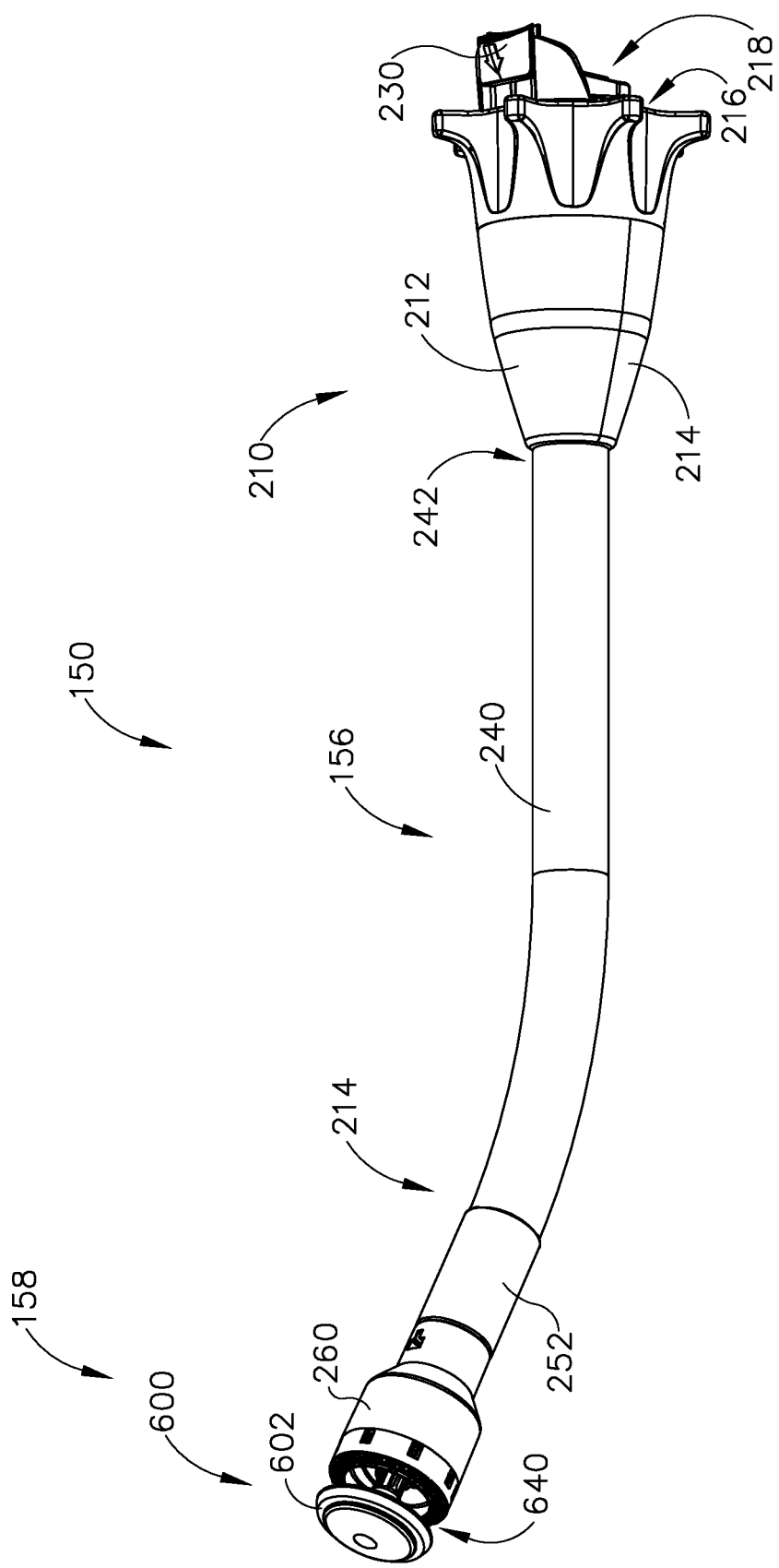
FIG. 8 depicts a perspective view of an interchangeable circular stapler shaft assembly that may be used with the handle assembly of FIG. 1 in replacement of the interchangeable shaft assembly of FIG. 1.
Figure 9:
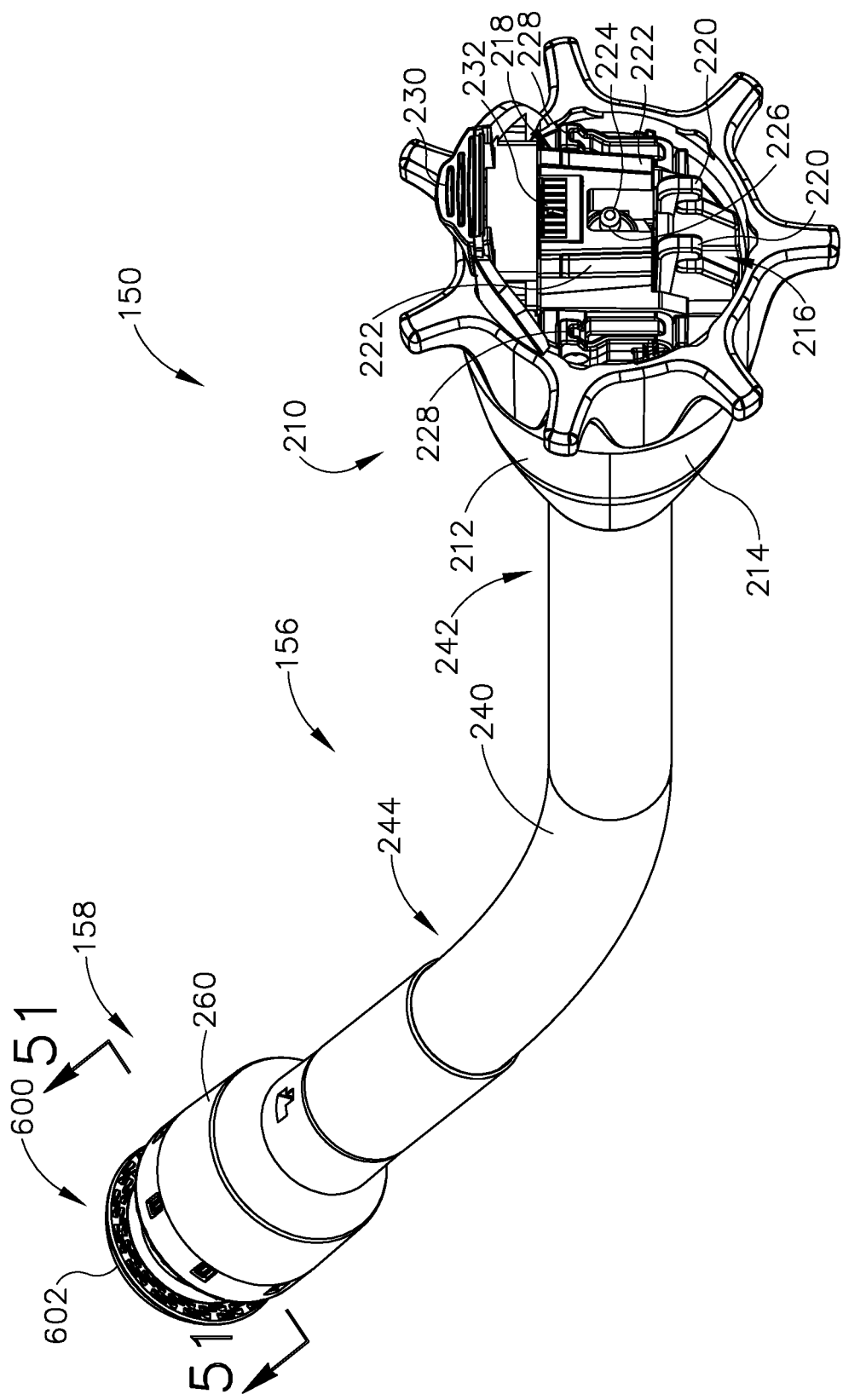
FIG. 9 depicts another perspective view of the interchangeable circular stapler shaft assembly of FIG. 8.

FIGS. 8-9 show an exemplary interchangeable circular stapler attachment (150) that may be readily incorporated with handle assembly (11) in place of shaft assembly (16) and end effector (18) described above. As will be described in greater detail below, handle assembly (11) and interchangeable circular stapler attachment (150) are configured to couple with each other such that circular stapler attachment (150) may perform an end-to-end anastomosis by independently driving multiple annular arrays of staple rows, as well as independently severing excess tissue after at least a first staple row is formed. In particular, first drive system (30) and longitudinal drive member (86) are configured to generate and apply various control motions to corresponding portions of interchangeable circular stapler attachment (150) in accordance with the descriptions above such that a clinician may selectively control portions of interchangeable circular stapler attachment (150) via handle assembly (11) to form an end-to-end anastomosis.

Interchangeable circular stapler attachment (150) includes a shaft assembly (156) and an end effector (158). Shaft assembly (156) includes a proximal housing (210), an outer sheath (240), a distal housing (260), an intermediate firing shaft (226), a reciprocating drive assembly (400) slidably housed within outer sheath (240) and distal housing (260), and a trocar assembly (300) slidably housed within reciprocating drive assembly (400). End effector (158) includes an anvil (600), a deck member (640) fixed to a distal end of distal housing (260), a plurality of staples (702) housed within deck member (640), and a stapling and cutting assembly (700) slidably housed within distal housing (260). As will be described in greater detail below, when properly coupled with handle assembly (11), trocar assembly (300) is configured to couple with anvil (600) and actuate anvil toward deck member (640) to compress two layers of tissue. As will also be described in greater detail below, reciprocating drive assembly (400) is configured to sequentially drive portions of stapling and cutting assembly (700) to drive multiple annular arrays of staples (702) into tissue and then sever excess portions of tissue to form an end-to-end anastomosis.

A. Exemplary End Effector

Figure 10:
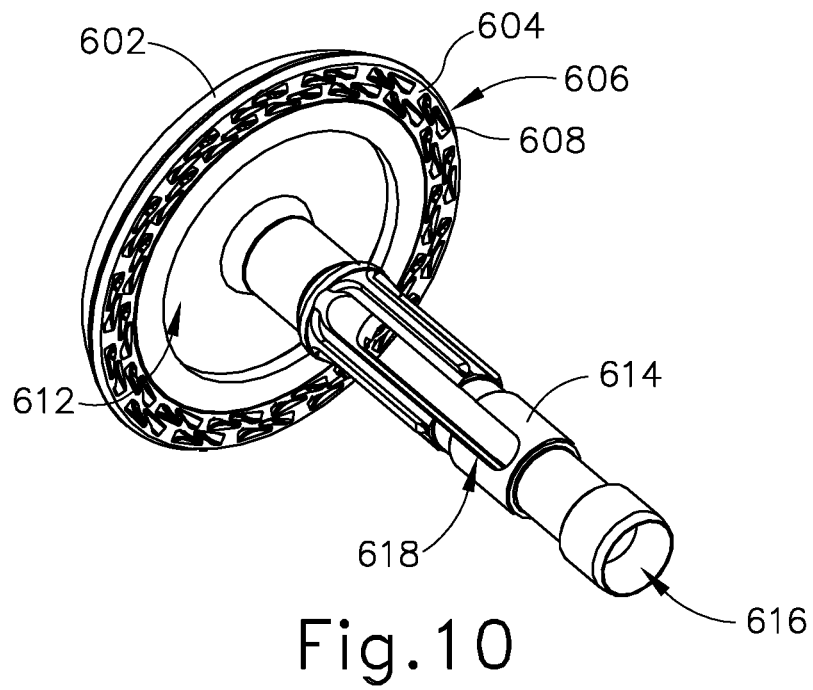
FIG. 10 depicts a perspective view of an anvil assembly of the interchangeable circular stapler shaft assembly of FIG. 8.

As noted above, end effector (158) includes anvil (600), deck member (640), and stapling and cutting assembly (700). As best seen in FIG. 10, anvil (600) of the present example comprises a head (602) and a shank (614). Head (602) includes a proximal surface (604) that defines an outer annular array of staple forming pockets (606) and an inner annular array of staple forming pockets (608). Staple forming pockets (606, 608) are configured to deform staples (702) as staples (702) are driven into staple forming pockets (606, 608). For instance, each stapling forming pocket (606, 608) may deform a generally "U" shaped staple (702) into a "B" shape as in known in the art. Proximal surface (604) terminates at an inner edge which defines an outer boundary for an annular recess (612) surrounding shank (614). As will be described in greater detail below, outer annular array of stapling forming pockets (606) are configured to receive staples (702) from a selected portion of stapling and cutting assembly (700) while inner annular array of staple forming pockets (608) are configured to receive staples (702) from a separate selected portion of stapling and cutting assembly (700).

Shank (614) defines a bore (616) and a pair of lateral openings (618). Bore (616) is open at a proximal end of shank (614) to receive a distal end of trocar assembly (300). Shank (614) is configured to selectively couple with the distal end of trocar assembly (300) such that when a portion of trocar assembly (300) is inserted within shank (614), anvil (600) may move with trocar assembly (300) relative to the rest of end effector (158) and shaft assembly (156). In other words, when properly coupled, trocar assembly (300) may drive anvil (600) toward and away from the rest of end effector (158) to compress and release tissue between proximal surface (604) and deck member (640). Shank (614) may include any suitable features for coupling anvil (600) with trocar assembly (300) as would be apparent to one having ordinary skill in the art in view of the teachings herein. For example, shank (614) may include a pair of latch members (not shown) positioned within bore (616) that deflect radially outwardly from the longitudinal axis defined by shank (616) to snap fit with trocar assembly (300).

Figure 13:
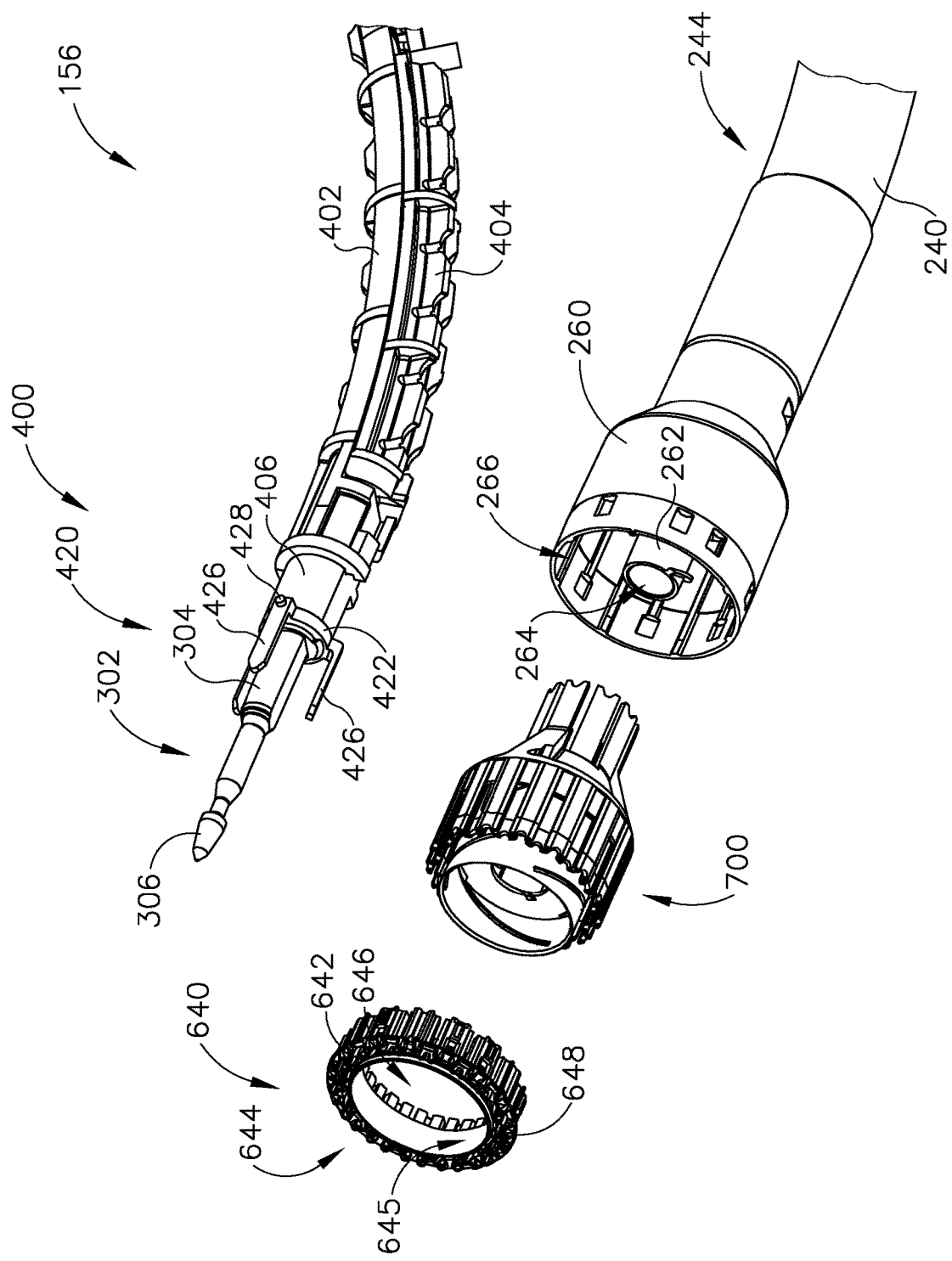
FIG. 13 depicts an exploded perspective view of the end effector of FIG. 11 and the distal end of the shaft assembly of FIG. 11.
Figure 14:
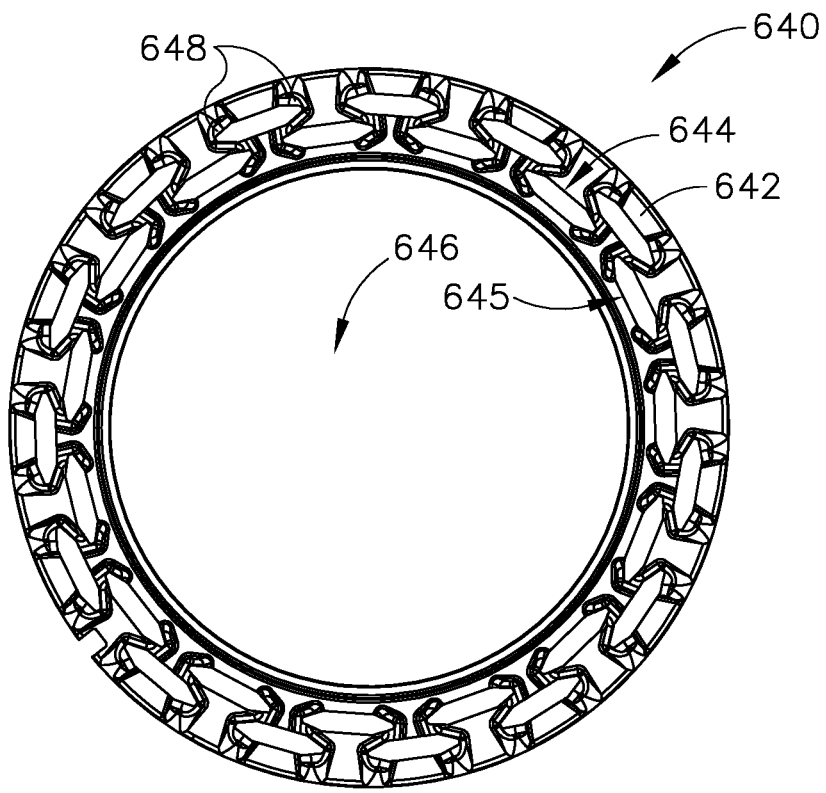
FIG. 14 depicts a top plan view of a deck member of the end effector of FIG. 11.
Figure 15:
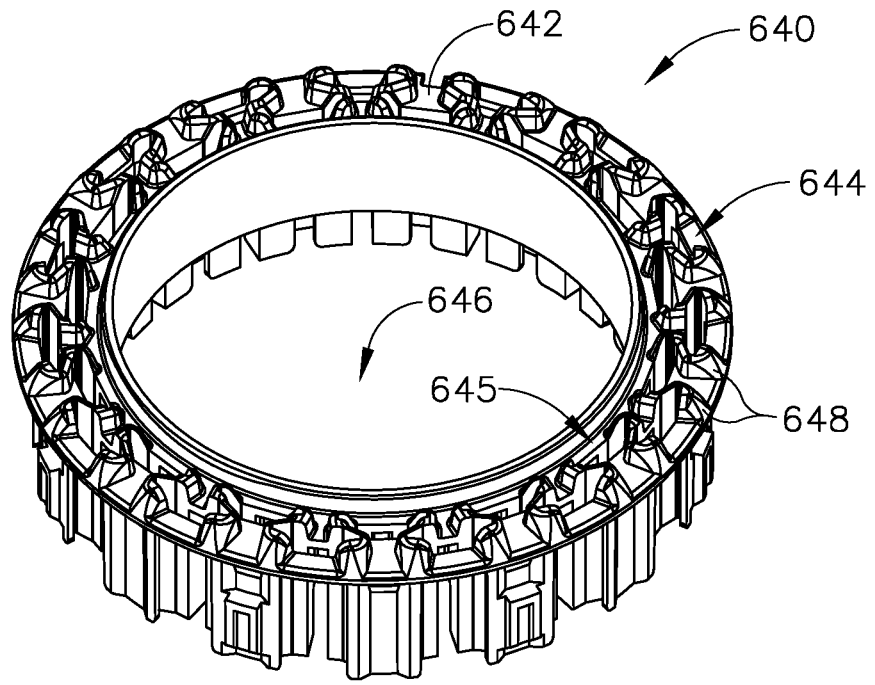
FIG. 15 depicts a perspective view of the deck member of FIG. 14.

As best seen in FIGS. 13-15, deck member (640) includes a distally presented deck surface (642) and a plurality of tissue grasping protrusions (648). Deck member (640) also defines an inner diameter (646), an outer concentric annular array of staple openings (606), and an inner concentric annular array of stapling openings (645). Deck member (640) is fixed to the distal end of distal housing (260). Additionally, deck member (640) houses a plurality of staples (702) in both staple openings (644, 645). Staple openings (644, 645) are configured to align with staple forming pockets (606, 608) respectively when anvil (600) and deck member (640) compress tissue between proximal surface (604) and distally presented deck surface (642). As will be described in greater detail below, staple openings (644, 645) are configured to receive respective portions of staple and cutting assembly (700) to drive staples (702) into respective staple forming pockets (606, 608).

Figure 11:
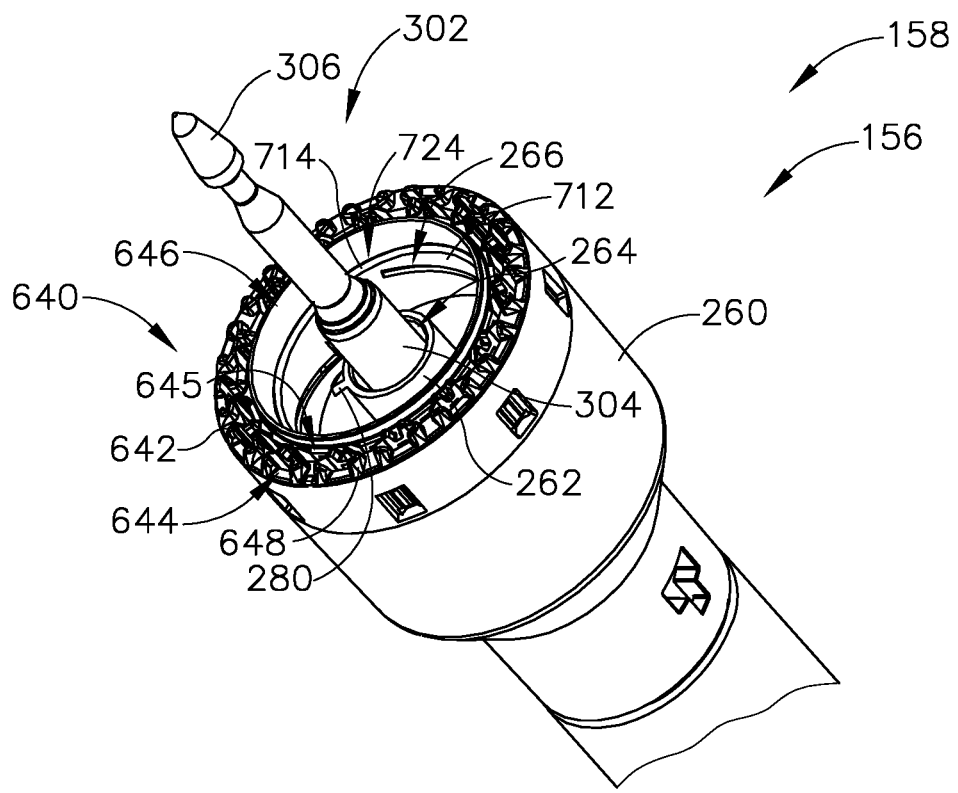
FIG. 11 depicts a perspective view of the distal end of a shaft assembly and an end effector of the interchangeable circular stapler shaft assembly of FIG. 8.
Figure 12:
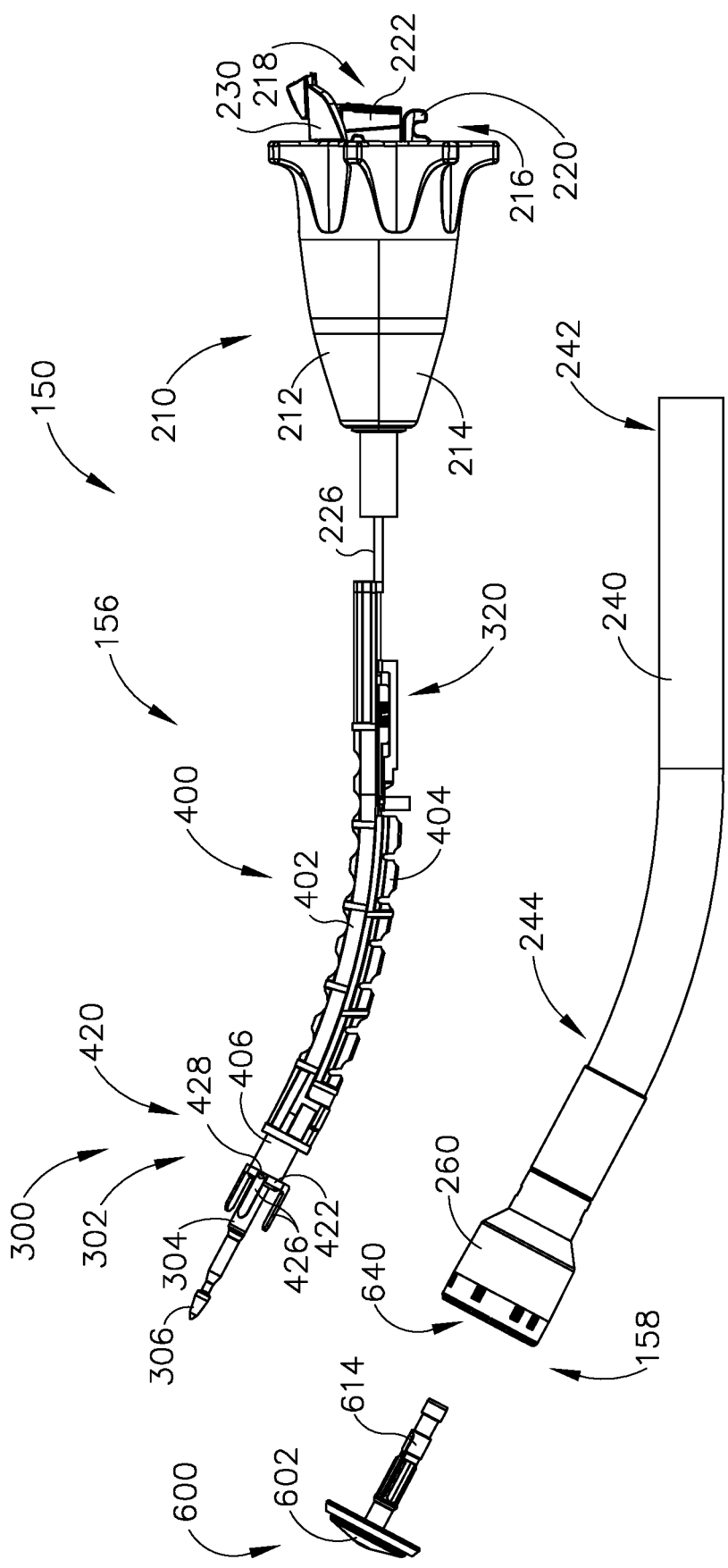
FIG. 12 depicts an exploded side view of the interchangeable circular stapler shaft assembly of FIG. 8.

As best seen in FIG. 11, and as will be described in greater detail below, inner diameter (646) is dimensioned to receive a blade member (712) of stapling and cutting assembly (700) such that blade member (712) may sever excess tissue within the confines of inner diameter (646). Additionally, inner diameter (646) may receive selected portions of trocar assembly (300) such that anvil (600) may couple with trocar assembly (300).

Figure 16:
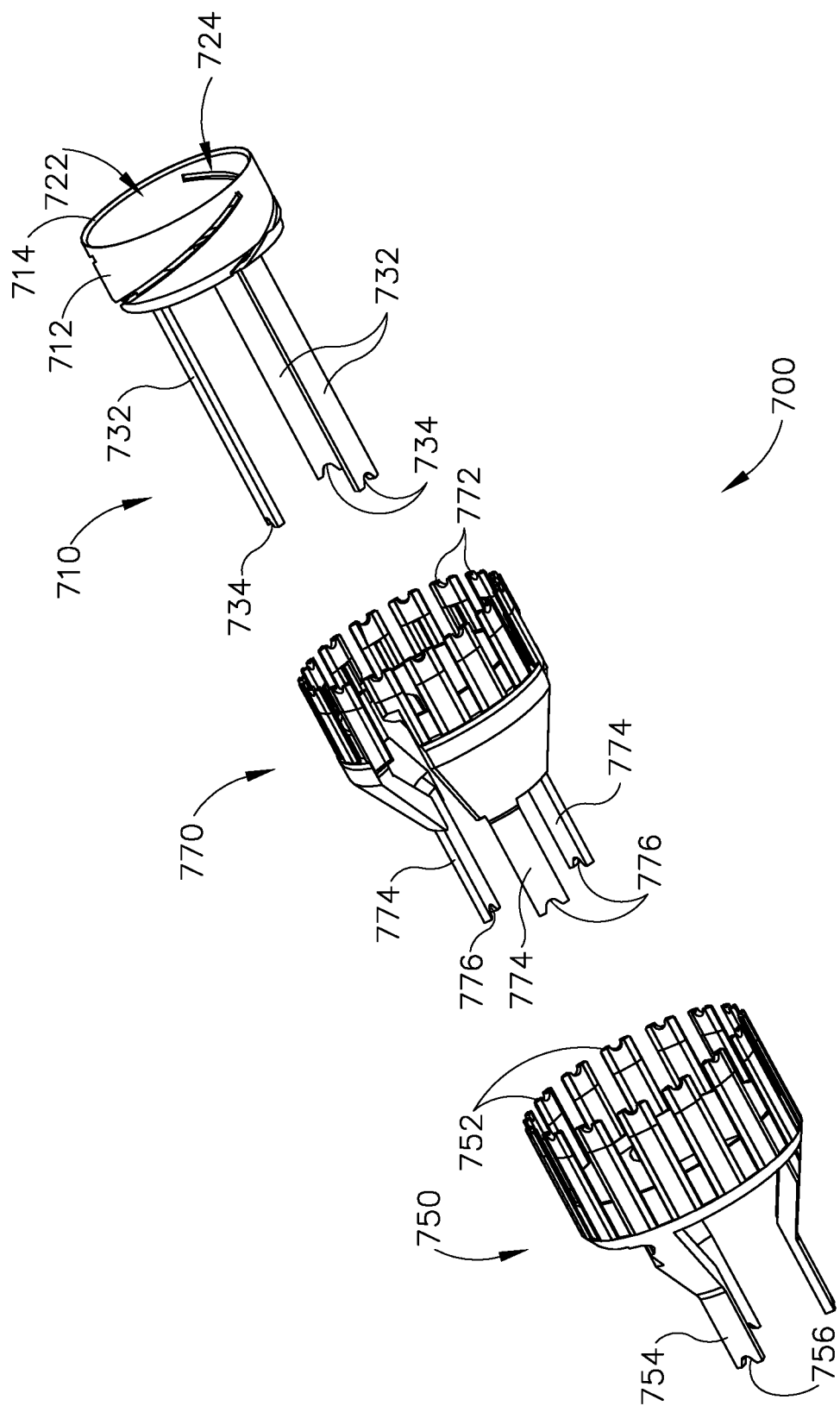
FIG. 16 depicts an exploded perspective view of a stapling and cutting assembly of the end effector of FIG. 11.

As best seen in FIG. 16, stapling and cutting assembly (700) include a blade assembly (710), an outer staple driver (750), and an inner staple driver assembly (770); all of which are slidably housed within distal housing (260) of shaft assembly (156). As will be described in greater detail below, blade assembly (710), outer staple driver (750), and inner staple driver assembly (770) are configured to be individually actuated relative to deck member (640) to either drive an annular array of staples (702) or to sever excess tissue.

Figure 17:
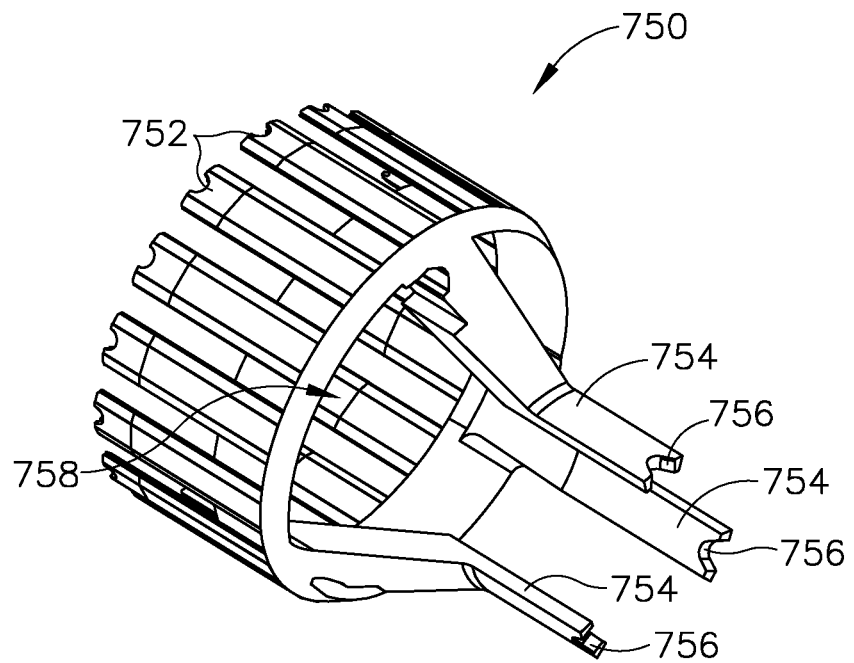
FIG. 17 depicts a perspective view of an outer staple driver of the stapling and cutting assembly of FIG. 16.

As best seen in FIG. 17, outer staple driver (750) includes an annular array of staple drivers (752), three proximally presented firing legs (754) each terminating into a drive coupler (756). Outer staple driver (750) defines a bore (758) dimensioned to slidably house inner staple driver assembly (770). Staple drivers (752) are each dimensioned to actuate within a respective staple opening of outer concentric annular array of staple openings (644) to drive staples (702) against a respective staple forming pocket from outer annular array of staple forming pockets (606). As will be described in greater detail below, proximally presented firing legs (754) and respective drive couplers (756) are positioned to selectively align with a portion of reciprocating drive assembly (400) such that staple drivers (752) may drive staples (702) independently of both blade assembly (710) and inner staple driver assembly (770).

Figure 18:
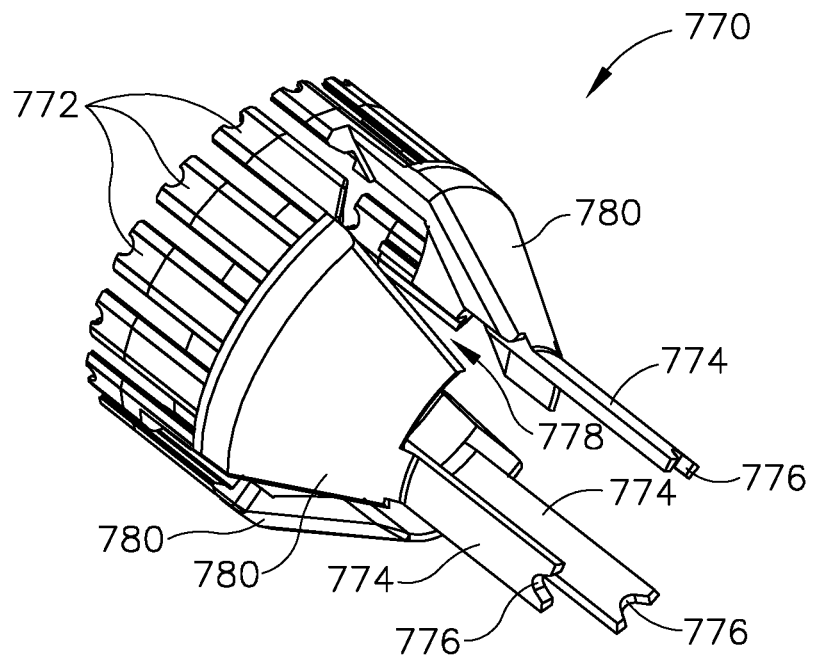
FIG. 18 depicts a perspective view of an inner staple driver assembly of the stapling and cutting assembly of FIG. 16.
Figure 19:
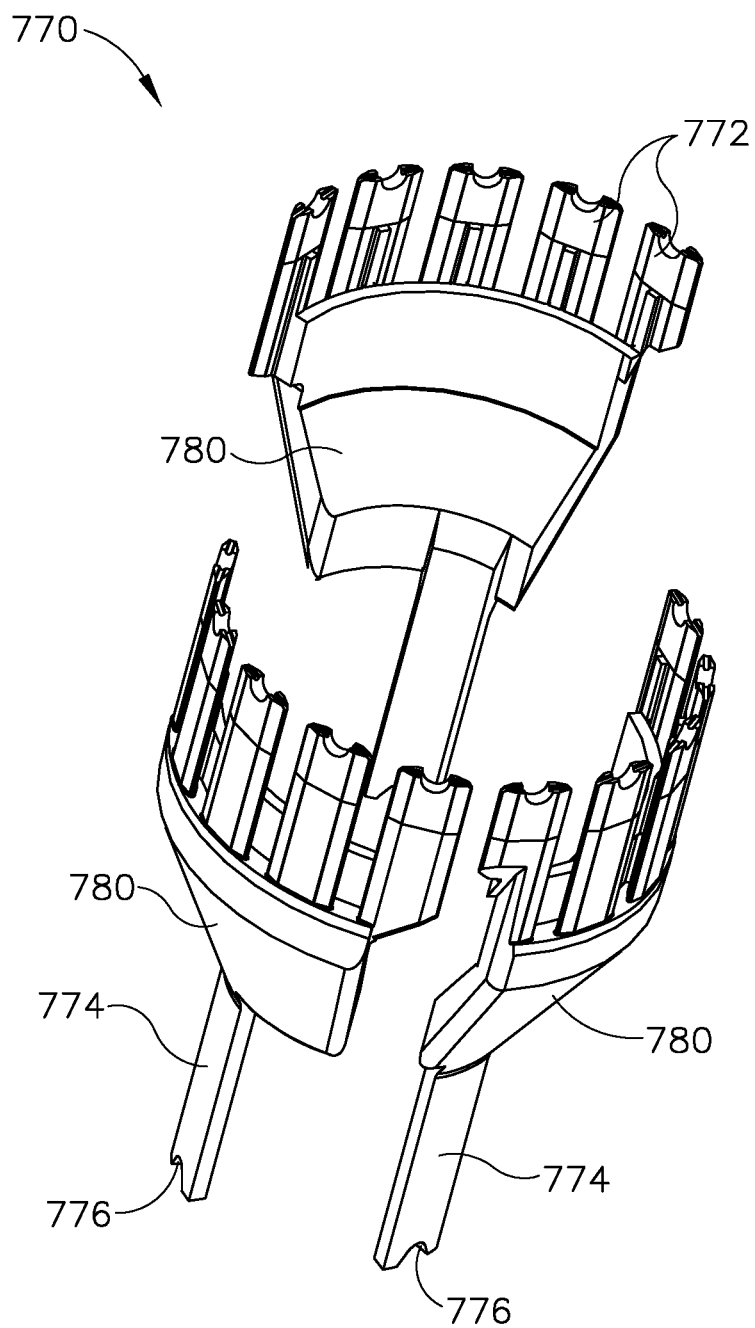
FIG. 19 depicts an exploded perspective view of the inner staple driver assembly of FIG. 18.

As best seen in FIGS. 18-19, inner staple driver assembly (770) includes a plurality of inner staple driver sections (780), each configured to be slidably housed between respective sectors defined by firing legs (754) of outer staple driver (750). Together, inner staple driver sections (780) define a bore (778) dimensioned to slidably house a blade member (712) of blade assembly (710). Each inner staple driver section (780) is located within the bore (758) of outer staple driver (750). Each inner staple driver section (780) includes a plurality of staple drivers (772) dimensioned to actuate within a respective staple opening of inner concentric annular array of staple openings (645) to drive staples (702) against inner annular array of staple forming pockets (608). Additionally, each inner staple driver section (780) includes a proximally presented firing leg (774) having a drive coupler (776). As will be described in greater detail below, proximally presented firing legs (754) and respective drive couplers (776) are positioned to selectively align with a portion of reciprocating drive assembly (400) such that staple drivers (772) of each inner staple driver section (780) may drive staples (702) independently of both blade assembly (710) and inner staple driver assembly (770).

Figure 20:
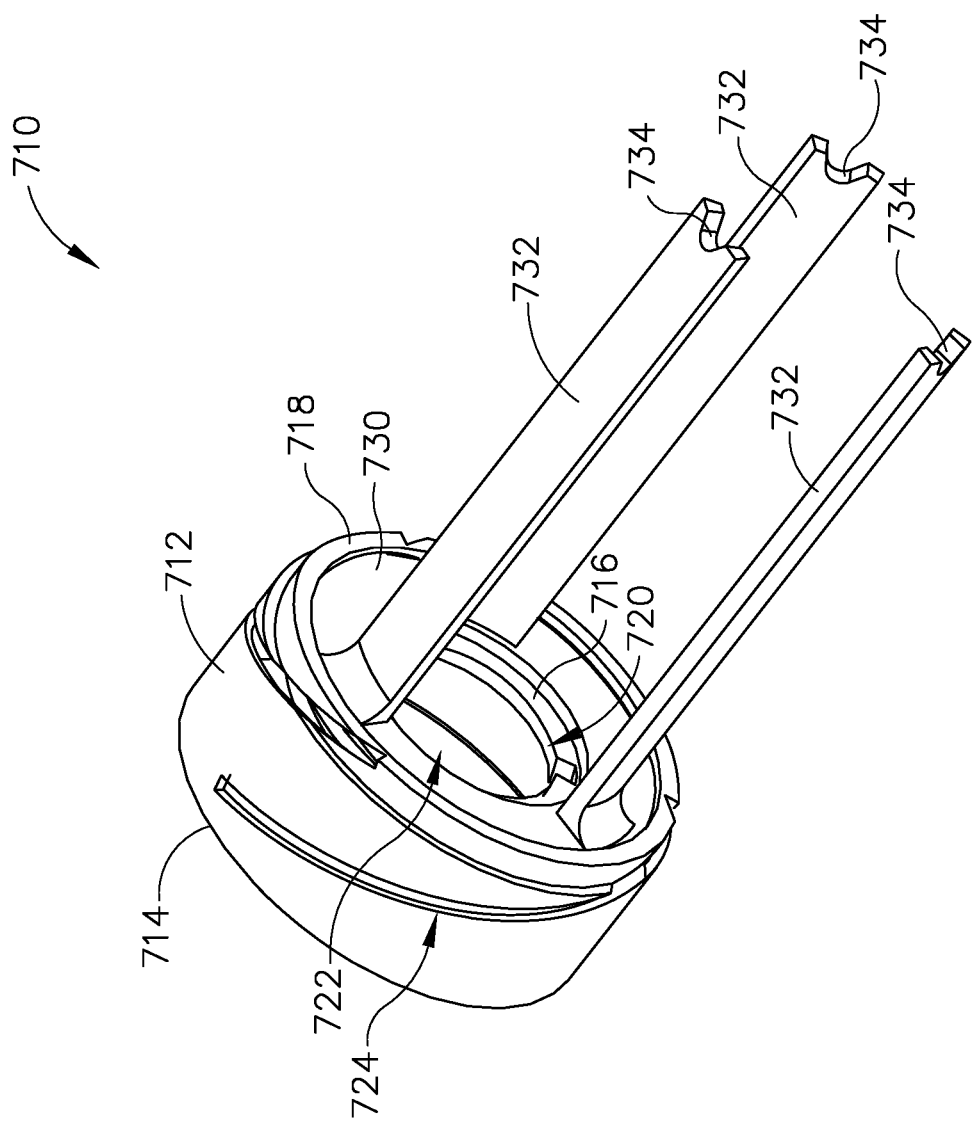
FIG. 20 depicts a perspective view of a blade assembly of the stapling and cutting assembly of FIG. 16.
Figure 21:
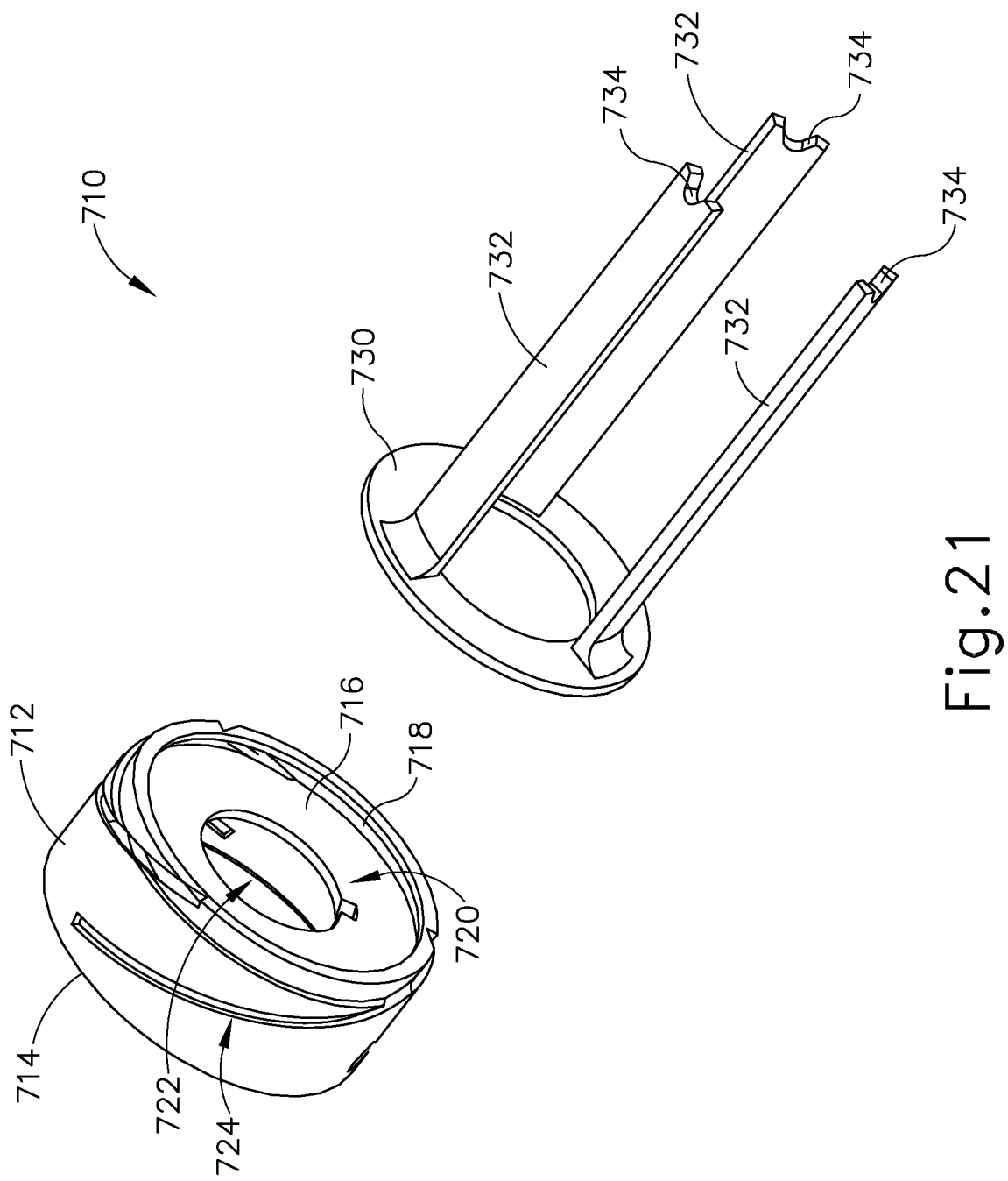
FIG. 21 depicts an exploded perspective view of the blade assembly of FIG. 20.
Figure 22:
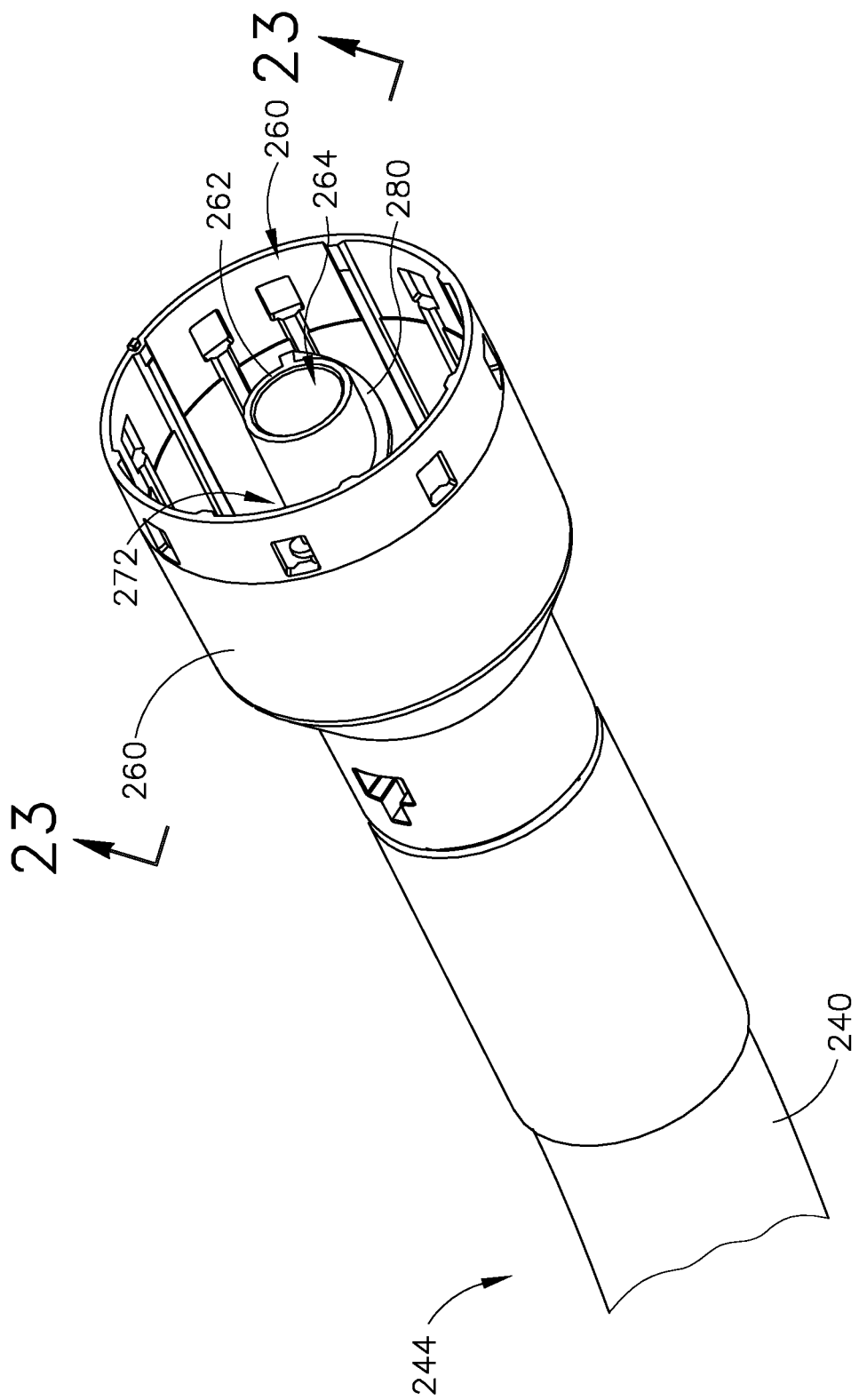
FIG. 22 depicts a perspective view of the distal end of the shaft assembly of FIG. 11.

As best seen in FIGS. 20-21, blade assembly (710) includes a cylindrical blade member (712) and a coupling ring (730). Cylindrical blade member (712) includes a distal cutting edge (714), a proximally presented surface (716), and a flange (718). Cylindrical blade member (712) also defines an inner core pathway (720), a tissue cavity housing (722), and a rotational camming slot (724). Inner core pathway (720) is sized to receive an inner core (262) of distal housing (260), while tissue cavity housing (722) is dimensioned to receive severed tissue as will be described in greater detail below. Rotational camming slot (724) is configured to mate with a spiraling blade cam (280) on inner core (262) of distal housing (260) such that cylindrical blade member (712) rotates as cylindrical blade member (712) is actuated. Proximally presented surface (716) and flange (718) are configured to rotationally couple with coupling ring (730) such that cylindrical blade member (712) may rotate relative to coupling ring (730) while blade assembly (710) actuates.

Coupling ring (730) also includes three proximally presented firing legs (732) each terminating into a drive coupler (734). As will be described in greater detail below, proximally presented firing legs (732) and respective drive couplers (734) are positioned to selectively align with a portion of reciprocating driver assembly (400) such cylindrical blade member (712) may sever excess tissue independently of outer staple driver (750) and inner staple driver assembly (770).

B. Exemplary Proximal Housing of Shaft Assembly

As will be described in greater detail below, selected portions of proximal housing (210) are configured to couple with selected portions of handle assembly (11) for operative engagement. Proximal housing (210) includes a pair of nozzle portions (212, 214) that are substantially similar to nozzle portions (56, 58) described above, with differences described below.

Proximal housing (210) also includes a translating shuttle (216) and a chassis (218) housed within nozzle portions (212, 214). Similar to closure shuttle (62) described above, translating shuttle (216) includes a pair of proximally-protruding hooks (220) that are configured for attachment to attachment pin (42) that is attached to second closure link (38). Therefore, when properly coupled, translating shuttle (216) is configured to translate relative to chassis (218) in response to closure trigger (32) moving between the non-actuated pivotal position (as shown in FIG. 4A), and the actuated pivotal position (as shown in FIG. 4B) in accordance with the description above. As will be described in greater detail below, actuation of translating shuttle (216) is configured to actuate clutch assembly (500) to selectively couple and decouple trocar assembly (300) from intermediate firing shaft (226).

Similar to chassis (64) described above, chassis (218) includes a pair of tapered attachment portions (222) formed thereon that are adapted to be received within corresponding dovetail slots (76) formed within distal attachment flange portion (78) of frame (28). Each dovetail slot (76) may be tapered or generally V-shaped to seatingly receive attachment portions (222) therein. When attachment portions (222) are properly placed within dovetail slot (76), chassis (218) is longitudinally and rotationally fixed to frame (28) of handle assembly (11).

Additionally, proximal housing (210) includes a latch system for removably coupling proximal housing (210) to handle assembly (11) and, more specifically, to frame (28). In other words, while attachment portions (222) prevent longitudinal and rotational movement of chassis (218) relative to frame (28), latch system may prevent chassis (218) from vertically sliding out of dovetail slots (76) when properly coupled.

Figure 28:
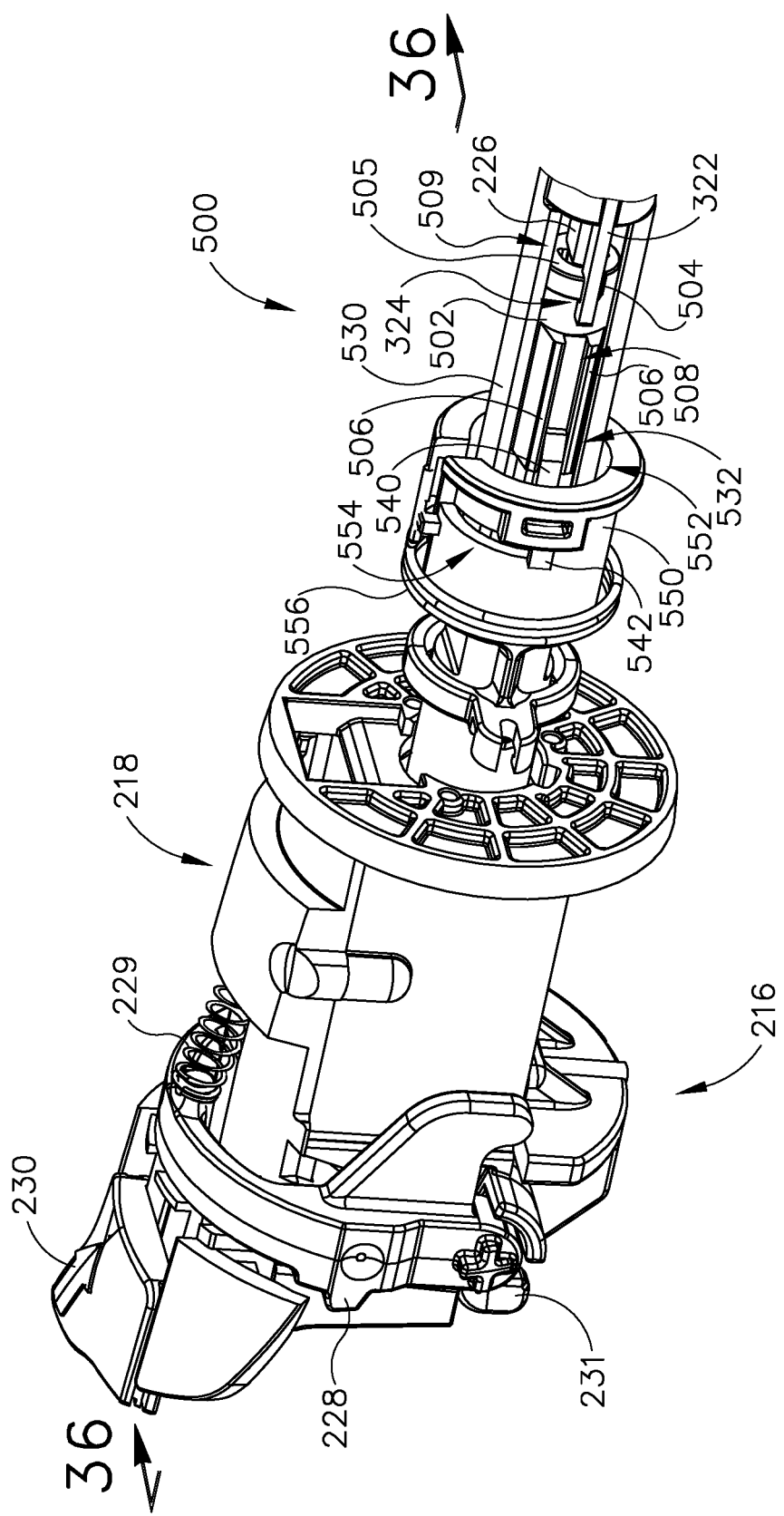
FIG. 28 depicts a perspective view of a clutch assembly of the interchangeable circular stapler shaft assembly of FIG. 8.

By way of example only, this latch system may include a lock yoke or other kind a lock member that is movably coupled to chassis (218). As shown in FIGS. 9 and 28, such a lock yoke may include two proximally protruding lock lugs (228) that are configured for releasable engagement with corresponding lock detents or groves (98) in frame (28). Actuation of the lock yoke may be accomplished by a latch button (230) that is both slidably mounted to chassis (218) and attached to lock lugs (228). As best seen in FIG. 28, latch button (230) and lock lugs (228) are proximally biased via a bias spring (229) such that lock lugs (228) are pivoted relative to chassis (218) about pivot point (231) toward a proximal, locked position. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (228) are retainingly seated within the corresponding lock detents or grooves (98). By way of further example only, proximal housing (210) may be removably coupled with handle assembly (11) in accordance with at least some of the teachings of U.S. Pub. No. 2017/0086823, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

Chassis (218) further includes an electrical connector (232) that may be substantially similar to electrical connector (106) described above. Therefore, electrical connector (232) may be operatively mounted to a shaft circuit board (not shown). Electrical connector (232) is configured for mating engagement with a corresponding electrical connector (108) on a handle control board (not shown). Further details regarding the circuitry and control systems may be found in U.S. Pub. No 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

As mentioned above, shaft assembly (156) further comprises intermediate firing shaft (226) having a shaft attachment lug (224) that is substantially similar to intermediate firing shaft (82) having shaft attachment lug (80) described above, respectively, with differences described below. Therefore, shaft attachment lug (224) is configured to be seated in cradle (84) in the longitudinally movable drive member (86) when shaft assembly (156) is properly coupled with handle assembly (11). As will be described in greater detail below, motor (118) is operable to drive intermediate firing shaft (226) to actuate trocar assembly (300) and a reciprocating drive assembly (400) in accordance with the descriptions herein.

To commence the coupling process between proximal housing (210) of shaft assembly (156) and handle assembly (11), the clinician may position chassis (218) of proximal housing (210) above or adjacent to frame (28) such that tapered attachment portions (222) formed on chassis (218) are aligned with dovetail slots (76) in frame (28). The clinician may then move shaft assembly (156) along an installation axis (IA) that is perpendicular to the longitudinal axis of intermediate firing shaft (226) to seat attachment portions (222) in "operative engagement" with the corresponding dovetail receiving slots (76). In doing so, shaft attachment lug (224) on intermediate firing shaft (226) will also be seated in cradle (84) in the longitudinally movable drive member (86) and the portions of pin (42) on second closure link (38) will be seated in the corresponding hooks (220) in translating shuttle (216).

When properly coupled, nozzle portions (212, 214) are operable to rotate end effector (158) and selected portions of shaft assembly (156) excluding translating shuttle (216), chassis (218), lock lugs (228), bias spring (229), electrical connector (332), and latch button (230). In particular, nozzle portions (212, 214) may rotate end effector (158) and selective portions of shaft assembly (156) about the longitudinal axis defined by outer sheath (240). Therefore, a clinician may rotate end effector (158) and shaft assembly (156) to a desired rotational orientation in preparation for an end-to-end anastomosis procedure.

Similar to shaft assembly (16) discussed above, at least five systems of interchangeable circular stapler attachment (150) may be operatively coupled with at least five corresponding systems of handle (14). A first system comprises a frame system that couples and/or aligns the frame or spine of shaft assembly (156) with frame (28) of handle (14), as described above. A second system is the latch system that releasably locks shaft assembly (156) to handle (14), as described above.

A third system is the first drive system (30) that may operatively connect closure trigger (32) of handle (14) and translating shuttle (216) of proximal housing (210). As mentioned above, and as described below, the third system may be used to actuate clutch assembly (500) to selectively couple and decouple trocar assembly (300) from intermediate firing shaft (226).

A fourth system is a trocar and firing drive system operatively connecting control rocker (112) and firing trigger (33) of handle (14) with intermediate firing shaft (226) of shaft assembly (156). As outlined above, shaft attachment lug (224) operatively connects with cradle (84) of longitudinal driver member (86). This fourth system provides motorized actuation of either trocar assembly (300) or reciprocating driver member (400), depending on the pivotal position of closure trigger (32). As will be described in greater detail below, when closure trigger (32) is in a non-actuated pivotal position (as shown in FIG. 4A), the fourth system operatively connects control rocker (112) with trocar assembly (300), thereby providing motorized actuation of trocar assembly (300). When closure trigger (32) is in an actuated pivotal position (as shown in FIG. 4B), the fourth system operatively connects firing trigger (33) with reciprocating drive assembly (400), resulting in sequential stapling and cutting of tissue captured between anvil (600) and deck member (640) in response to actuation of firing trigger (33).

A fifth system is an electrical system that can signal to control circuit in handle (14) that shaft assembly (156) has been operatively engaged with handle (14), to conduct power and/or communicate signals between shaft assembly (156) and handle (14).

Other kinds of systems of interchangeable shaft assembly (156) that may be operatively coupled with at corresponding systems of the handle (14) will be apparent to those of ordinary skill in the art in view of the teachings herein.

C. Exemplary Outer Sheath and Distal Housing of Shaft Assembly

As best seen in FIGS. 8-9, 12, and 22-23B, shaft assembly (156) includes outer sheath (240) and distal housing (260). Outer sheath (240) extends from a proximal portion (242) coupled to nozzles (212, 214), to a distal portion (244) coupled to distal housing (260). Outer sheath (240) houses a portion of intermediate firing shaft (226), trocar assembly (300), reciprocating drive assembly (400), and clutch assembly (500). Distal housing (260) houses stapling and cutting assembly (700), a portion of trocar assembly (300), and a portion of reciprocating drive assembly (400).

Figure 23A:
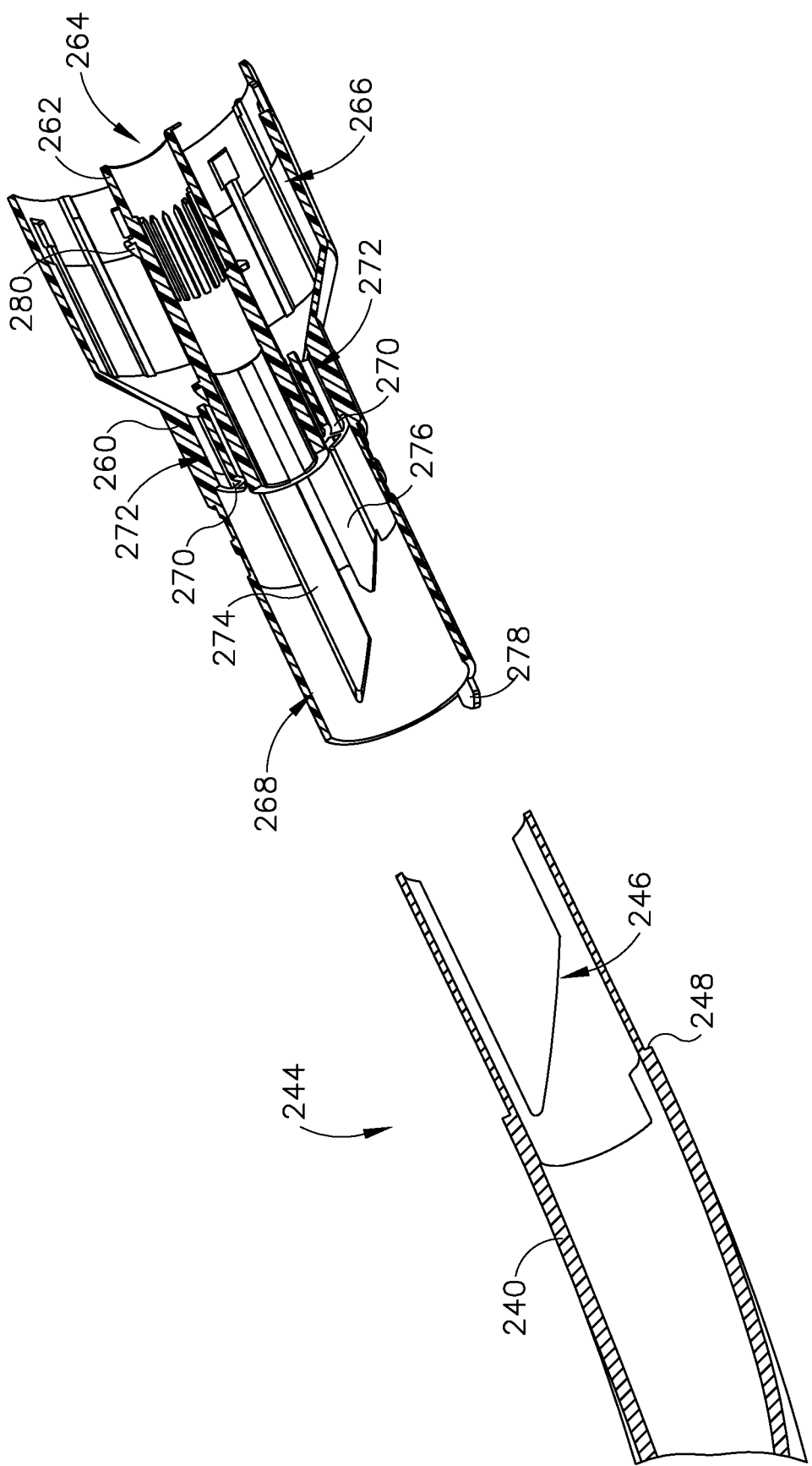
FIG. 23A depicts a cross-sectional side view of an outer sheath of the shaft assembly of FIG. 11 aligned to couple with a distal housing of the shaft assembly, taken along line 23-23 of FIG. 22.
Figure 23B:
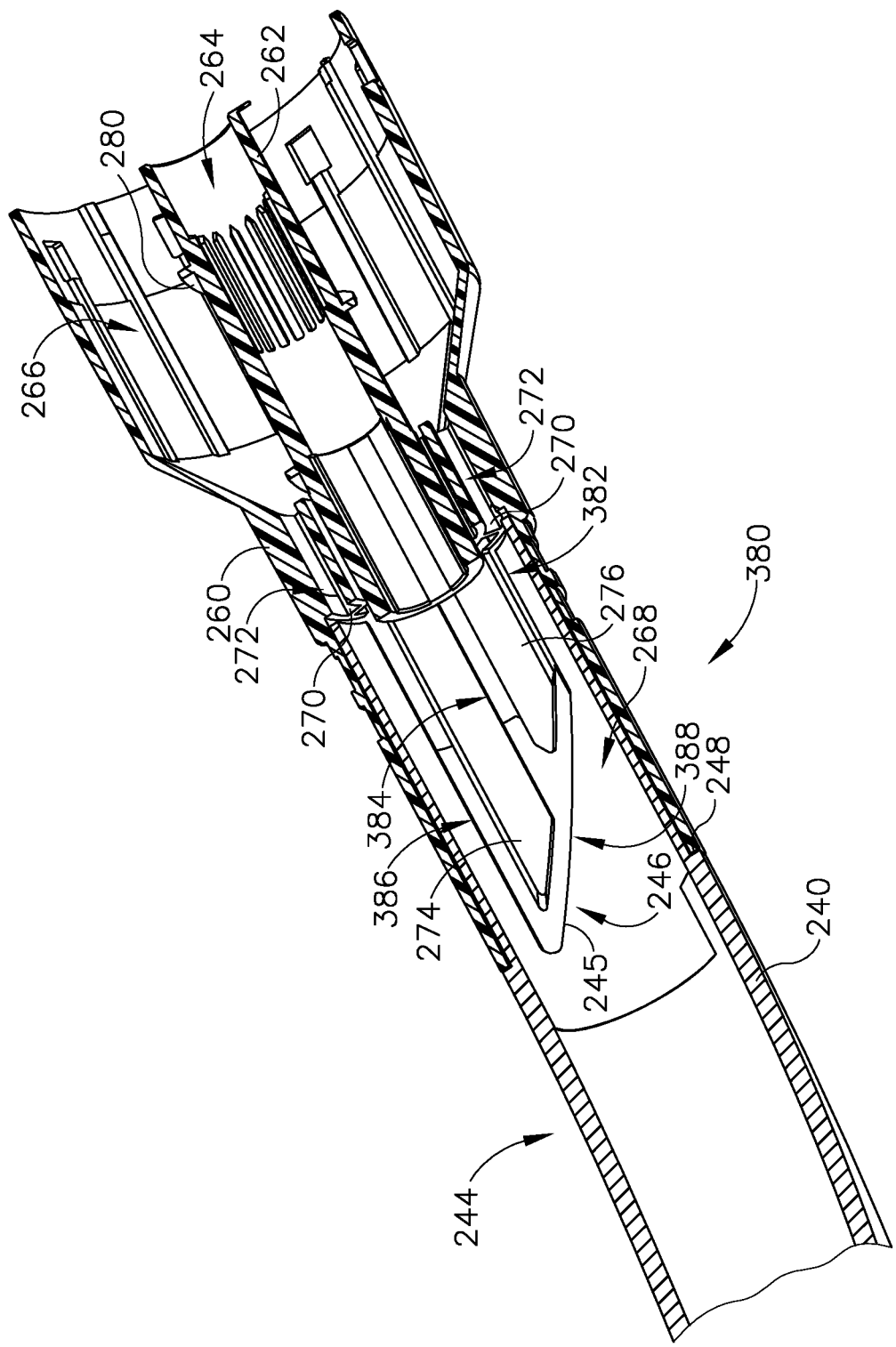
FIG. 23B depicts a cross-sectional side view of the outer sheath of FIG. 23A coupled with the distal housing of FIG. 23A, taken along line 23-23 of FIG. 22.
Figure 24:
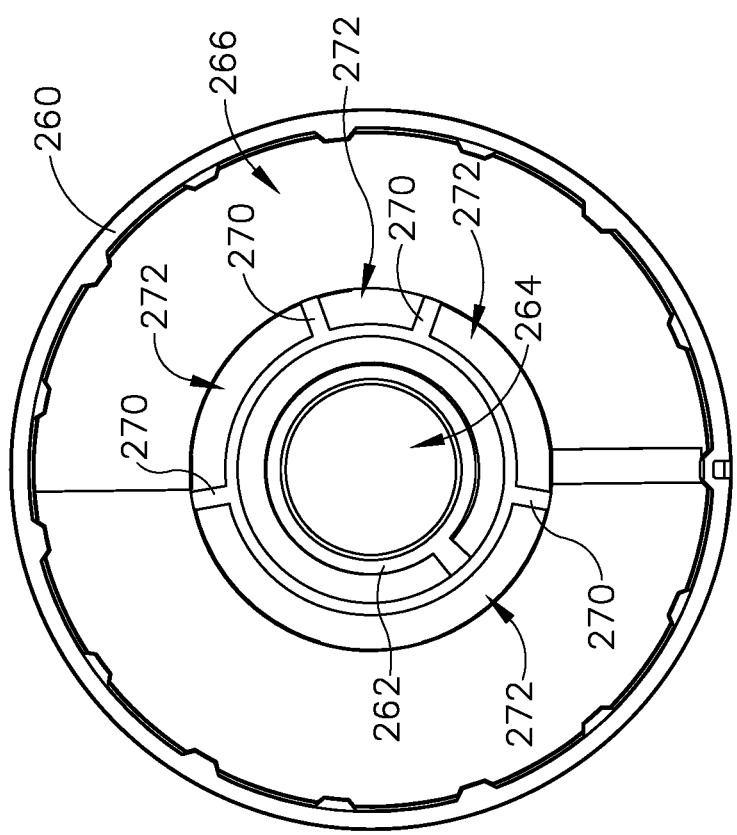
FIG. 24 depicts a top plan view of the distal housing of FIG. 23A.
Figure 25:
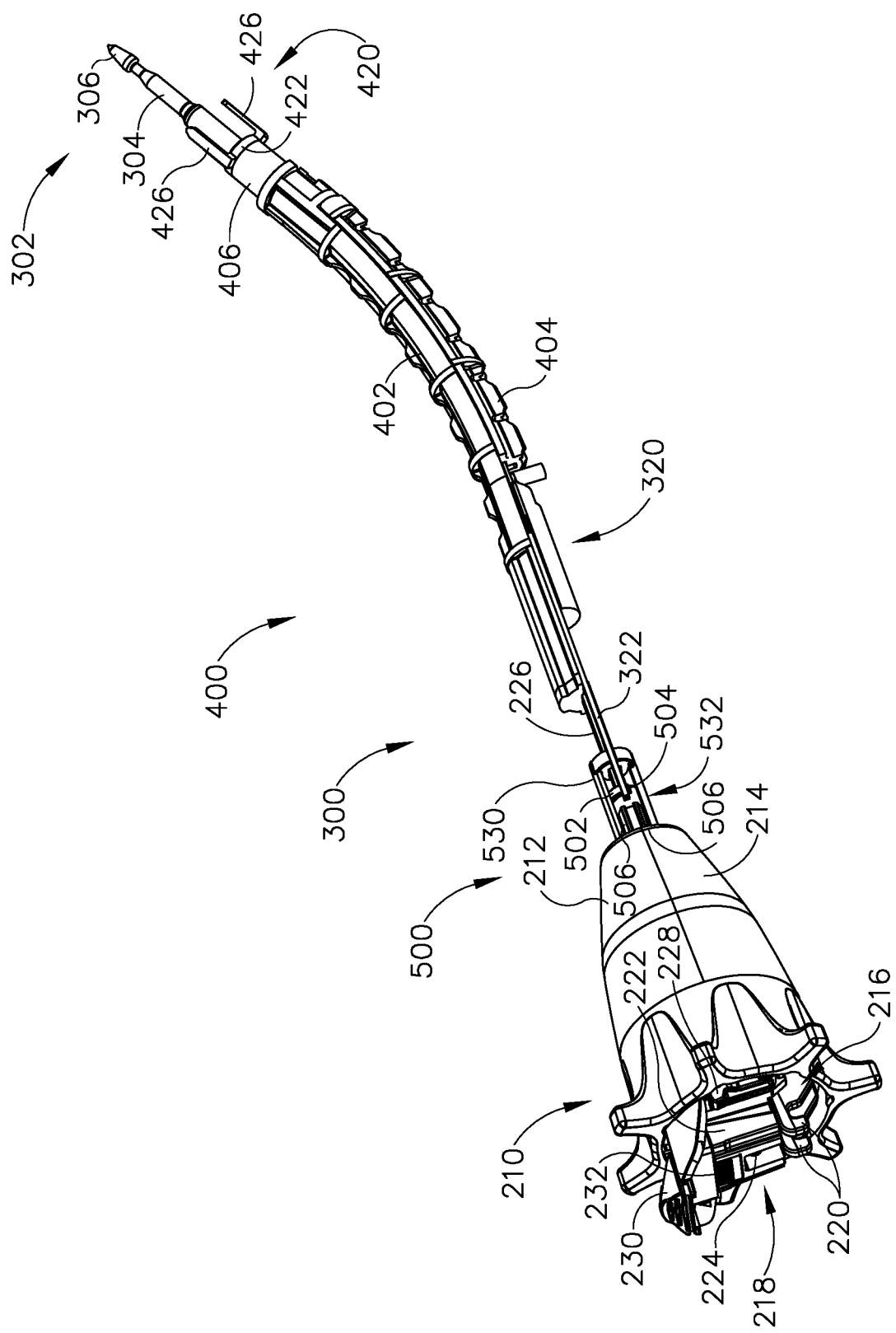
FIG. 25 depicts a perspective view of the interchangeable circular stapler shaft assembly of FIG. 8, where the end effector of FIG. 11, the outer sheath of FIG. 23A, and the distal housing of FIG. 23A are omitted for purposes of clarity.
Figure 26:
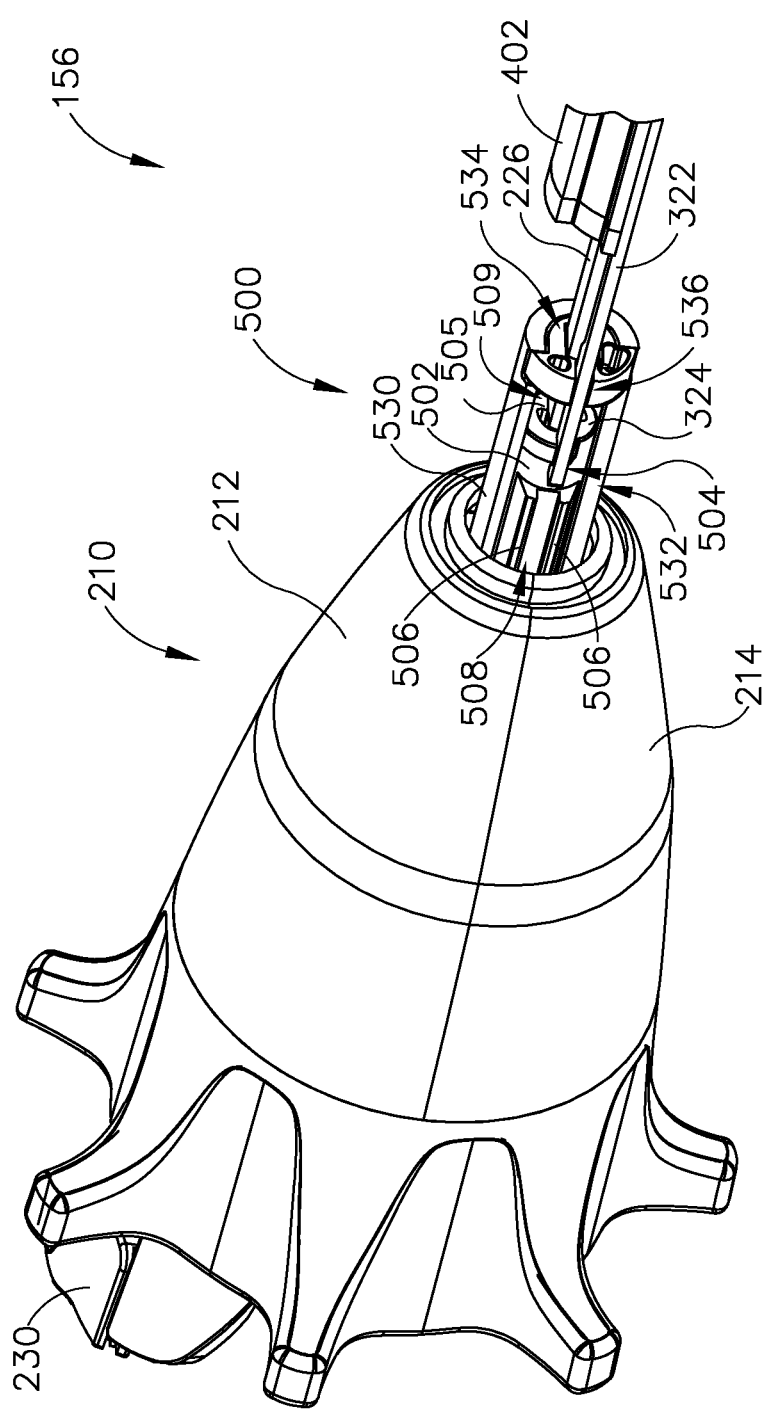
FIG. 26 depicts a perspective view a proximal housing of the interchangeable circular stapler attachment and a proximal end of the shaft assembly of FIG. 11, where the outer sheath of FIG. 23A is omitted for purposes of clarity.

Outer sheath (240) may be somewhat flexible so that a clinician may flex outer sheath (240), portions of trocar assembly (300), and portions of reciprocating drive assembly (400) to a desired longitudinal profile for accessing a targeted anatomical passageway of a patient. As best seen in FIGS. 23A, distal portion (244) of outer sheath (240) defines a distal cutout (246). Additionally, distal portion (244) of outer sheath (240) includes a ledge (248) configured to abut against a proximal end of distal housing (260). As best seen in FIGS. 50A-50G, ledge (248) defines a notch (250) configured to receive a proximally presented nub (278) of distal housing (260) to help couple distal housing (260) and outer sheath (240).

Distal housing (260) includes a distal housing chamber (266) and a proximal housing chamber (268). Distal housing chamber (266) is configured to slidably house staple drivers (752, 772) of outer staple driver (750) and inner staple driver sections (780), respectively, as well as blade member (712) of blade assembly (710). Proximal housing chamber (286) is configured to slidably house firing legs (732, 752, 772) of blade assembly (710), outer staple driver (750), and inner staple driver sections (780), respectively. Additionally, as will be described in greater detail below, proximal housing chamber (286) is configured to slidably house a distal end of reciprocating driver assembly (400) such that reciprocating driver assembly (400) may selectively engage firings legs (732, 752, 772).

Distal housing (260) includes inner core (262) extending from proximal housing chamber (268) into distal housing chamber (266). The interior of inner core (262) defines a trocar pathway (264) dimensioned to slidably house a portion of trocar assembly (300), such that trocar assembly (300) may extend from proximal housing chamber (268) all the way through distal housing chamber (266) to couple with, and actuate anvil (600). Inner core (262) is attached to the interior of proximal housing chamber (268) via coupling members (270). Coupling members (270), proximal housing chamber (268), and inner core (262) also define firing leg pathways (272) that are dimensioned to allow firings legs (732, 752, 772) to actuate blade assembly (710), outer staple driver (750), and inner staple driver assembly (770), respectively, within distal housing chamber (266). In other words, firing legs (732, 752, 772) may extending from distal housing chamber (266) to proximal housing chamber (268) via firing leg pathways (272).

Outer sheath (240) and distal housing (260) are configured to couple together to define a drive assembly pathway (380). In particular, as shown between FIGS. 23A-23B, proximal housing chamber (268) includes a first interior protrusion (274) and a second interior protrusion (276), both extending radially inward. When properly coupled, first interior protrusion (274), second interior protrusion (276), and the profile of distal cutout (246) define drive assembly pathway (380). Drive assembly pathway (380) includes a first stapling pathway (382), a second stapling pathway (384), and a blade actuation pathway (386), all connected to each other by a connecting channel (388). Connecting channel (388) is partially defined by a camming face (245) of distal cutout (246). As will be described in greater detail below, camming face (245) of drive assembly pathway (380) is configured to properly orient selected portions of reciprocating drive assembly (400) based on a longitudinal position of reciprocating driver assembly (400) to sequentially drive outer staple driver (750), inner staple driver assembly (770), and blade assembly (710).

D. Exemplary Clutch Assembly of Shaft Assembly

As mentioned above, when properly coupled, motor (118) is operable to drive intermediate firing shaft (226) to actuate trocar assembly (300) or reciprocating drive assembly (400), depending on the pivotal position of closure trigger (32). In particular, when closure trigger (32) is in the non-actuated pivotal position (as shown in FIG. 4A), control rocker (112) may activate motor (118) to drive intermediate firing shaft (226), which may drive trocar assembly (300), independently of reciprocating drive assembly (400), relative to outer sheath (240) and distal housing (260). When closure trigger (32) is in the actuated pivotal position (as shown in FIG. 4B), control rocker (112) may no longer activate motor (118), but firing trigger (33) may activate motor (118) to drive intermediate firing shaft (226), which in turn drives reciprocating drive assembly (400), independently of trocar assembly (300), in a sequential firing motion to drive individual portions stapling and cutting assembly (700), as will be described in greater detail below.

As also mentioned above, and as will be described in greater detail below, shaft assembly (156) includes clutch assembly (500), which is configured to selectively decouple trocar assembly (300) from intermediate firing shaft (226) such that activation of firing trigger (33) may allow intermediate firing shaft (226) to drive reciprocating drive assembly (400) without driving trocar assembly (300). In particular, clutch assembly (500) is configured to decouple trocar assembly (300) from intermediate firing shaft (226) in response to pivotal movement of closure trigger (32).

Figure 27:
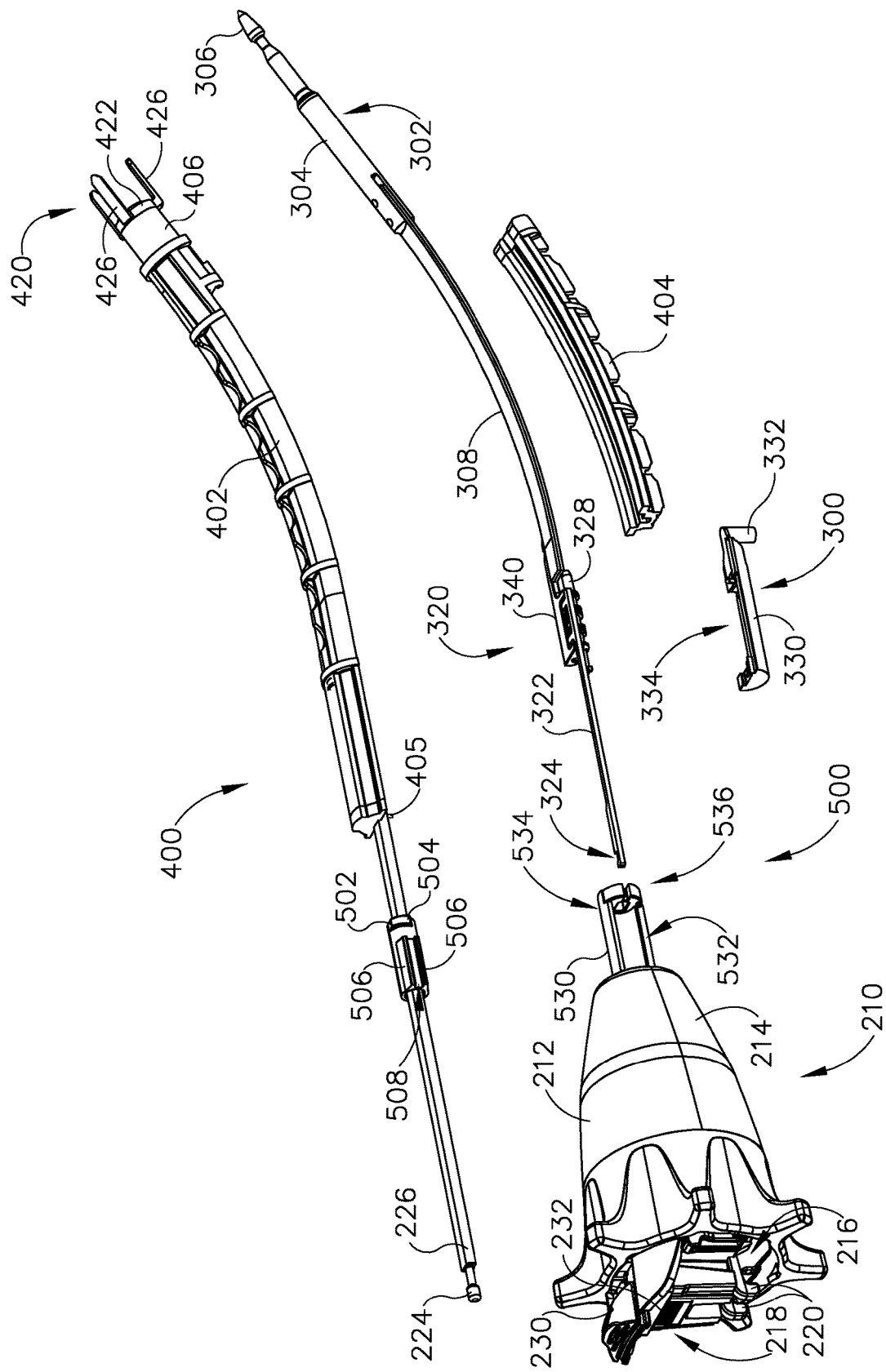
FIG. 27 depicts an exploded perspective view of the interchangeable circular stapler shaft assembly of FIG. 8 where the end effector of FIG. 11, the outer sheath of FIG. 23A, and the distal housing of FIG. 23A are omitted for purposes of clarity.
Figure 37:
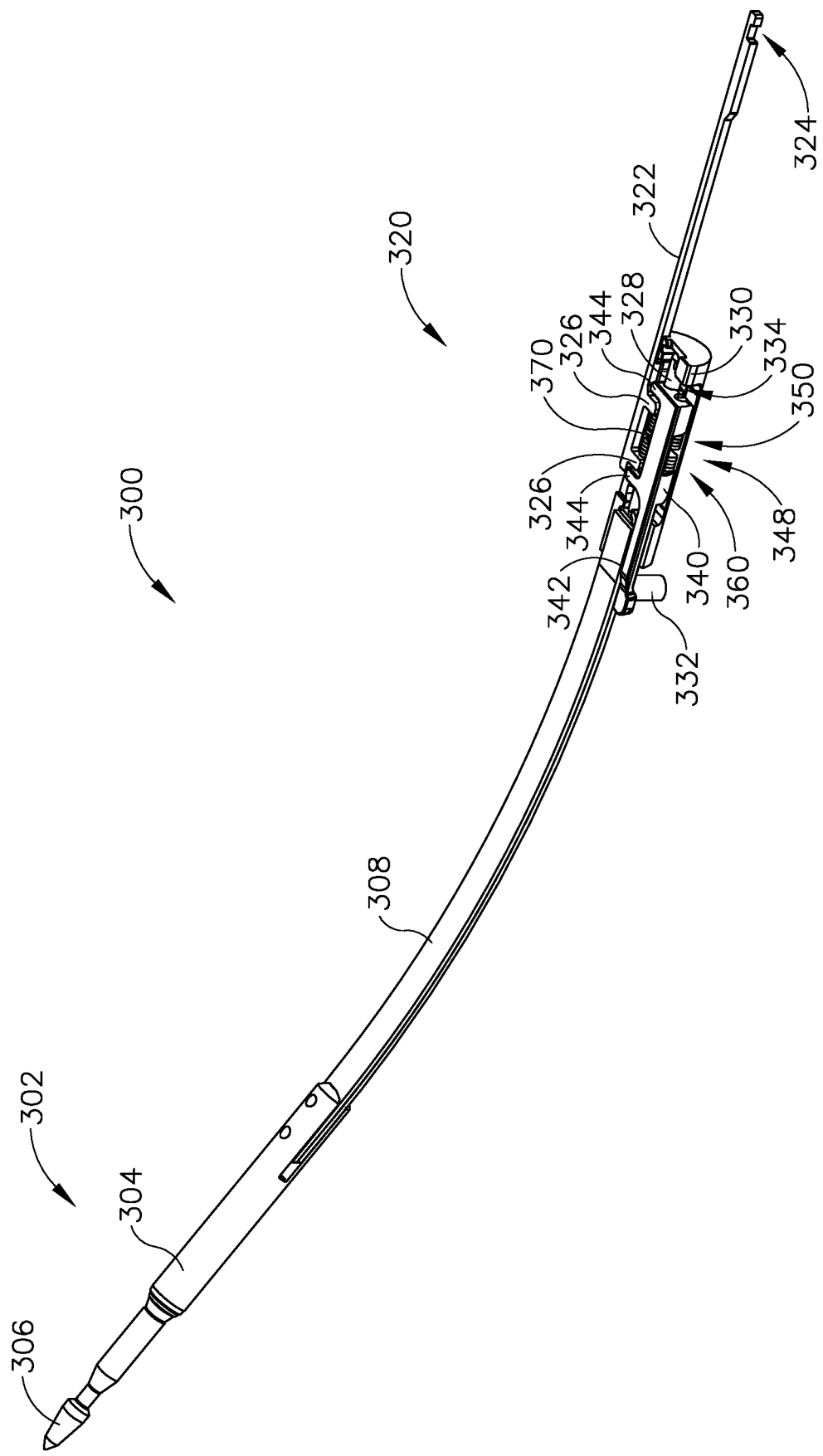
FIG. 37 depicts a perspective view of a trocar assembly of the shaft assembly of FIG. 11.

As best seen in FIGS. 27 and 37, trocar assembly (300) includes a drive arm (322), a longitudinal locking assembly (320), a trocar articulation band assembly (308), and a trocar (302). Trocar (302) includes a shaft (304) and a head (306). Head (306) is configured to selectively couple with anvil (600) such that trocar (302) may drive anvil (600) toward and away deck member (640) to compress and release tissue as described above, and as will be described in greater detail below. Trocar band assembly (308) connects shaft (304) of trocar (302) with longitudinal locking assembly (320). Trocar band assembly (308) is sufficiently flexible to bend in response to a clinician bending the longitudinal profile of outer sheath (240) as described above.

Drive arm (322) includes a pair of distal engagement arms (326). Additionally, drive arm (322) defines a proximal clutch engagement notch (324). As will be described in more detail below, clutch engagement notch (324) is configured to selectively couple with intermediate firing shaft (226) via clutch assembly (500) based on the pivotal position of closure trigger (32), when properly coupled. As will also be described in more detail below, distal engagement arms (326) are configured to actuate the rest of trocar assembly (300) when clutch engagement notch (324) is selectively coupled with intermediate firing shaft (226) via clutch assembly (500).

Longitudinal locking assembly (320) may help lock the position of trocar (302) relative to distal housing (260) and outer sheath (240) when drive arm (322) is stationary. In particular, longitudinal locking assembly (320) may help ensure that trocar (302), and in turn anvil (600), remain stationary when clutch engagement notch (324) and intermediate firing shaft (226) are no longer engaged.

Figure 33:
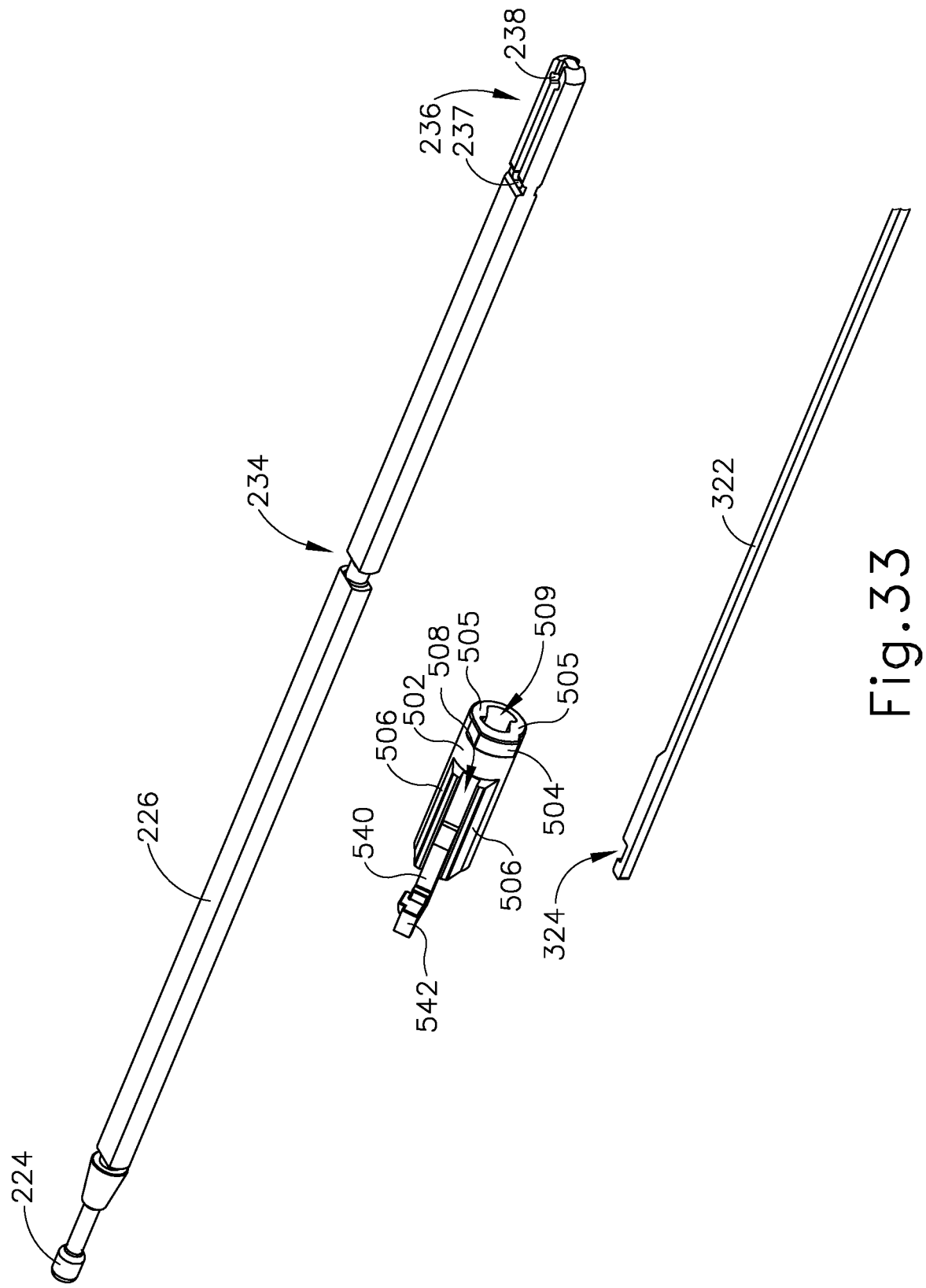
FIG. 33 depicts an exploded perspective view of a rotational shifter of the clutch assembly of FIG. 28, an intermediate firing shaft of the shaft assembly of FIG. 11, and a drive arm of the shaft assembly.
Figure 34:
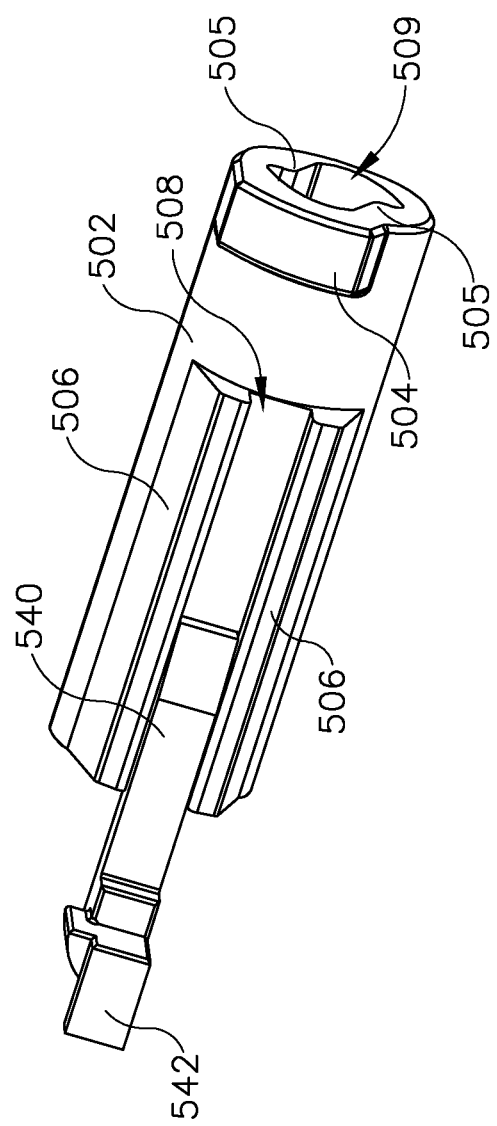
FIG. 34 depicts a perspective view of the rotational shifter of FIG. 33.
Figure 35:
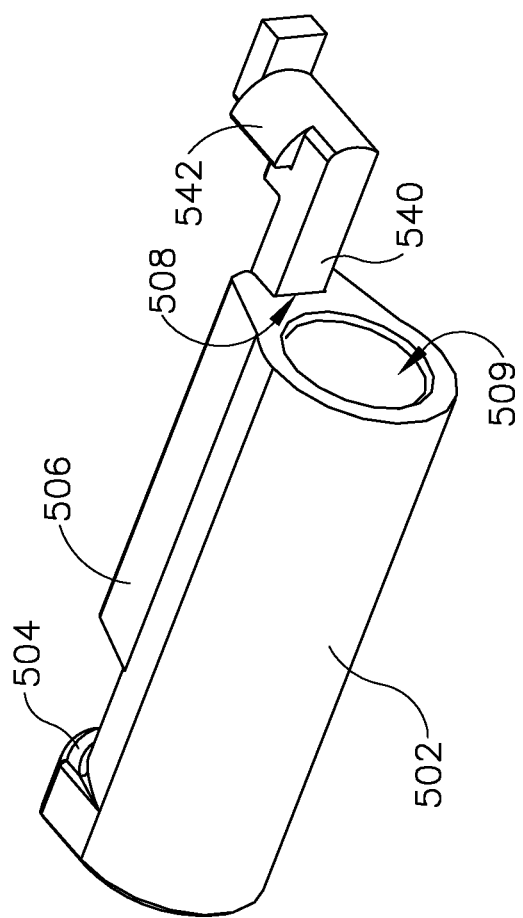
FIG. 35 depicts another perspective view of the rotational shifter of FIG. 33.

As best seen in FIG. 33, intermediate firing shaft (226) defines a recess (234) and a distal slot (236). Recess (234) is dimensioned to rotationally couple with a rotational shifter (502) of clutch assembly (500). In other words, rotational shifter (502) may rotate relative to intermediate firing shaft (226) around the longitudinal axis defined by intermediate firing shaft (226), but rotational shifter (502) is longitudinally fixed with intermediate firing shaft (226) such that intermediate firing shaft (226) may longitudinally drive rotational shifter (502).

Figure 47:
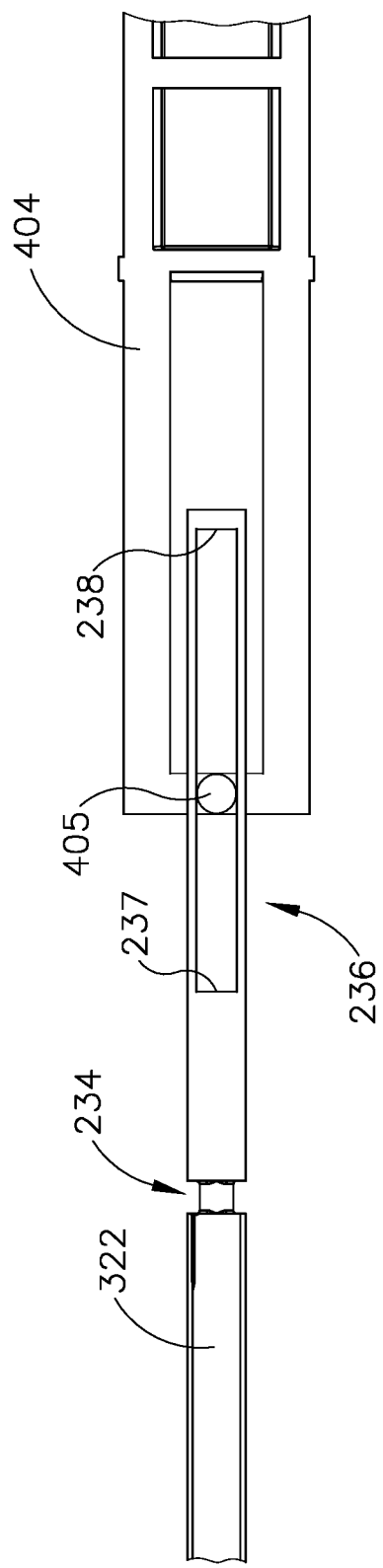
FIG. 47 depicts a bottom plan view of a portion of the reciprocating drive assembly of FIG. 45.

As best seen in FIG. 47, distal slot (236) houses a driving pin (405) of reciprocating drive member (400). Distal slot (236) extends from an advancing surface (237) to a retracting surface (238). Advancing surface (237) and retracting surface (238) may abut against driving pin (405) to advance or retract reciprocating drive member (400), respectively. Therefore, motion of intermediate firing shaft (226) where driving pin (405) is between advancing surface (237) or retracting surface (238), without touching either, does not drive reciprocating drive member (400). Therefore, motion of intermediate firing shaft (226) where driving pin (405) does not abut against advancing surface (237) or retracting surface (238) may be used to independently actuate trocar assembly (300) relative to reciprocating drive member (400). In other words, the longitudinal length of distal slot (236) may be dimensioned for the travel length required to actuate trocar assembly (300) to properly couple with, and retract, anvil (600).

Figure 29:
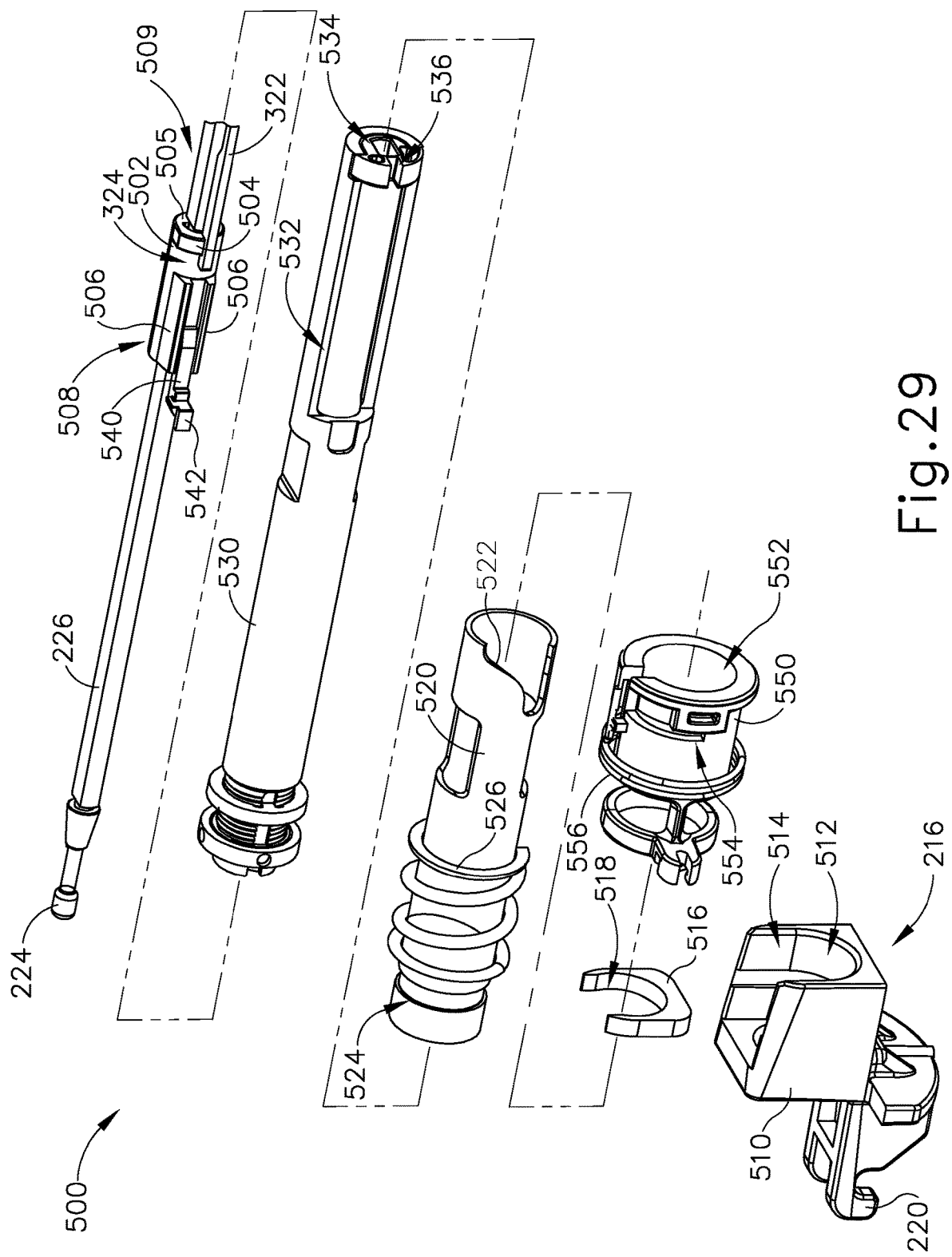
FIG. 29 depicts an exploded perspective view of the clutch assembly of FIG. 28.
Figure 30:
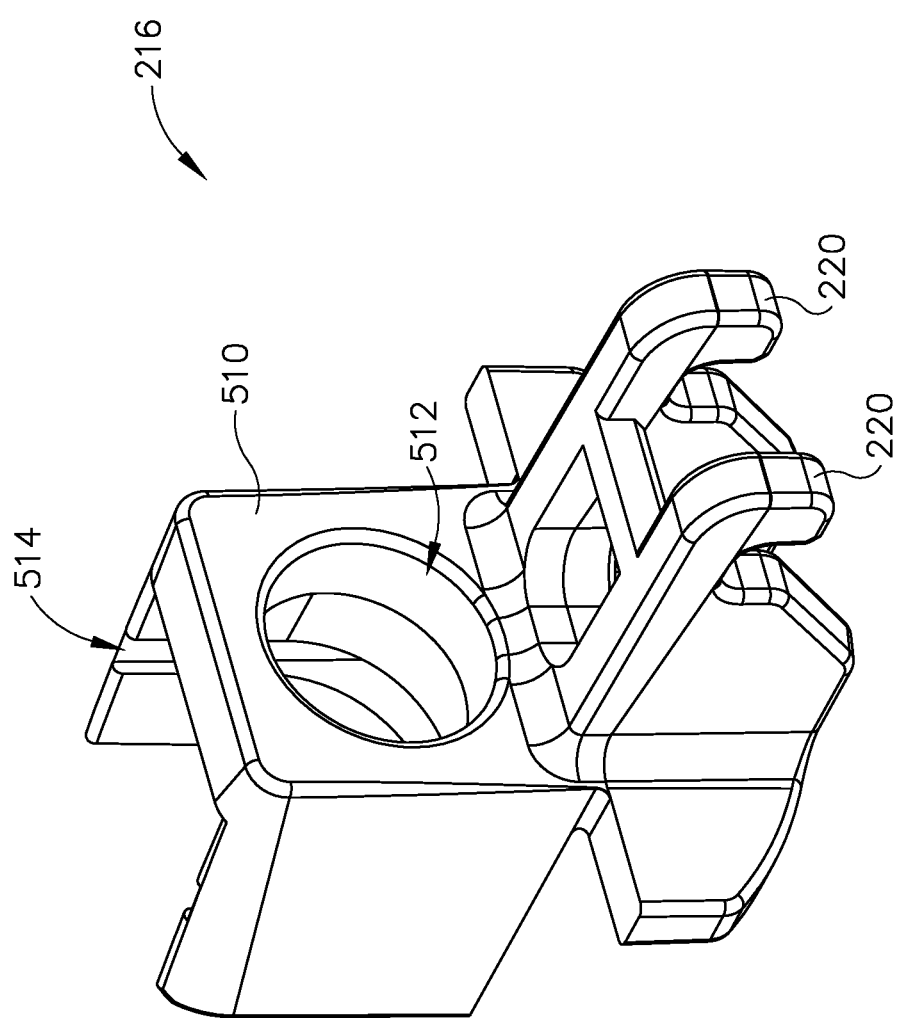
FIG. 30 depicts a perspective view of a translating shuttle of the clutch assembly of FIG. 28.
Figure 31:
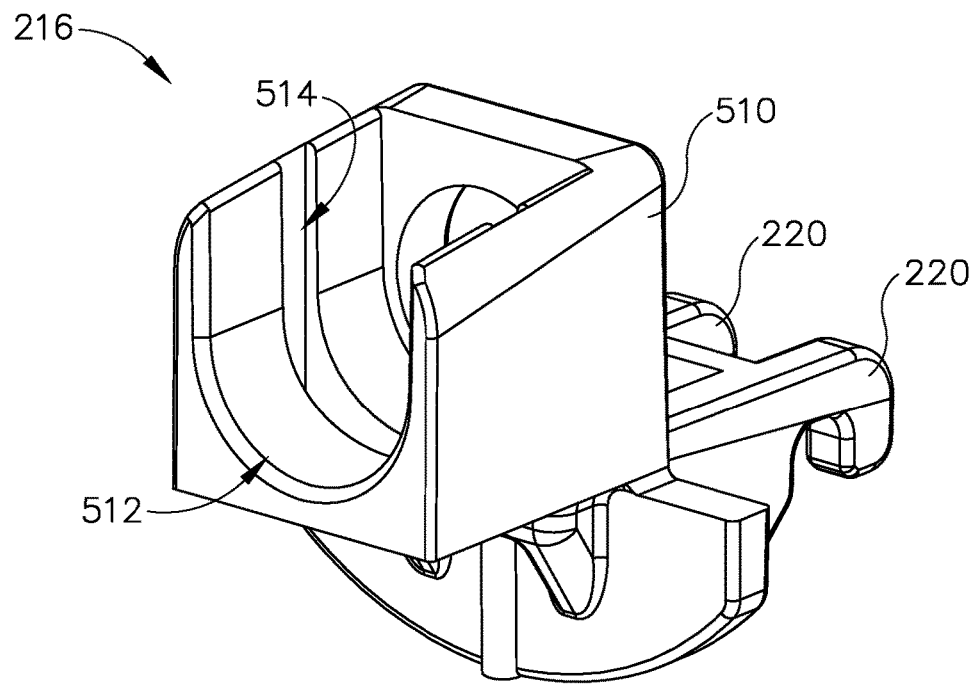
FIG. 31 depicts another perspective view of the translating shuttle of FIG. 30.
Figure 32:
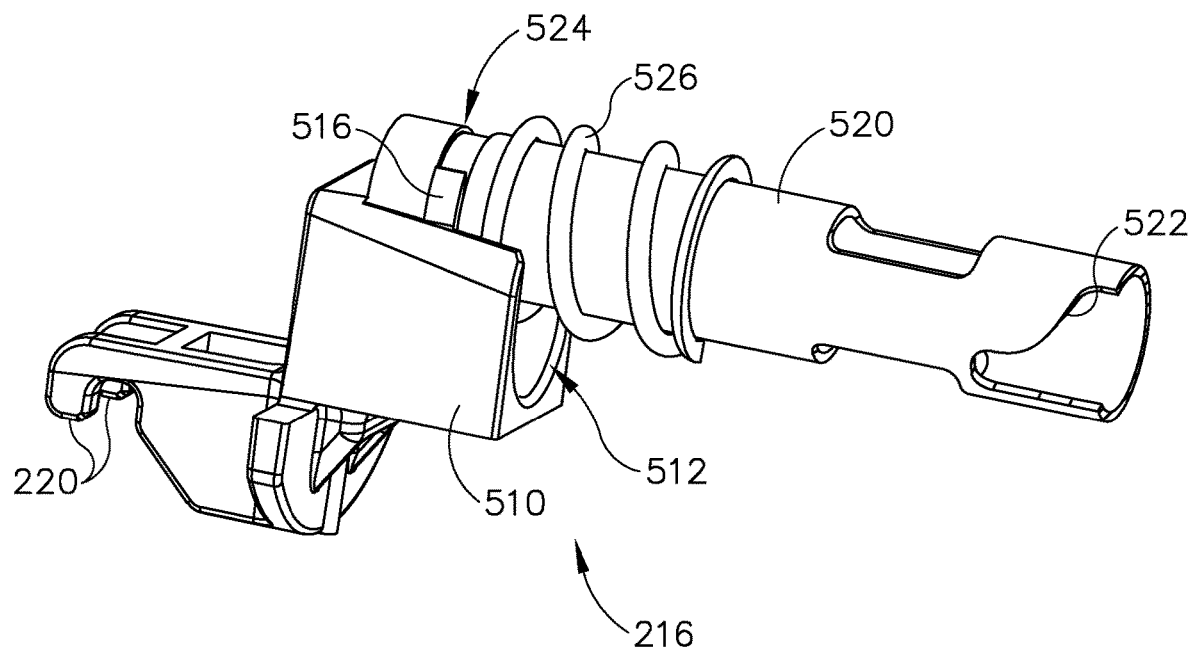
FIG. 32 depicts a perspective view of the translating shuttle of FIG. 30 coupled with a translating tube of the clutch assembly of FIG. 28.

FIGS. 28-36C show clutch assembly (500) as a whole or selected portions thereof. As best seen in FIG. 29, clutch assembly (500) includes rotational shifter (502), a translatable housing (510), a translatable tube (520), a U-shaped coupler (516), a sheath (530), a key member (540), and a key member housing (550). As will be described in greater detail below translatable housing (510) and U-shaped coupler (516) may linearly drive translatable tube (520) to rotate shifter (502) to selectively engage and disengage intermediate firing shaft (226) with trocar assembly (300).

Translatable housing (510) is fixed to translating shuttle (216). Therefore, movement of translating shuttle (216) results in movement of translatable housing (510). Translatable housing (510) defines a tube opening (512) and a cutout (514). Tube opening (512) may receive a proximal end of translatable tube (520) while cutout (514) is dimensioned to couple with U-shaped coupler (516) such that longitudinal movement of translatable housing (510) results in longitudinal movement of U-shaped coupler (516). U-shaped coupler (516) defines an interior opening (518) dimensioned to receive a portion of translatable tube (520) defining an exterior recess (524). Interior opening (518) of U-shaped coupler (516) couples with exterior recess (524) of translatable tube (520) such that translatable tube (520) may rotate about its longitudinal axis relative to U-shaped coupler (516), but also such that translatable tube (520) longitudinally travels with U-shaped coupler (516). Therefore, translation of translating shuttle (216) and translatable housing (510) may longitudinally drive U-shaped coupler (516) and translatable tube (520). Additionally, translatable tube (520) may rotate relative to U-shaped coupler (516) and translatable housing (510).

Figure 36A:
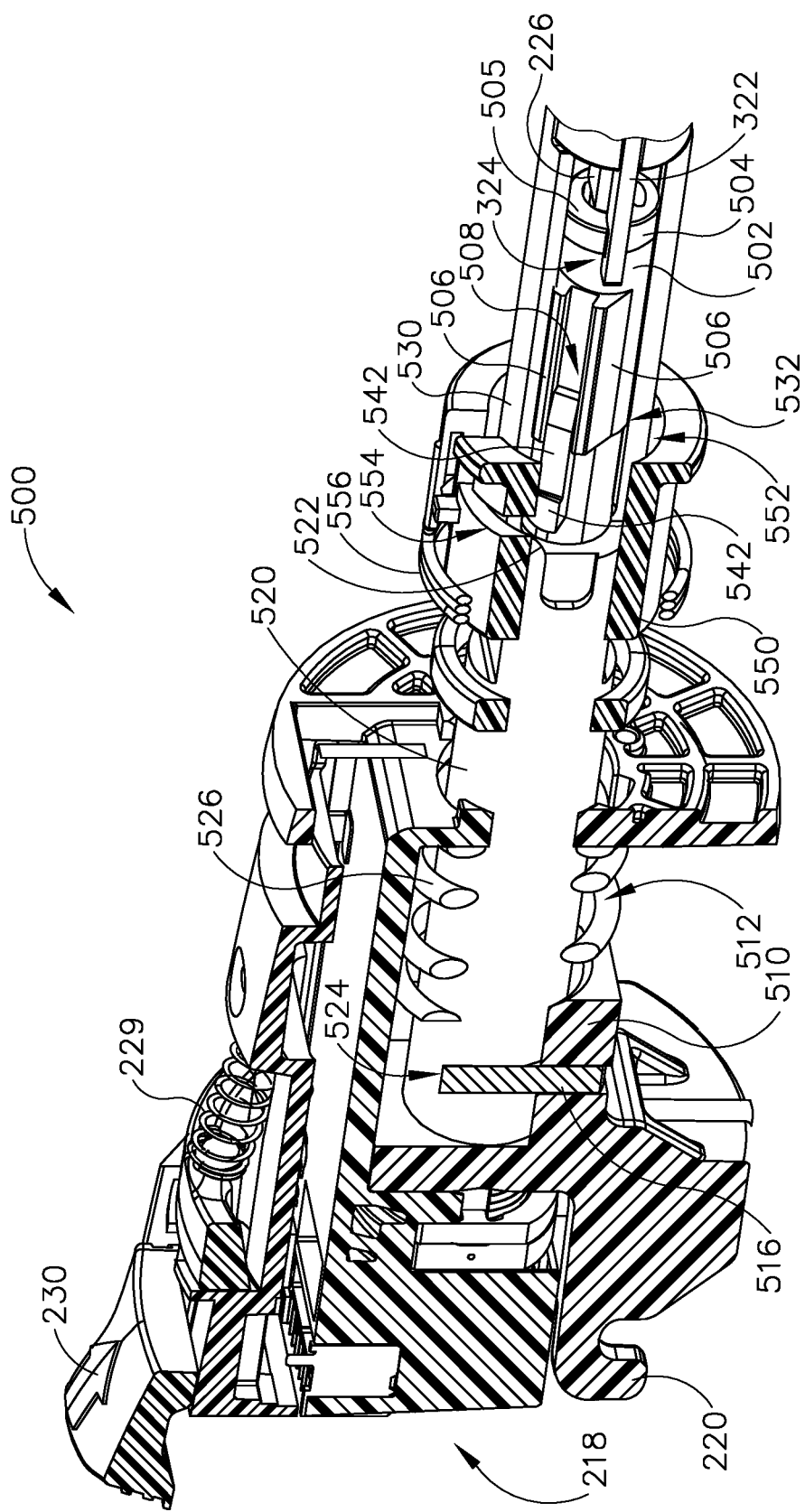
FIG. 36A depicts a cross-sectional perspective view of the clutch assembly of FIG. 28, taken along line 36-36 of FIG. 28, where the rotational shifter of FIG. 33 is engaged with the drive arm of FIG. 33, while the intermediate firing shaft of FIG. 33 is in a first longitudinal position.
Figure 36B:
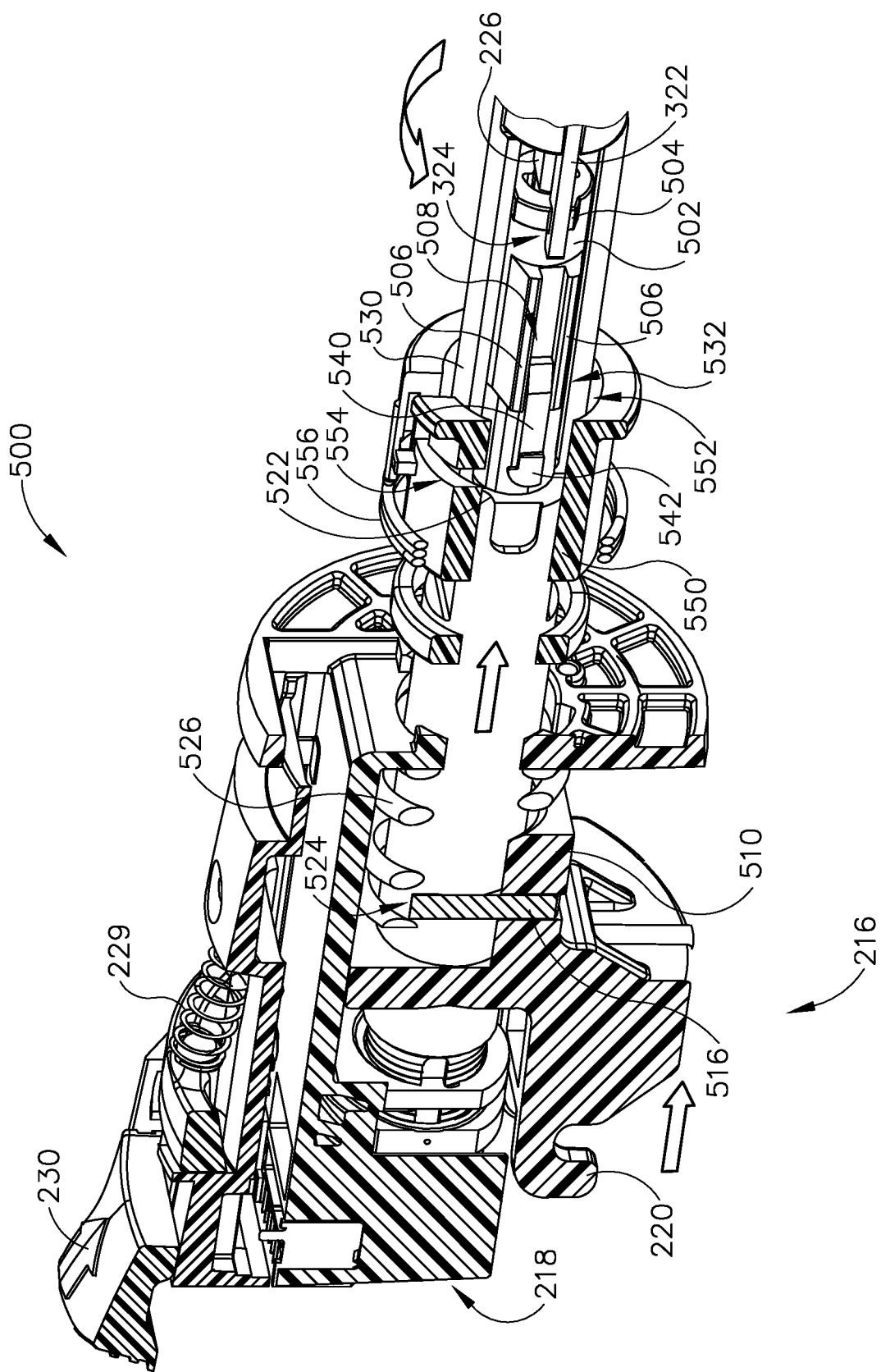
FIG. 36B depicts a cross-sectional perspective view of the clutch assembly of FIG. 28, taken along line 36-36 of FIG. 28, where the rotational shifter of FIG. 33 is disengaged with the drive arm of FIG. 33, while the intermediate firing shaft of FIG. 33 is in the first longitudinal position.
Figure 36C:
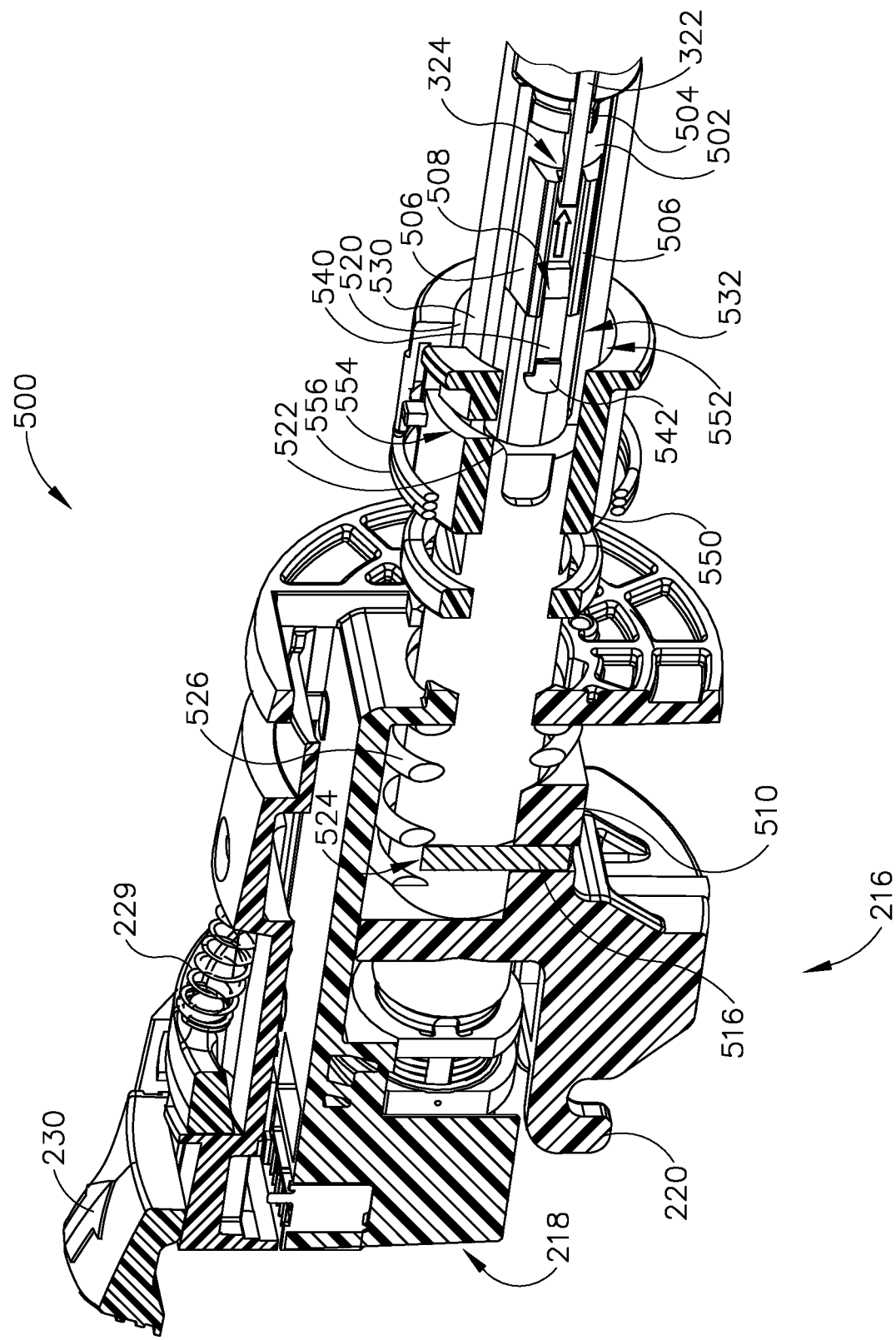
FIG. 36C depicts a cross-sectional perspective view of the clutch assembly of FIG. 28, taken along line 36-36 of FIG. 28, where the rotational shifter of FIG. 33 is disengaged with the drive arm of FIG. 33, while the intermediate firing shaft of FIG. 33 is in a second longitudinal position.

As described above, when properly coupled with handle assembly (11), translating shuttle (216) is configured to longitudinally actuate based on the pivotal position of closure trigger (32). Therefore, the pivotal position of closure trigger (32), when properly coupled with interchangeable circular stapler attachment (150), may determine to longitudinal position of translatable tube (520). In particular, when closure trigger (32) is in the non-actuated pivotal position (as shown in FIG. 4A), translatable tube (520) will be in a proximal position (as shown in FIG. 36A). When closure trigger (32) is in the actuated pivotal position (as shown in FIG. 4B), translatable tube (520) will be in a distal position (as shown in FIGS. 36B-36C).

In addition to exterior recess (524), translatable tube (520) includes a distal camming surface (522). As will be described in greater detail below, translation of translatable tube (520) from the proximal position to the distal position drives distal camming surface (522) against key member (540) to rotate key member (540) and rotational shifter (502) to decouple trocar assembly (300) from intermediate firing shaft (226). A biasing spring (526) is housed around translatable tube (526) between a distal end of translatable housing (510) and a proximally presented interior surface of chassis (218). Biasing spring (526) biases translatable tube (526) toward the proximal position. Therefore, if a clinician pivots closure trigger (32) from the actuated pivotal position to the non-actuated pivotal position in accordance with the teachings above, biasing spring (526) may urge translatable tube (520) from the distal position (as shown in FIG. 36B) to the proximal position (as shown in FIG. 36A).

Rotational shifter (502) includes a sector flange (504), coupling flanges (505), and radial protrusions (506) defining a slot (508). Additionally, rotational shifter (502) defines a through bore (509) that receives intermediate firing shaft (226). Coupling flanges (505) rotatably couple rotational shifter (502) with intermediate firing shaft (226) via recess (234) of intermediate firing shaft (226). Key member (540) is slidably disposed within slot (508). Key member (540) also includes a laterally presented camming arm (542) that is housed within a circumferential key member slot (554) of key member housing (550).

Sector flange (504) is dimensioned to rotate into and out of engagement with clutch engagement notch (324) of drive arm (322) of trocar assembly (300), depending on the rotational position of rotational shifter (502). When sector flange (504) is engaged with drive arm (322) of trocar assembly (300), translation of intermediate firing shaft (226) will drive translation of drive arm (322) of trocar assembly (300), thereby actuating trocar assembly (300). When sector flange (504) is not engaged with drive arm (322) of trocar assembly (300), translation of intermediate firing shaft (226) will not affect the position of drive arm (322) or trocar assembly (300).

Translatable tube (520) houses sheath (530), while sheath (530) houses intermediate firing shaft (226) and rotational shifter (502). Sheath (530) defines a lateral opening (532), a first distal opening (534), and a second distal opening (536). Lateral opening (532) is sized to accommodate laterally presented camming arm (542), radial protrusions (506), and sector flange (504) such that all may extend from an interior of sheath (530) to an exterior of sheath (530). Additionally, lateral opening (532) extends along a longitudinal length to accommodate translation of rotational shifter (502). First distal opening (534) is dimensioned to slidably receive intermediate firing shaft (226), while second distal opening is dimensioned to slidably receive drive arm (322) of trocar assembly (300). Therefore, intermediate firing shaft (226) and drive arm (322) of trocar assembly (300) may longitudinal translate relative to sheath (530).

Key member housing (550) defines a tube opening (552) and circumferential key member slot (554). Tube opening (552) slidably houses translatable tube (520). A terminating end of circumferential key member slot (554) is configured to abut against laterally presented camming arm (542) such that rotation of laterally presented camming arm (542) in one direction forces rotation of key member housing (550) in the same direction; and such that rotation of key member housing (550) in a second, opposite, direction forces rotation of laterally presented camming arm (542) in the second direction.

Both sheath (530) and key member housing (550) are longitudinally fixed relative to nozzles (212, 214) or proximal housing (210). Sheath (530) is also rotational fixed to nozzles (212, 214) such that sheath (530) may not rotate relative to nozzles (212, 214) about the longitudinal axis defined by intermediate firing shaft (226). Key member housing (550) is ratably coupled to nozzles (212, 214) such that key member housing (550) may rotate relative to nozzles (212, 214) about the longitudinal axis defined by intermediate firing shaft (226). However, key member housing (550) includes a torsion spring (556) that interacts with an interior defined by nozzles (212, 214) to rotationally bias key member housing (550) to a first angular position (as shown in FIGS. 28 and 36A). As will be described below, torsion spring (556) allows key member housing (550) to urge key member (540) to rotate shifter (502) back into engagement with drive arm (322) once translatable tube (520) moves from the distal position (as shown in FIG. 36B) back to the proximal position (as shown in FIG. 36A).

FIGS. 36A-36C show exemplary use of clutch assembly (500) to disengage trocar assembly (300) from intermediate firing shaft (226). FIG. 36A shows translating shuttle (216) and translatable housing (510) in the proximal position. It should be understood, at this point, closure trigger (32) is in the non-actuated pivotal position (as shown in FIG. 4A). Therefore, a clinician may activate control rocker (112) such that motor (118) may longitudinally drive both longitudinal drive member (86) and intermediate firing shaft (226). At the position shown in FIG. 36A, sector flange (504) of rotational shifter (502) is engaged with clutch engagement notch (324) of drive arm (322). Therefore, if a clinician activates control rocker (112) to driver longitudinal driver member (86) and intermediate firing shaft (226), trocar assembly (300) will also actuate relative to outer sheath (240) and distal housing (260). As mentioned above, intermediate firing shaft (226) defines distal slot (236) housing drive pin (405) of reciprocating drive assembly (400) such that intermediate firing shaft (226) may actuate trocar assembly (300) along a length determined by distal slot (236) without actuating reciprocating drive member (400).

When a clinician no longer desires to actuate trocar assembly (300), such as when a clinician suitably couples trocar (302) with anvil (600) and retracts trocar (600) and anvil (600) to suitably compress tissue, the clinician may pivot firing trigger (32) to the actuated pivotal position (as shown in FIG. 4B). As mentioned above, when firing trigger (32) is in the actuated pivotal position, control rocker (112) may no longer activate motor (118), as firing trigger (33) may now activate motor (118) to drive intermediate firing shaft (226). As discussed above, when closure trigger (32) is in the actuated pivotal position, translating shuttle (216) and translatable housing (510) move from the proximal position (as shown in FIG. 36A) to the distal position (as shown in FIG. 36B). Additionally, translatable tube (520) moves from the proximal position to the distal position such that camming surface (522) forces laterally presented camming arm (542), key member (540), rotational shifter (502), and key remember housing (550) to rotate in the first angular direction from an engaged position to a disengaged position. In the disengaged position, as shown in FIG. 36B, sector flange (504) is rotated out of engagement with clutch engagement notch (324) of drive arm (322). Therefore, actuation of intermediate drive shaft (226) no longer actuates drive arm (322) or trocar assembly (300). Drive arm (322) is aligned with slot (508) of rotational shifter (502) such that drive arm (322) may be accepted by slot (508) in response to distal translation of rotational shifter (502).

Next, a clinician may activate firing trigger (33), which may actuate intermediate drive shaft (226) relative to trocar assembly (300) to drive reciprocating drive assembly (400) in accordance with the description below. As best seen in FIG. 36C, intermediate drive shaft (226) and rotational shifter (502) actuate independently from trocar assembly (300) due to sector flange (504) being disengaged with drive arm (322). Therefore, intermediate drive shaft (226) may longitudinally travel to abut against drive pin (405) of reciprocating drive assembly (400) with advancing surface (237) and retracting surface (238) to advance and retract reciprocating drive assembly (400), respectively.

Once reciprocating drive assembly (400) completes its firing cycle, as will be described in greater detail below, intermediate firing shaft (226) may return to the position shown in FIG. 36B. Encoder (115) may communicate all relative positions of longitudinal drive member (86), and therefore intermediate firing shaft (226), to control circuit (117). Therefore, control circuit (117) may instruct motor (118) to drive longitudinal drive member (86) and intermediate firing shaft (226) to all suitable positions. For instance, control circuit (117) may store the longitudinal position of drive member (86) and intermediate firing shaft (226) when a clinician pivots closure trigger (32) from the non-actuated pivotal position (as shown in FIG. 4A) to the actuated pivotal position (as shown in FIG. 4B), thereby storing the position of intermediate firing shaft (226) at the position shown in FIG. 36B.

A clinician may desire to once again regain control of trocar assembly (300) to actuate anvil (600) away from a newly formed anastomosis, as will be described in greater detail below. A clinician may then pivot closure trigger (32) from the actuation pivotal position (as shown in FIGS. 4B-4C), back to the non-actuated pivotal position (as shown in FIG. 4A) in accordance with the description above. With closure trigger (32) in the non-actuated pivotal position, translating shuttle (216), translatable housing (510), and translating tube (520) may move from the distal position back to the proximal position (as shown in FIG. 36A) such that camming surface (522) of translating tube (520) no longer contacts laterally presented camming arm (542). As mentioned above, torsion spring (556) rotationally biases key member housing (550) and key member (540) back to the angular position shown in FIG. 36A. Therefore, rotational shifter (502) is also rotated back to the position shown in FIG. 36A such that sector flange (504) reengages drive arm (322) of trocar assembly (300). Because sector flange (504) is reengaged with drive arm (322), and because closure trigger (32) is back in the non-actuated pivotal position, a clinician may activate motor (118) via control rocker (112) to actuate trocar assembly (300) and anvil (600).

E. Exemplary Trocar Longitudinal Locking Assembly

As mentioned above, trocar assembly (300) includes a longitudinal locking assembly (320) that may help lock the position of trocar (302) relative to distal housing (260) and outer sheath (240) when drive arm (322) is stationary. In particular, this may be useful to ensure trocar (302) and anvil (600) have sufficiently compressed tissue between proximal surface (604) of anvil (600) and distally presented deck surface (642) of deck member (640) during the stapling and severing process, as described in greater detail below.

Figure 38:
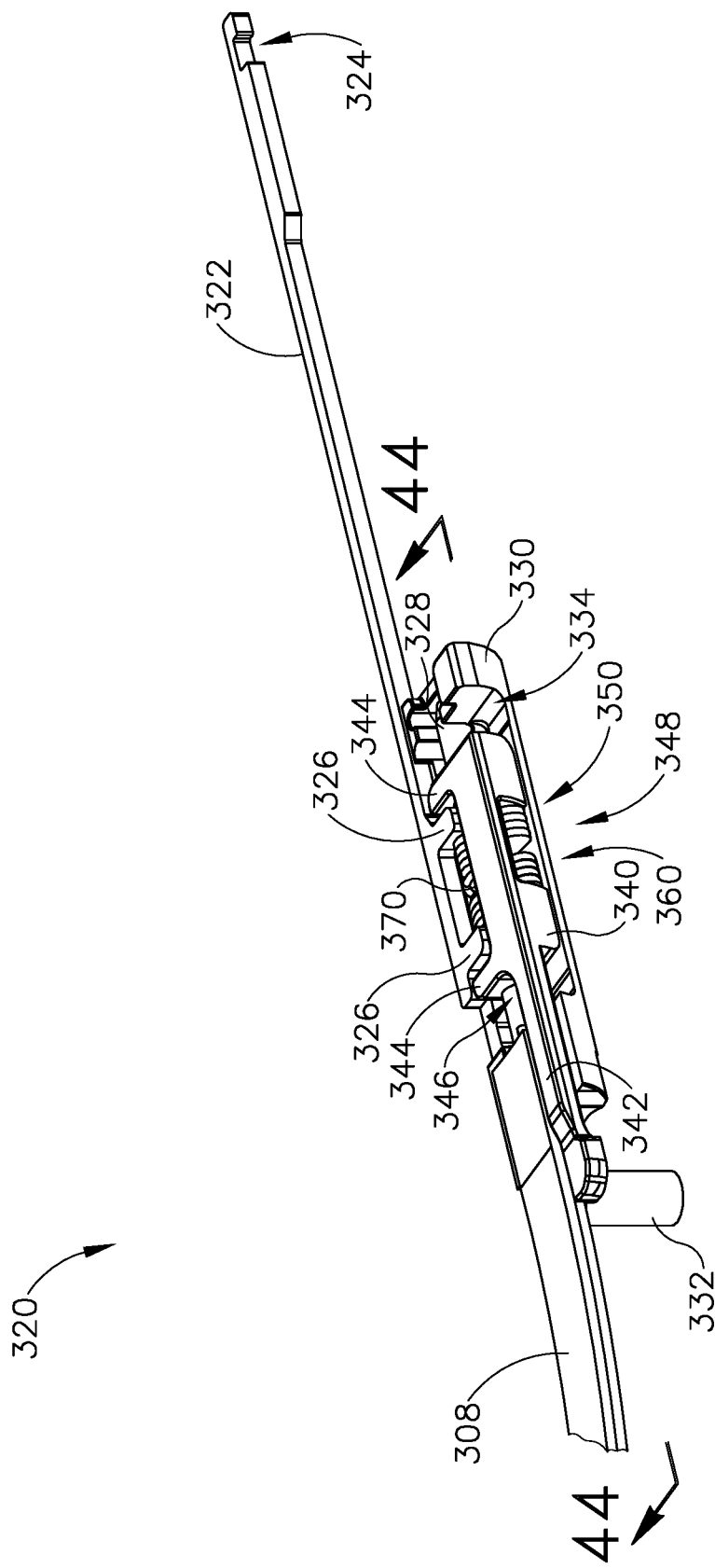
FIG. 38 depicts a perspective view of a longitudinal locking assembly of the trocar assembly of FIG. 37.
Figure 39:
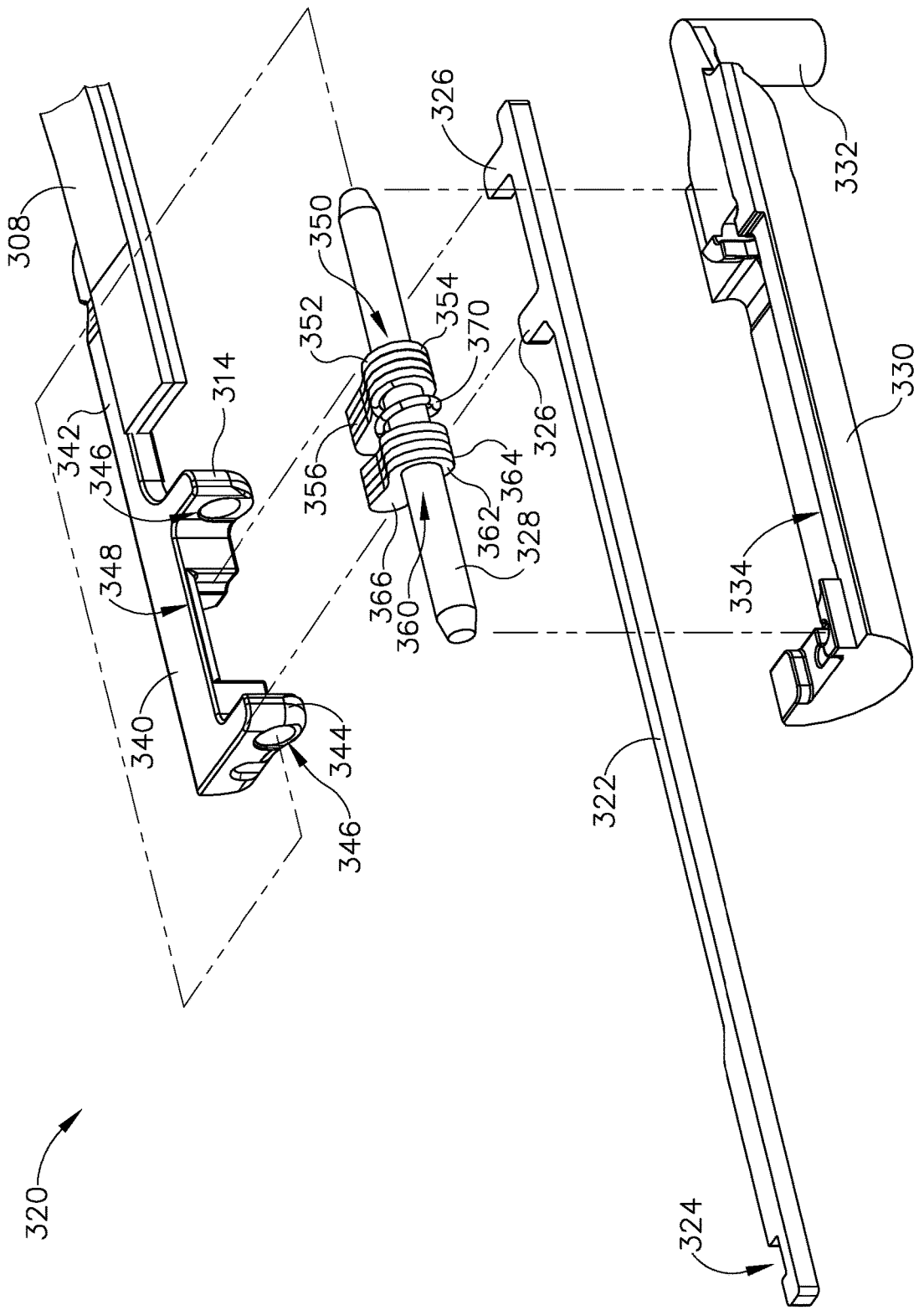
FIG. 39 depicts an exploded perspective view of the longitudinal locking assembly of FIG. 38.
Figure 40:
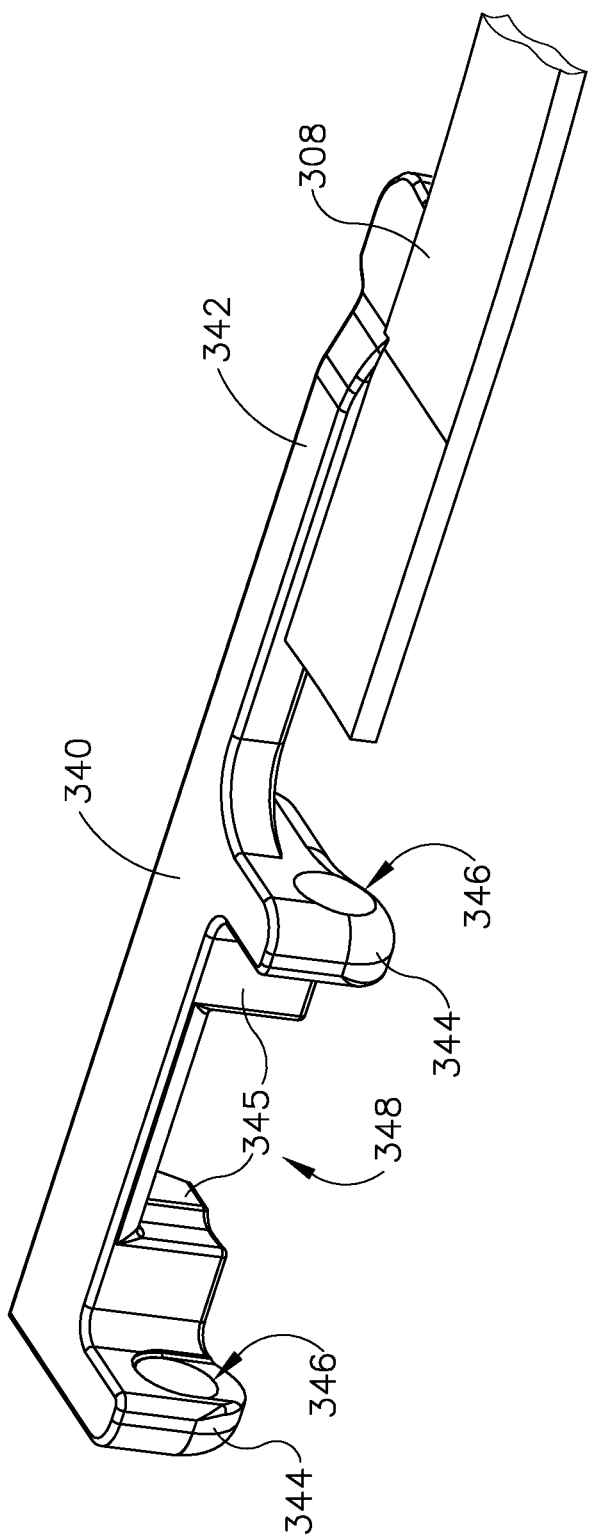
FIG. 40 depicts a perspective view of a band coupling body of the longitudinal locking assembly of FIG. 38.
Figure 41:
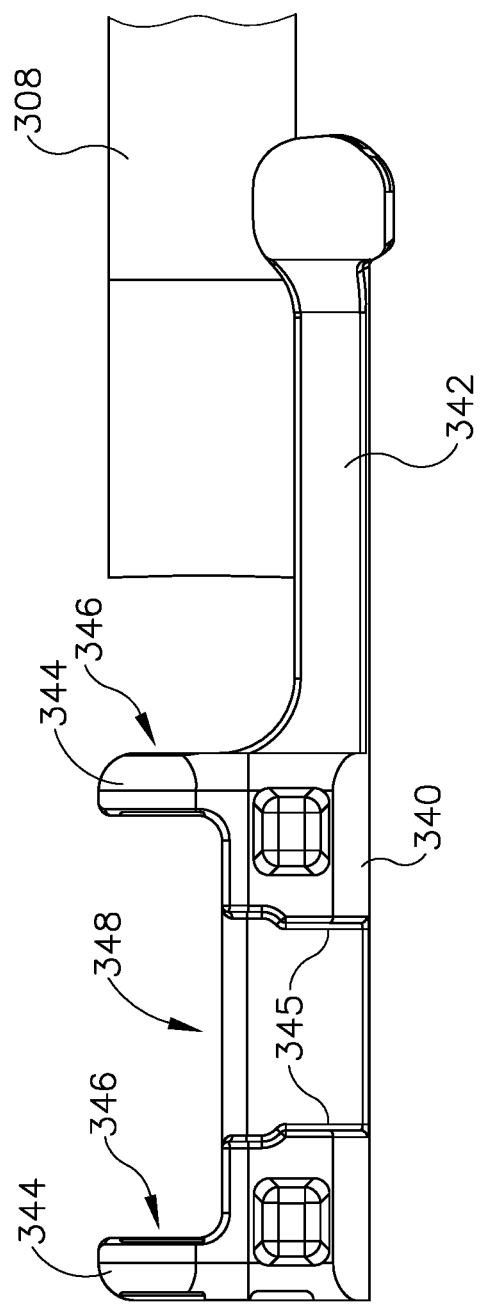
FIG. 41 depicts a bottom plan view of the band coupling body of FIG. 40.
Figure 42:
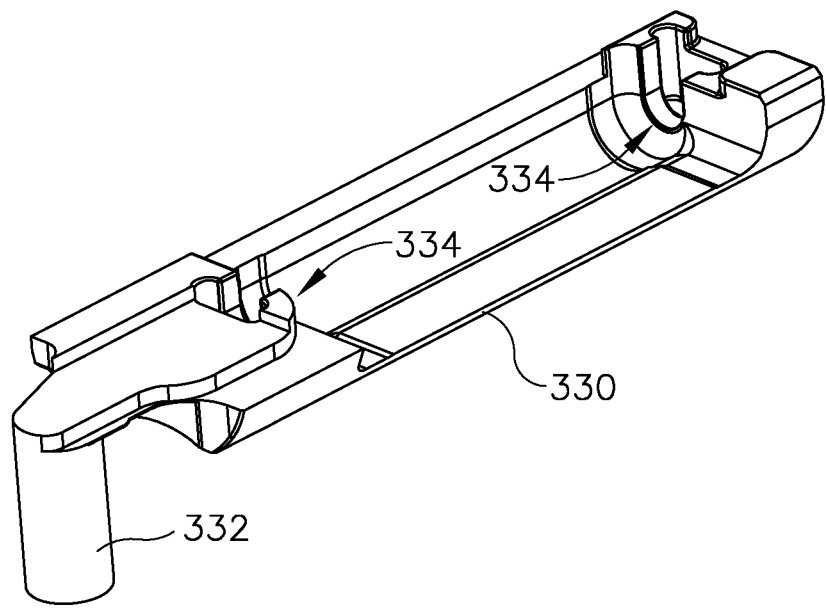
FIG. 42 depicts a perspective view of a fixed body of the longitudinal locking assembly of FIG. 38.
Figure 43:
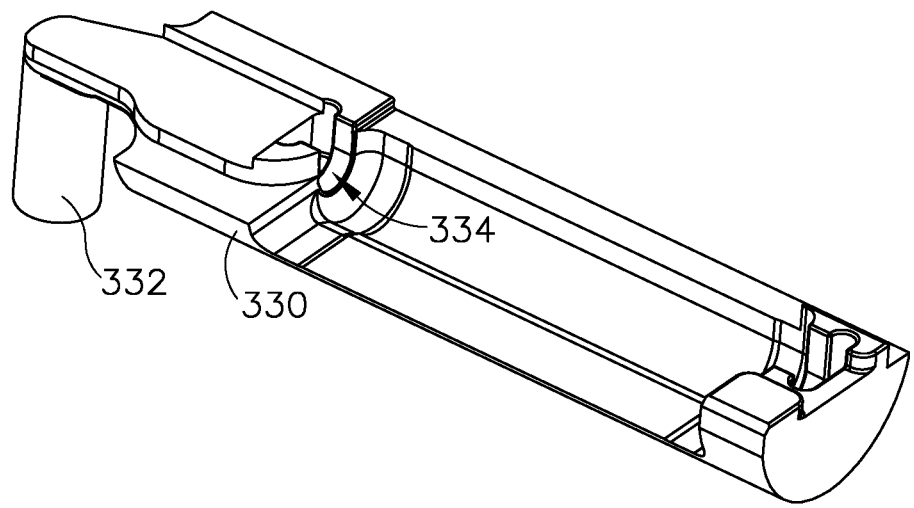
FIG. 43 depicts another perspective view of the fixed body of FIG. 42.

As best seen in FIGS. 38-39, longitudinal locking assembly (320) includes drive arm (322), a longitudinally extending pin (328) fixedly attached to a fixed body (330), a band coupling body (340) fixedly attached to trocar actuation band assembly (308), a first and second plurality of locking members (350, 360) slidably coupled along pin (328), and a bias member (370) disposed along pin (328) between first and second plurality of locking members (350, 360). As will be discussed in greater detail below, first and second plurality of locking members (350, 360) are biased against pin (328) to provide a frictional breaking force between band coupling body (340) and fixed body (330), thereby helping maintain the longitudinal position of band coupling body (340), actuation band assembly (308), and trocar (302). As will also be described in greater detail below, engagement arms (326) of drive arm (322) are configured to abut against first or second plurality of locking members (350, 260) to compress bias member (370), thereby reducing the frictional breaking force to accommodate longitudinal movement of band coupling body (340), actuation band assembly (308), and trocar (302).

Fixed body (330) provides a mechanical ground for longitudinal locking assembly (320). In particular, fixed body (330) includes a sheath coupling arm (332) that mates with a hole in outer sheath (340). Therefore, fixed body (330) is fixed relative to outer sheath (340). Fixed body (330) also defines a pin cutout (334) dimensioned to fixedly couple with pin (328) such that pin (328) also acts as a mechanical ground for longitudinal locking assembly (320).

Band coupling body (340) includes a distal coupling arm (342), and a pair of lateral pin arms (344) each defining pin holes (346). Pin holes (346) are dimensioned to slidably receive pin (328) such that band coupling body (340) may longitudinally translate along a path defined by pin (328). Distal coupling arm (342) is fixed to actuation band assembly (308) such that translation of band coupling body (340) along the path defined by pin (328) leads to translation of actuation band assembly (308) and trocar (302). Additionally, band coupling body (340) defines a recess (348) configured to house a portion of first and second plurality of locking members (350, 360). Recess (348) is at least partially defined by a pair of contact walls (345) configured to contact potions of first and second plurality of locking members (350, 360).

First and second plurality of locking members (350, 360) each include locking members (352, 362) having a central portion (354, 364) and a lateral portion (356, 366), respectively. Central portions (354, 364) are slidably disposed on pin (328) while lateral portions (356, 366) extend into recess (348) of band coupling body (340). Engagement arms (326) are positioned above and extend laterally across pin (328) to house central portion (354, 364) of locking members (352, 362), respectively. As best seen in FIG. 44A, when first and second plurality of locking members (350, 360) are in the locked position, bias member (370) pushes central portions (354, 364) away from each other. With central portions (354, 364) biased away from each other, a frictional breaking force is provided to help maintain longitudinal position of band coupling body (340).

Figure 44C:
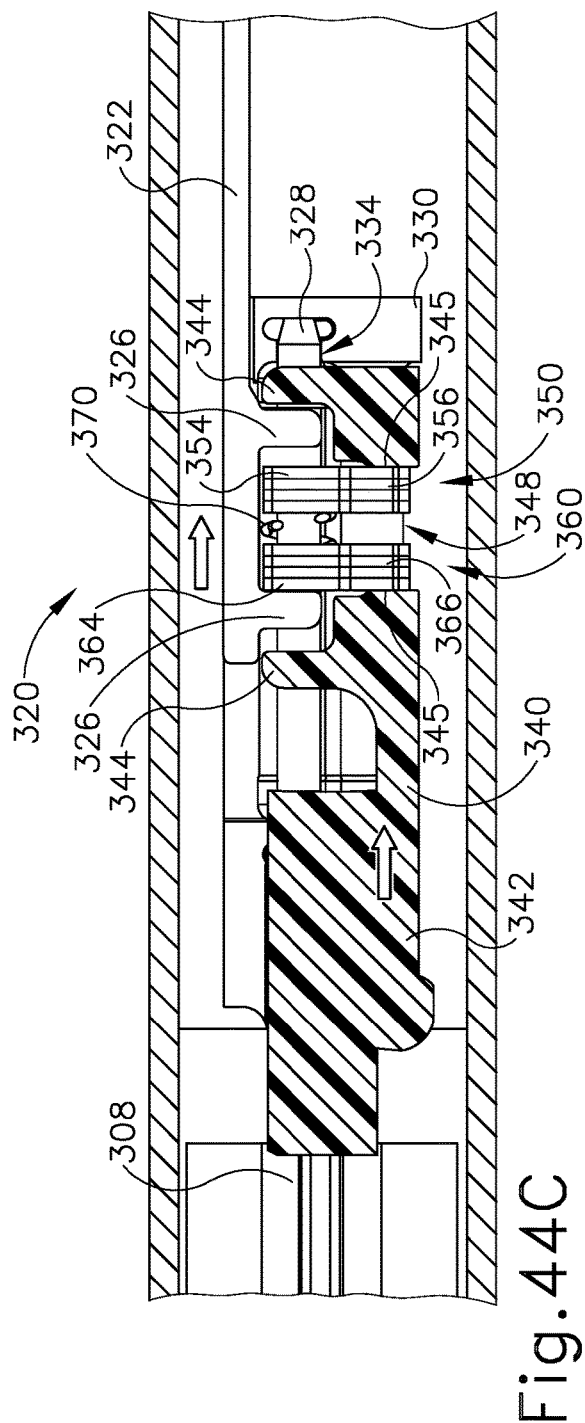
FIG. 44C depicts a cross-sectional view of the longitudinal locking assembly of FIG. 38, taken along line 44-44 of FIG. 38, where the longitudinal locking assembly is in the unlocked configuration and the drive arm of FIG. 33 is in a third longitudinal position.

FIGS. 44A-44D show exemplary use of longitudinal locking system (320). FIG. 44A shows longitudinal locking system (320) in the locked position while drive arm (322) and band coupling body (340) are in a first longitudinal position. As described above, a clinician may activate motor (118) with control rocker (112) while closure trigger (32) is in the non-actuated pivotal position.

Motor (118) may longitudinally drive longitudinal drive member (86) and intermediate firing shaft (226), as shown in FIG. 44B, which in turn is engaged with drive arm (322) via clutch assembly (500) according to the description above. One engagement arm (326) of drive arm (322) may abut against either first or second plurality of locking members (350, 360). In the current example, as shown in FIG. 44B, drive arm (322) is being actuated in the proximal direction, so a distal engagement arm (326) is abutting against second plurality of locking members (360). If drive arm (322) were being actuated in the distal direction, a proximal engagement arm (326) would abut against first plurality of locking members (350) to obtain similar results. With distal engagement arm (326) abutting against second plurality of locking members (360), first and second plurality of locking members (350, 360) may compress bias member (370) such that central portions (354, 364) reduce the amount of frictional breaking force between pin (328) and band coupling body (340).

Figure 44D:
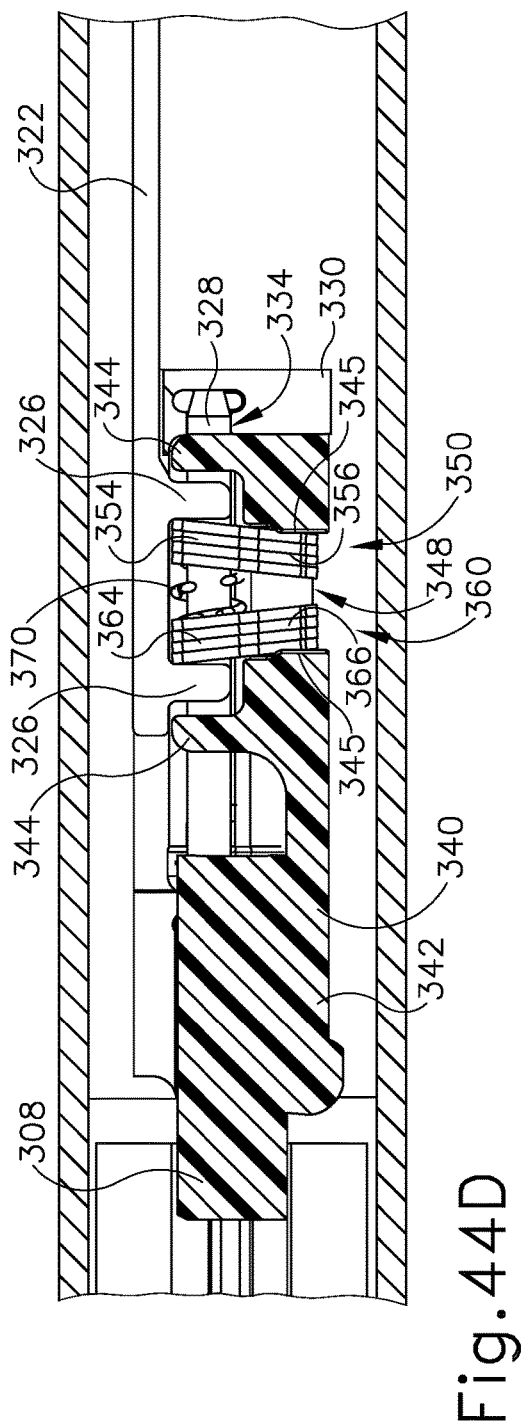
FIG. 44D depicts a cross-sectional view of the longitudinal locking assembly of FIG. 38, taken along line 44-44 of FIG. 38, where the longitudinal locking assembly is in the locked configuration and the drive arm of FIG. 33 is in the third longitudinal position.
Figure 45:
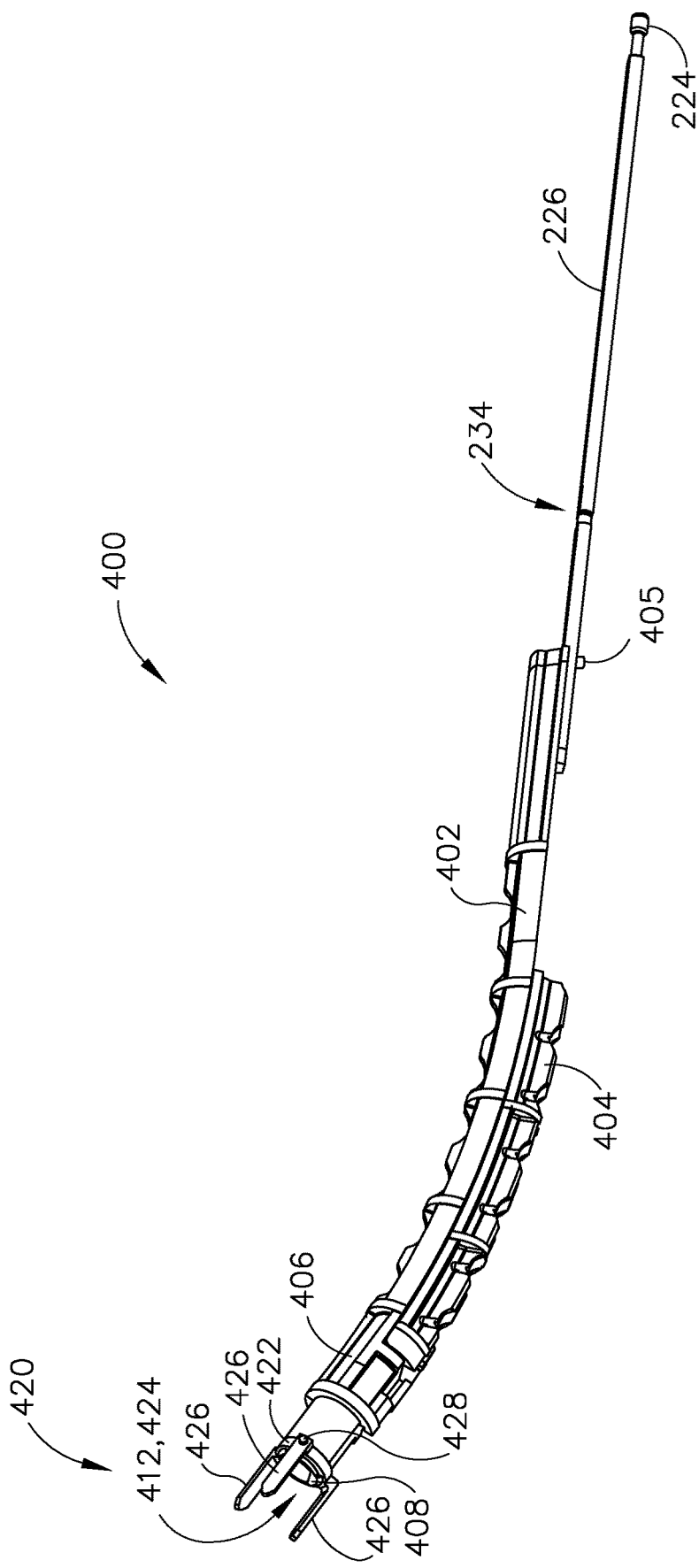
FIG. 45 depicts a perspective view of a reciprocating drive assembly of the shaft assembly of FIG. 11.
Figure 46:
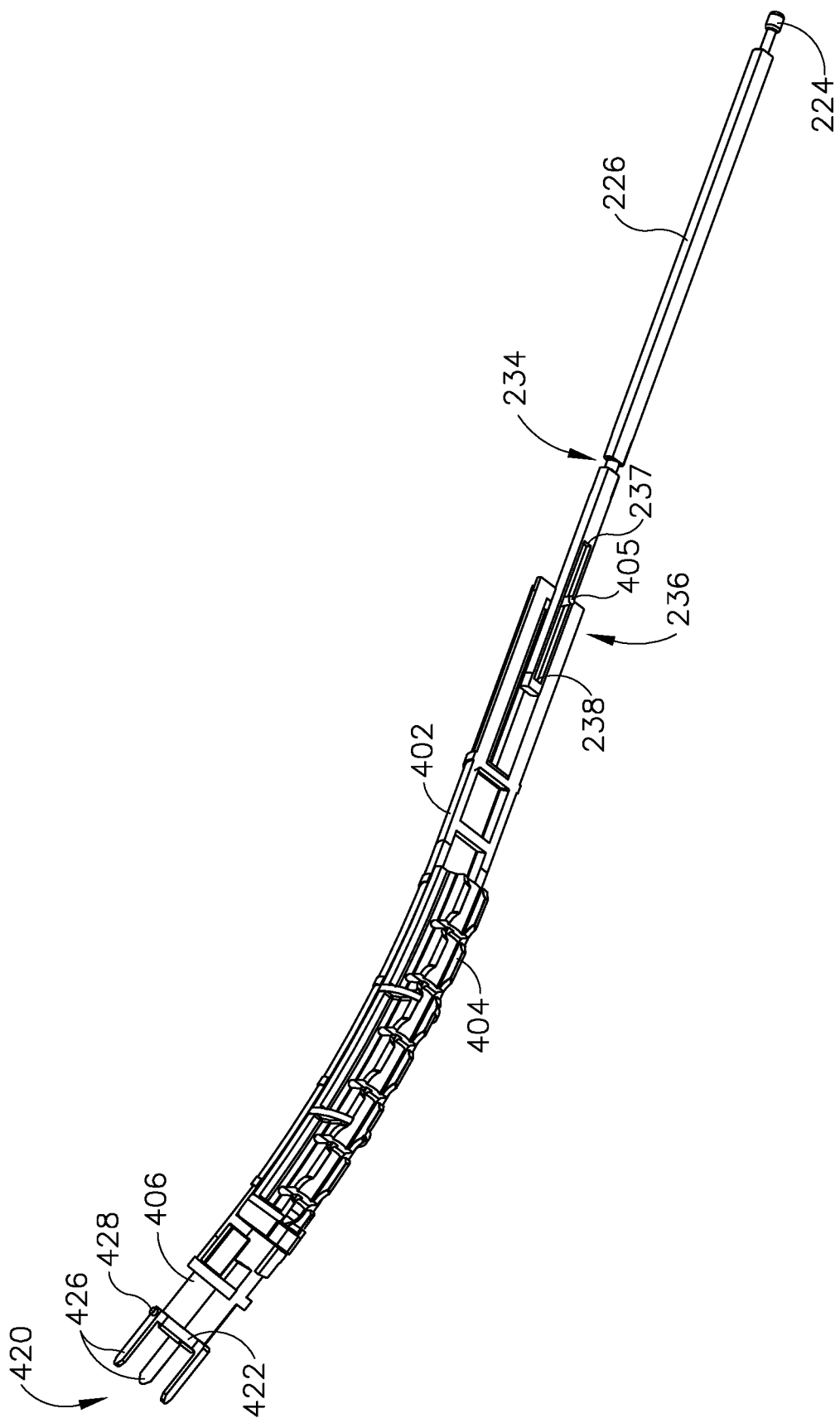
FIG. 46 depicts another perspective view of the reciprocating drive assembly of FIG. 45.

The reduction in frictional breaking force may allow for drive arm (322) to actuate first and second plurality of locking members (350, 360), such that lateral portions (356, 366) of locking members (352, 362) may drive band coupling body (340), actuation band assembly (308), and trocar (302) in the proximal direction as well, as shown in FIG. 44C. In particular, lateral portions (356, 366) may abut against contact walls (345) of band coupling body (340) to drive band coupling body (340). When motor (118) stops actuating drive arm (322) in accordance with the description above, distal engagement arm (326) may stop abutting against central portions (364) of second plurality of locking members (360). As a result, as shown in FIG. 44D, biasing member (370) may once again space first and second plurality of locking members (350, 360) away from each other to provide sufficient frictional breaking force in the locked position.

F. Exemplary Reciprocating Drive Assembly of Shaft Assembly

As mentioned above, reciprocating drive assembly (400) sequentially actuates outer staple driver (750), inner staple driver (770), and blade assembly (710) to independently fire a first annular row of staples, a second annular row of staples, and then blade member (712) to sever excess tissue. FIGS. 45-48 show reciprocating drive assembly (400).

Reciprocating drive assembly (400) includes a first flexible spine portion (402), a second flexible spine portion (404), and a driving member (420). First flexible spine portion (402) and second flexible spine portion (404) couple together to form a pathway for slidably housing trocar assembly (300). First flexible spine portion (402) and second flexible spine portion (404) are also slidably housed within outer sheath (240). First flexible spine portion (402) and second flexible spine portion (404) are sufficiently flexible to bend in response to a clinician bending the longitudinal profile of outer sheath (240) as described above.

The proximal end of first flexible spine portion (402) includes drive pin (405) housed within distal slot (236) of intermediate firing shaft (226). As described above, intermediate firing shaft (226) is configured to drive reciprocating drive assembly (400) by contact between advancing surface (237) or retracting surface (238) with drive pin (405). While in the current example, interaction between drive pin (405) and intermediate firing shaft (226) drive reciprocating drive assembly (400), any other suitable means may be used as would be apparent to one having ordinary skill in the art in view of the teachings herein.

Figure 48:
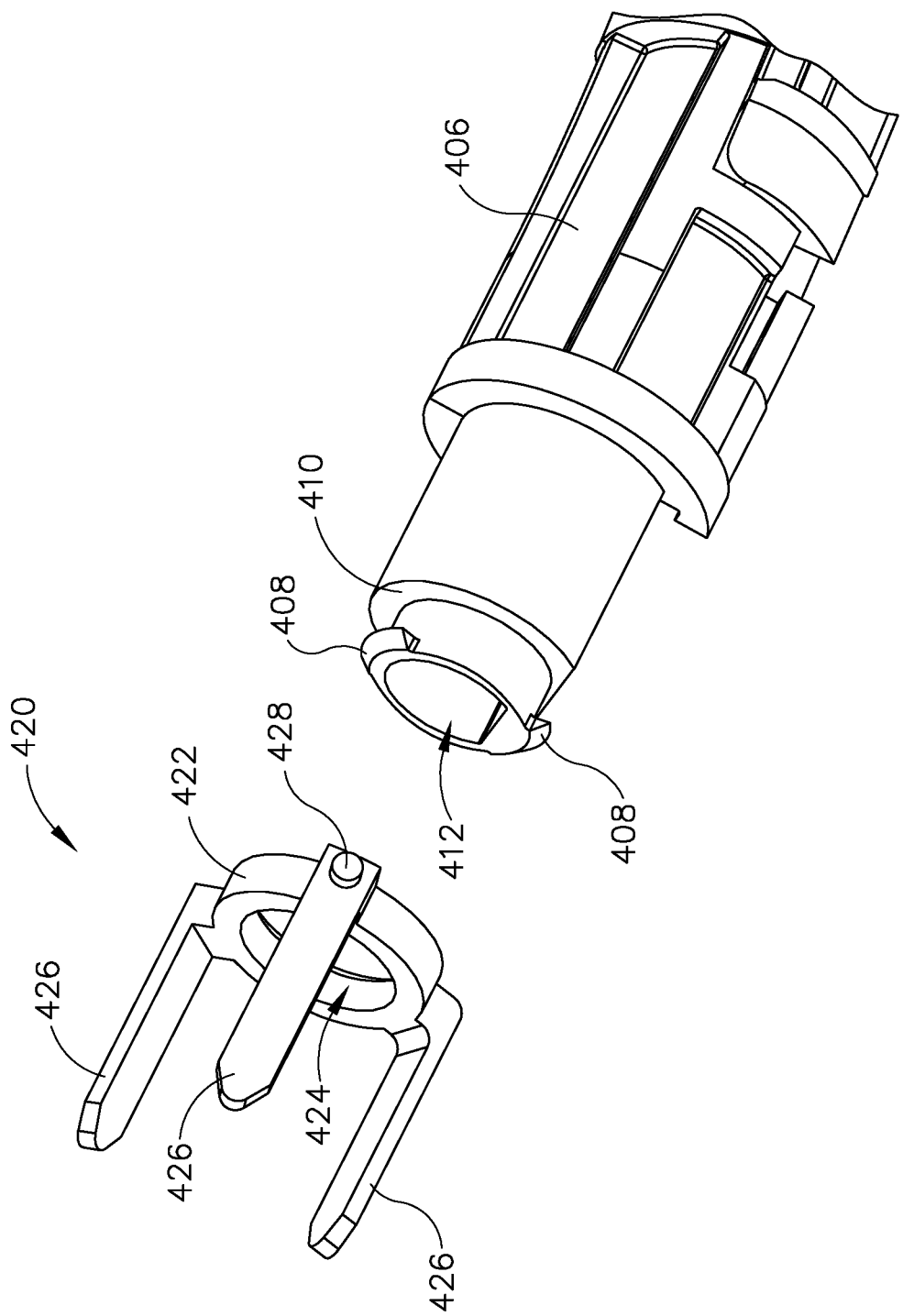
FIG. 48 depicts an exploded perspective view of a distal end of the reciprocating drive assembly of FIG. 45.

The distal end of first flexible spine portion (402) includes a trocar sheath (406). Trocar sheath (406) defines a trocar pathway (412) that may further slidably house trocar (302). As best seen in FIG. 48, the distal end of trocar sheath (406) includes a pair of tabs (408) and a distally presented annular face (410). Tabs (408) and distally presented annular face (410) are configured to rotatably couple with driving member (420) such that driving member (420) may rotate about the longitudinal axis defined by trocar sheath (406), yet also allowing trocar sheath (406) to actuate driving member (420) in response to movement of intermediate firing shaft (226) in accordance with the description above.

Driving member (420) includes a ring (422) defining an opening (424), with three driving forks (426) distally extending from ring (422). Ring (422) may be housed between tabs (408) and distally presented annular face (410) to rotatably couple driving member (420) with trocar sheath (406). As will be described in greater detail below, driving forks (426) may selectively drive corresponding firing legs (732, 754, 774) via interaction with corresponding drive couples (734, 756, 776) of blade assembly (710), outer staple driver (750), and inner staple driver sections (780), respectively. Additionally, one driving fork (426) includes a guide pin (428) extending radially outward from ring (422). As will be described in greater detail below, guide pin (428) is operable travel through drive assembly pathway (380) defined by outer sheath (240) and distal housing (260) to rotationally align driving forks (426) to drive outer staple driver (750), inner staple driver assembly (770), or blade assembly (710).

G. Exemplary Use of Interchangeable Circular Stapler Attachment

Figure 49B:
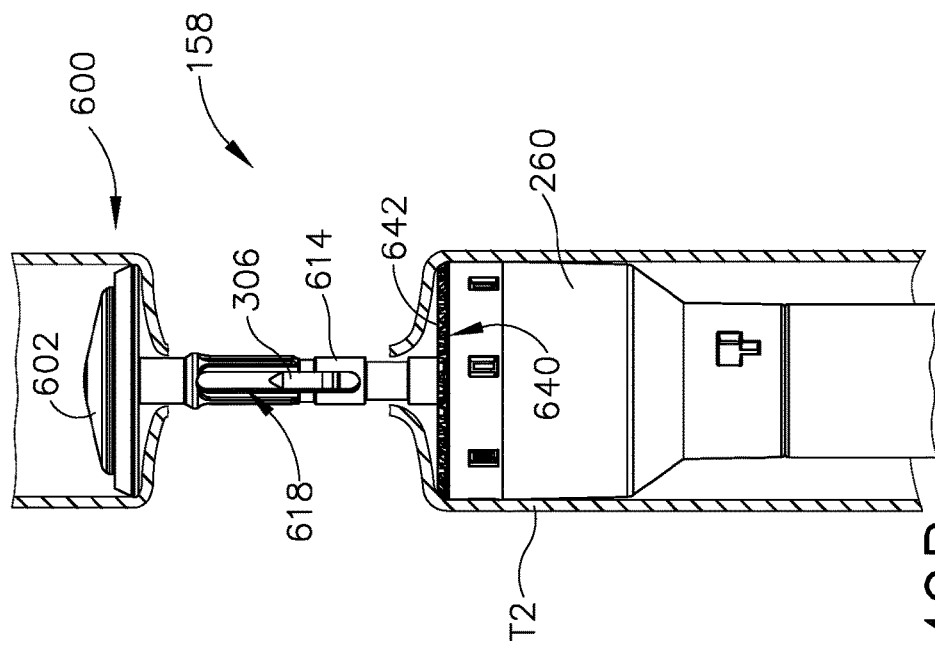
FIG. 49B depicts a side elevation view of a portion of the anvil assembly of FIG. 10 inserted within one anatomical passageway of a patient, and a portion of the shaft assembly of FIG. 11 inserted within a second anatomical passageway, where the trocar assembly of FIG. 37 is attached to the anvil assembly, and where the anvil assembly is in a first position.
Figure 49A:
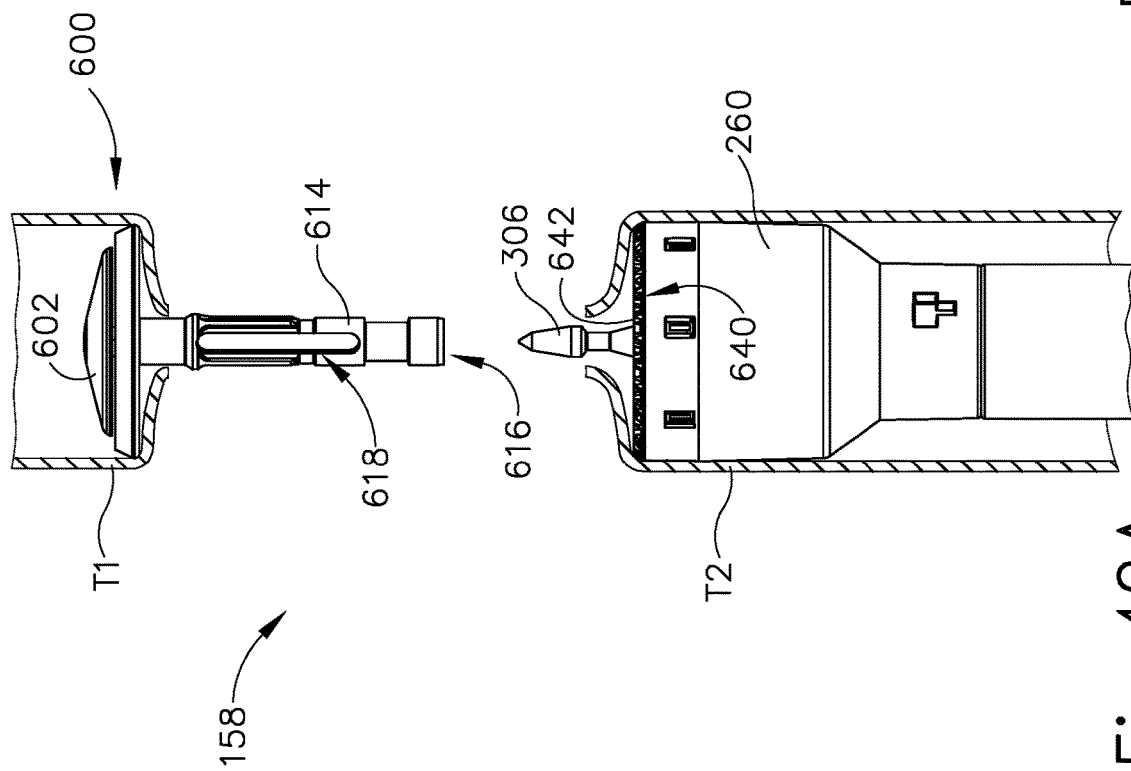
FIG. 49A depicts a side elevation view of a portion of the anvil assembly of FIG. 10 inserted within one anatomical passageway of a patient, and a portion of the shaft assembly of FIG. 11 inserted within a second anatomical passageway, where the shaft assembly and the anvil assembly are aligned in preparation of coupling with each other.

FIGS. 49A-51I show interchangeable circular stapler attachment (150) and handle assembly (11) being used to perform an end-to-end anastomosis. First, FIGS. 49A-49C show trocar (302) coupling with and retracting anvil (600) to compress tissue from ends of a first tubular anatomical structure (T1) and a second tubular anatomical structure (T2).

As shown in FIG. 49A, anvil (600) is positioned in first tubular anatomical structure (T1) while outer sheath (240) and distal housing (260) are positioned in second tubular anatomical structure (T2). In versions where tubular anatomical structures (T1, T2) comprise sections of a patient's colon, outer sheath (240) and distal housing (260) may be inserted via the patient's rectum. It should also be understood that the procedure depicted in FIGS. 49A-51I is an open surgical procedure, though the procedure may instead be performed laparoscopically. Various suitable ways in which interchangeable circular stapler attachment (150) may be used to form an anastomosis in a laparoscopic procedure will be apparent to those of ordinary skill in the art in view of the teachings herein.

As shown in FIG. 49A, anvil (600) is positioned in first tubular anatomical structure (T1) such that shank (614) protrudes from the open severed end of first tubular anatomical structure (T1). A purse-string suture (not shown) is provided about a mid-region of shank (614) to generally secure the position of anvil (600) in first tubular anatomical structure (T1). Similarly, distal housing (260) is positioned in second tubular anatomical structure (T2) such that trocar (302) protrudes from the open severed end of second tubular anatomical structure (T2). A purse-string suture (not shown) is provided about shaft (304) to generally secure the position of distal housing (260) in second tubular anatomical structure (T2).

Next, anvil (600) is secured to trocar (302) by inserting trocar (302) into bore (616) as shown in FIG. 49B. As mentioned above, anvil (600) may secure to trocar (302) by any suitable means as would be apparent to one having ordinary skill in the art in view of the teachings herein, such as a latch snap fitting with head (306) of trocar (302). Next, the clinician may then retract trocar (302) and anvil (600) by activated control rocker (112) while closure trigger (32) is in the non-actuated pivotal position (as shown in FIG. 4A). As described above, trocar assembly (330) may be engaged with intermediate firing shaft (226) via clutch assembly (500) so that intermediate firing shaft (226) drives trocar assembly (330) independently of reciprocating drive assembly (400). Additionally, longitudinal locking assembly (320) may function in accordance with the description above.

Figure 49C:
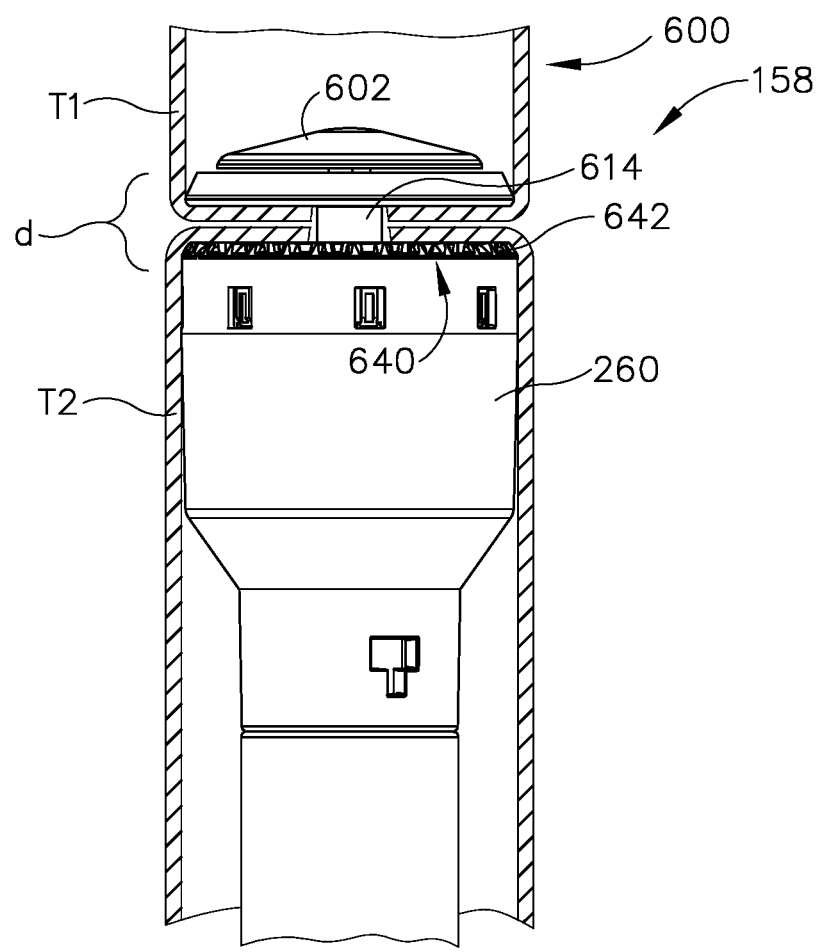
FIG. 49C depicts a side elevation view of a portion of the anvil assembly of FIG. 10 inserted within one anatomical passageway of a patient, and a portion of the shaft assembly of FIG. 11 inserted within a second anatomical passageway, where the trocar assembly of FIG. 37 is attached to the anvil assembly, and where the anvil assembly is moved to a second position to capture portions of the first anatomical passageway and the second anatomical passageway between the anvil assembly and the shaft assembly.

As shown in FIG. 49C, this proximal retraction of trocar (302) and anvil (600) compresses the tissue of tubular anatomical structures (T1, T2) between surfaces proximal surface (604) of anvil (600) and distally presented deck surface (642) of deck member (640). As described above, encoder (115) may communicate with control circuit (117) the longitudinal position of intermediate shaft assembly (226). Control circuit (117) may use the longitudinal position of intermediate shaft assembly (226) to determine a gap distance (d) between proximal surface (604) and distally presented deck surface (642). Control circuit (117) may then communicate this gap distance (d) to the clinician via graphical user interface (116). Control circuit (117) may further calculate whether this gap distance is sufficient to perform an end-to-end anastomosis, and communicate that information to the clinician. Therefore, the clinician may adjust the gap distance (d) via control rocker (112) to acquire an appropriate gap distance (d), and confirm the appropriate gap distance (d) via graphical user interface (116).

Once the clinician has appropriately set the gap distance (d) via graphical user interface (116), the clinician may pivot closure trigger (32) from the non-actuated pivotal position (as shown in FIG. 4A) to the actuated pivotal position (as shown in FIG. 4B). As described above, clutch assembly (500) then disengages trocar assembly (300) from intermediate firing shaft (226) so that intermediate firing shaft (226)

may actuate reciprocating drive assembly (400). At this point, a clinician may press firing trigger (33) to start the firing sequence.

As mentioned above, camming face (245) of drive assembly pathway (380) is configured to properly orient driving member (420) of reciprocating drive assembly (400) based on a longitudinal position of reciprocating driver assembly (400) to sequentially drive outer staple driver (750), inner staple driver assembly (770), and blade assembly (710). FIG. 50A shows driving member (420) in an initial pre-firing position, or a first proximal position. Control circuit (117) may store the first proximal position for purposes of instructing motor (118) to properly drive reciprocating drive assembly (400) in accordance with the description herein. Guide pin (428) of driving member (420) is initially located within first stapling pathway (380) and distal relative to camming face (245) in the first proximal position. Driving forks (426) are aligned with corresponding drive couplers (756) of outer staple driver (750).

Figure 51A:
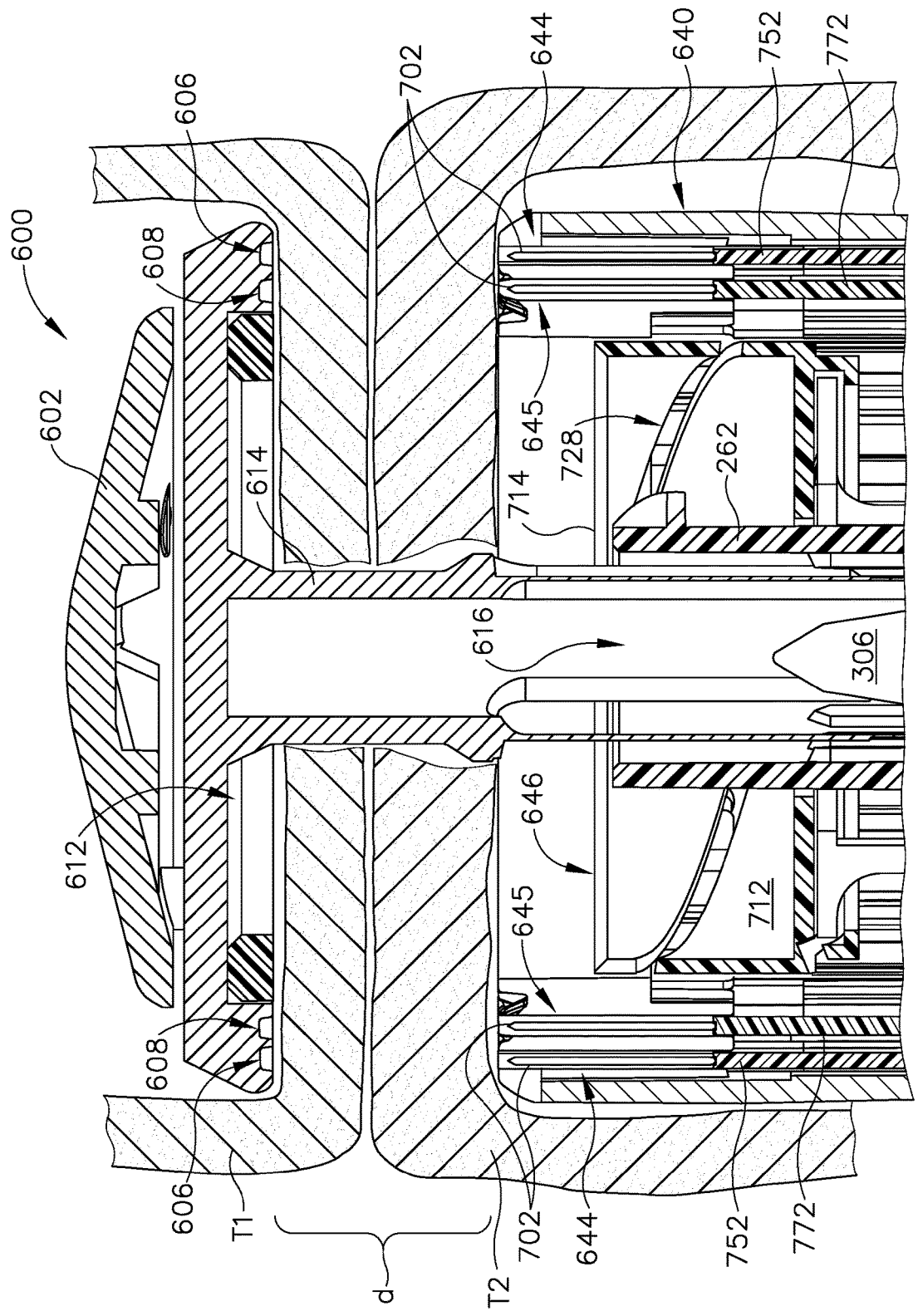
FIG. 51A depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly in preparation to form an anastomosis.

Additionally, FIG. 51A shows tissue from tubular anatomical structures (T1, T2) between anvil (600) and deck member (640) in the pre-fired position. As can be seen in FIG. 51A, staples (702) are retained within outer and inner concentric annular array of staple openings (644, 645) in the pre-fired position; while staples drivers (752, 772) are slidably disposed within concentric annular array of staple openings (644, 645), respectively, under corresponding staples (702). Additionally, staples (702) are aligned with both outer and inner annular array of staple forming pockets (606, 608).

Figure 50D:
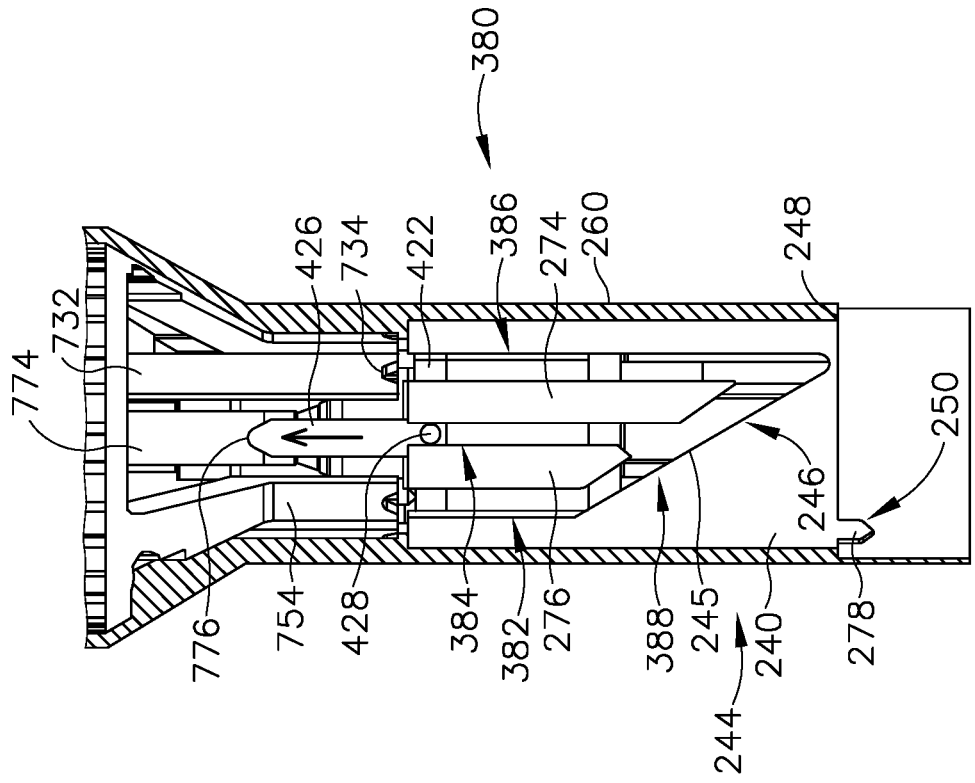
FIG. 50D depicts an elevational side view of a portion of the shaft assembly of FIG. 11 and the end effector of FIG. 11, with certain portions omitted for clarity, where the driving member of FIG. 50A is in the second rotational position aligned with the inner staple driver assembly of FIG. 18, where the inner staple driver assembly is in a fired position.
Figure 51B:
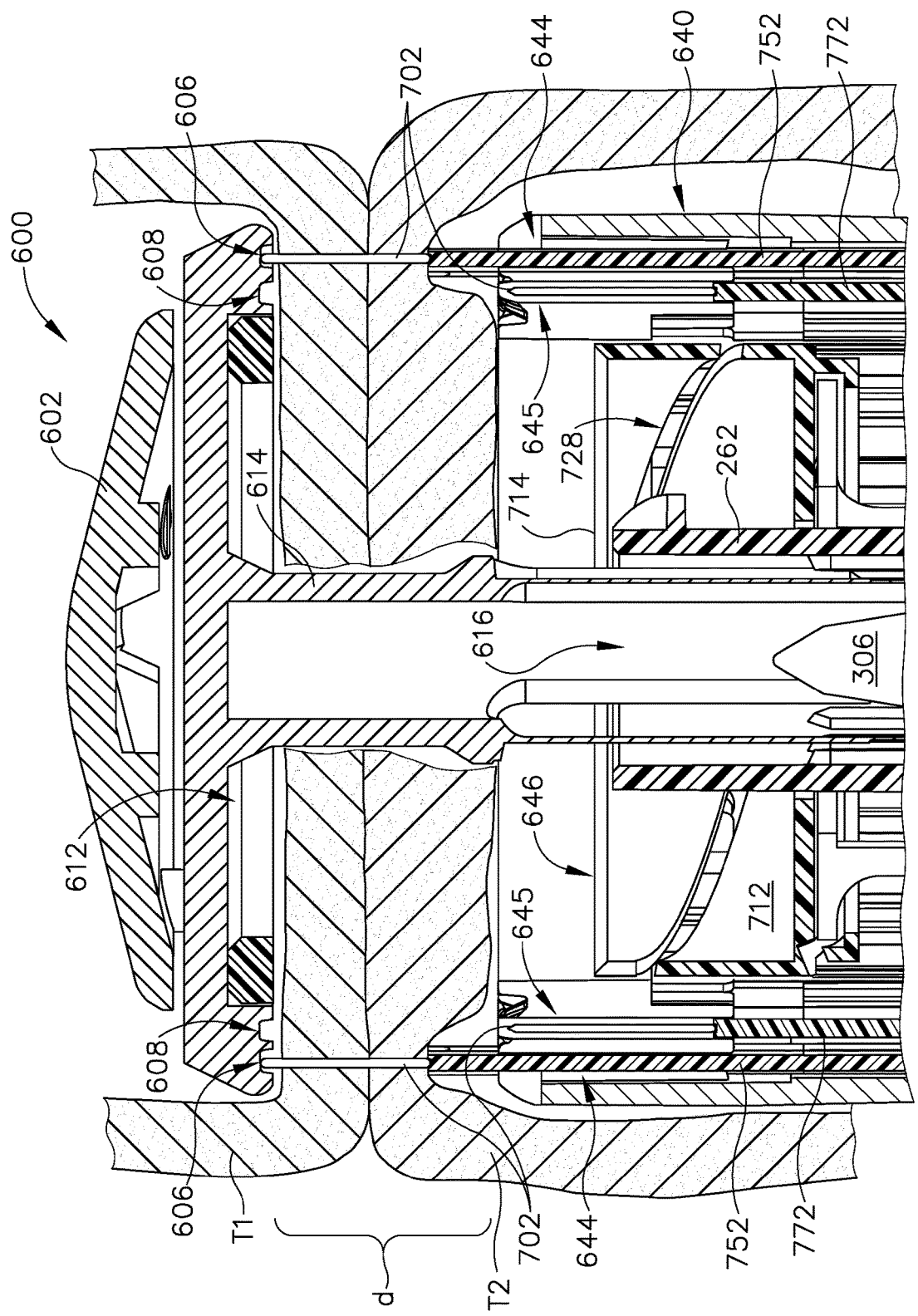
FIG. 51B depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the outer staple driver of FIG. 17 is in the fired position.

After a clinician actuates firing trigger (33), control circuit (117) may instruct motor (118) to actuate intermediate drive shaft (226) to drive reciprocating drive assembly (400) from the first proximal position to a first distal position within first stapling pathway (382), as shown in FIG. 50B. Guide pin (428) is still within first stapling pathway (382) but in the first distal position. Driving forks (426) actuate corresponding firing legs (754) of outer staple driver (750) distally. As can be seen in FIG. 51B, staple drivers (752) are actuated distally in response to driving forks (426) actuating from the first proximal position to the first distal position. Staple drivers (752) of outer staple driver (750) drive staples (702) through outer concentric annular array of staple opening (644) into outer annular array of staple forming pockets (606), thereby stapling tissue from tubular anatomical structures (T1, T2) between anvil (600) and deck member (640) together. At this point, staples (702) within inner concentric annular array of staple opening (645) as well as blade assembly have yet to be fired.

Figure 50C:
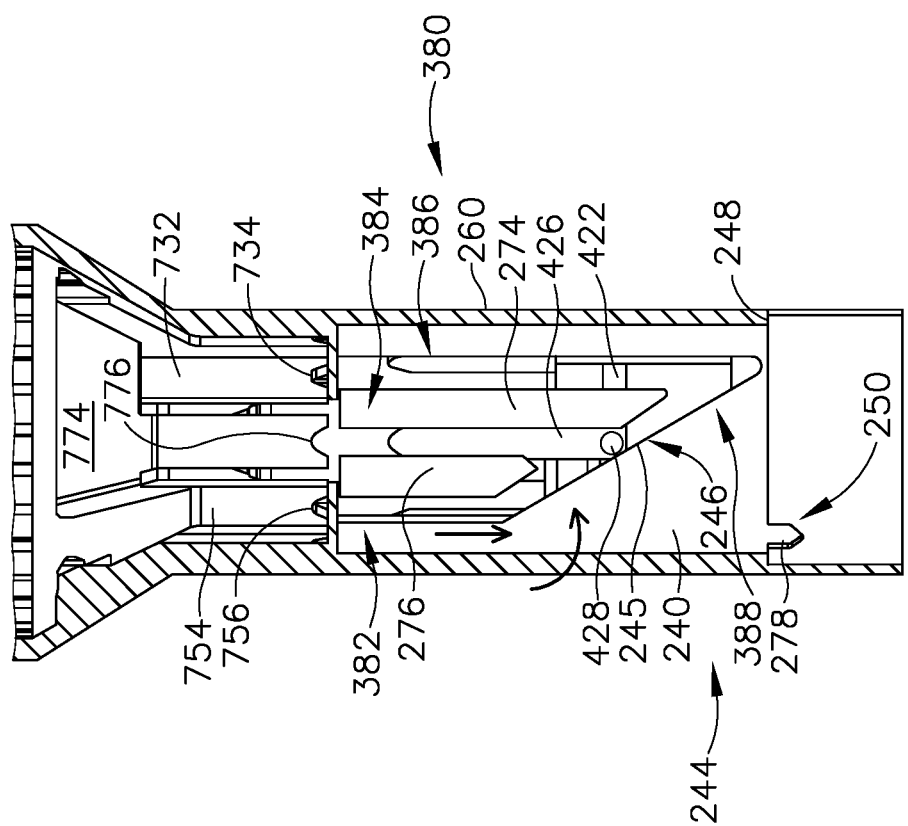
FIG. 50C depicts an elevational side view of a portion of the shaft assembly of FIG. 11 and the end effector of FIG. 11, with certain portions omitted for clarity, where the driving member of FIG. 50A is in a second rotational position aligned with the inner staple driver assembly of FIG. 18, where the inner staple driver assembly is in a pre-fired position.
Figure 51C:
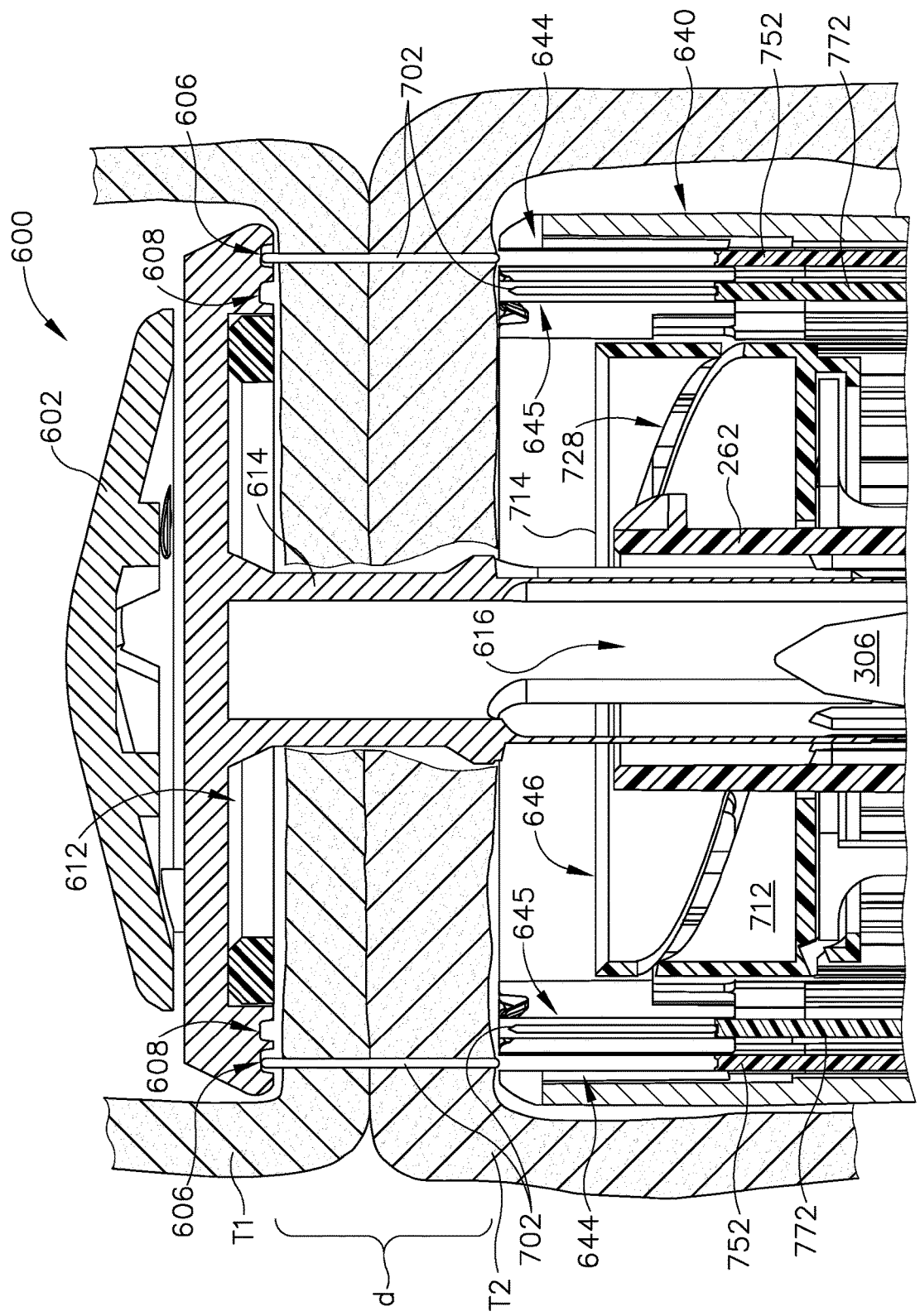
FIG. 51C depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the outer staple driver of FIG. 17 has driven staples through the first and second anatomical passageways to help form an anastomosis.

Next, as shown in FIG. 50C, control circuit (117) may instruct motor (118) to actuate intermediate drive shaft (226) to drive reciprocating drive assembly (400) from the first distal position to a second proximal position. As reciprocating drive assembly (400) translates from the first distal position to the second proximal position, guide pin (428) translates through first stapling pathway (382), into connection channel (388). While guide pin (428) translates through connection channel (388), guide pin (428) contacts camming face (245). As described above, driving member (420) is rotatably coupled with trocar sheath (406). Therefore, contact between camming face (245) and guide pin (428) rotates driving member (420) relative to trocar sheath (406) such that driving forks (426) are aligned with second stapling pathway (384) and drive coupler (776) of corresponding firing legs (774) of inner staple driver sections (280). As seen in FIG. 51C, staple driver (752) of outer staple driver (750) may return to their non-fired position within deck member (640).

At this point, control circuit (117) may instruct motor (118) to rest for a predetermined amount of time to let recently fired staples (702) form between tubular anatomical structures (T1, T2). This may provide time for the tissue to normalize as fluids are progressively squeezed out during staple formation. However, this is merely optional.

Figure 51D:
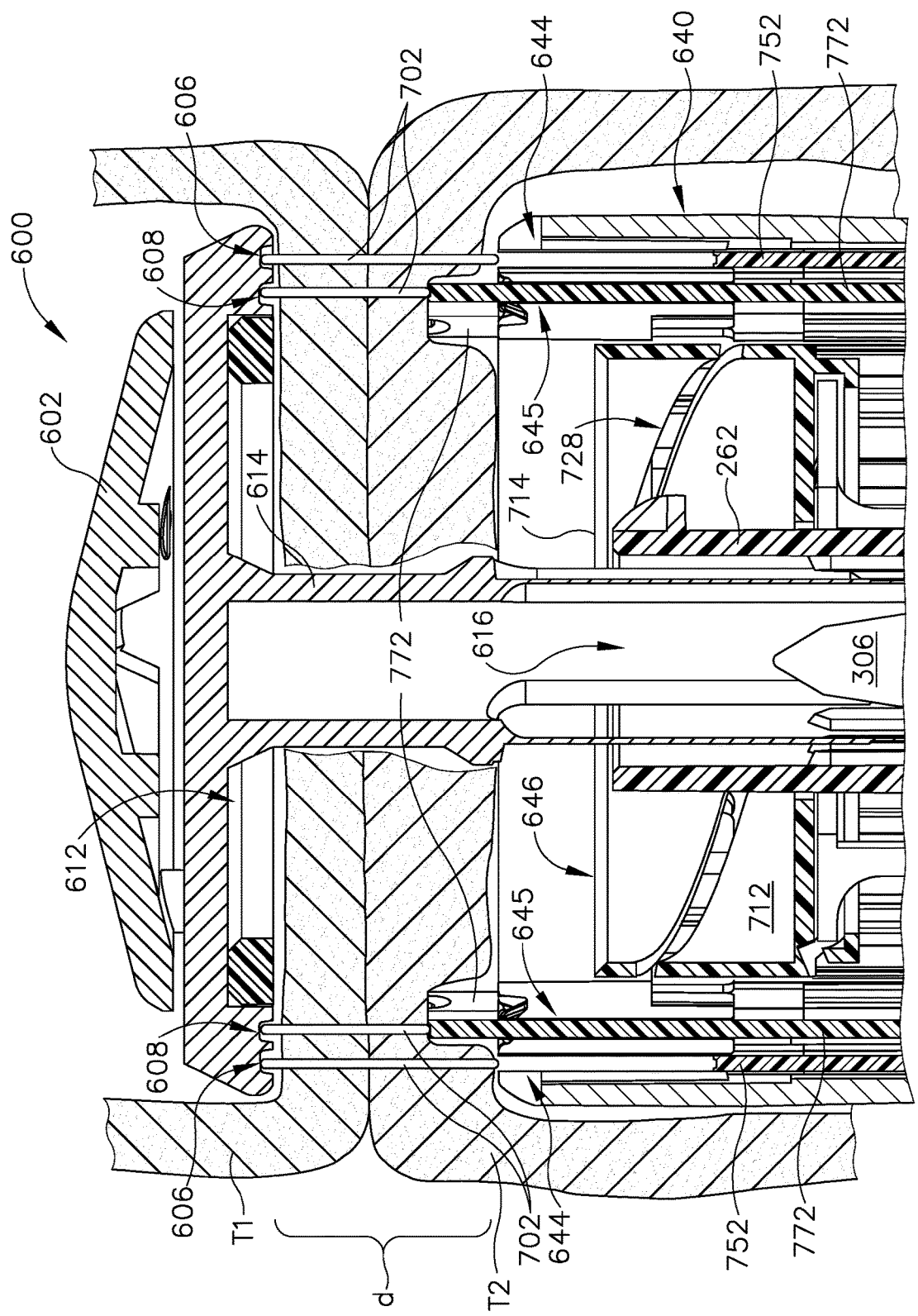
FIG. 51D depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the inner staple driver assembly of FIG. 18 is in the fired position.

Next, as in FIG. 50D, control circuit (117) may instruct motor (118) to actuate intermediate drive shaft (226) to drive reciprocating drive assembly (400) from the second proximal position to a second distal position within second stapling pathway (384). Second interior protrusion (276) includes a proximal presented chamfered edge. Therefore, if reciprocating drive assembly (400) as actuated to a position slightly distal as compared to the intended second proximal position, guide pin (428) may cam against the chamfered edge of second interior protrusion (276) to urge guide pin (428) within second stapling pathway (384) while translating toward the second distal position. Driving forks (426) actuate corresponding firing legs (774) of inner staple driver assembly (770) distally. As can be seen in FIG. 51D, staple drivers (772) are actuated distally in response to driving forks (426), actuating from the second proximal position to the second distal position. Staple drivers (772) of inner staple drive assembly (770) drive staples (702) through inner concentric annular array of staple opening (645) into inner annular array of staple forming pockets (608), thereby stapling tissue from tubular anatomical structures (T1, T2) between anvil (600) and deck member (640) together. At this point, staples (702) from both inner and outer concentric annular array of staple opening (645, 644) have been fired, yet blade assembly (710) has yet to have fired.

Next, as shown in FIG. 50E, control circuit (117) may instruct motor (118) to actuate intermediate drive shaft (226) to drive reciprocating drive assembly (400) from the second distal position to a third proximal position. As reciprocating drive assembly (400) translates from the second distal position to the third proximal position, guide pin (428) translates through second stapling pathway (384), into connection channel (388). While guide pin (428) translates through connection channel (388), guide pin (428) contacts camming face (245). As described above, driving member (420) is rotatably coupled with trocar sheath (406). Therefore, contact between camming face (245) and guide pin (428) rotates driving member (420) relative to trocar sheath (406) such that driving forks (426) are aligned with blade actuation pathway (386) and drive coupler (734) of corresponding firing legs (732) of blade assembly (710). As seen in FIG. 51E, staple drivers (772) of inner staple driver assembly (770) may return to their non-fired position within deck member (640).

At this point, control circuit (117) may instruct motor (118) to rest for a predetermined amount of time to let recently fired staples (702) form between tubular anatomical structures (T1, T2). This may provide time for the tissue to normalize as fluids are progressively squeezed out during staple formation. However, this is merely optional.

Figure 51F:
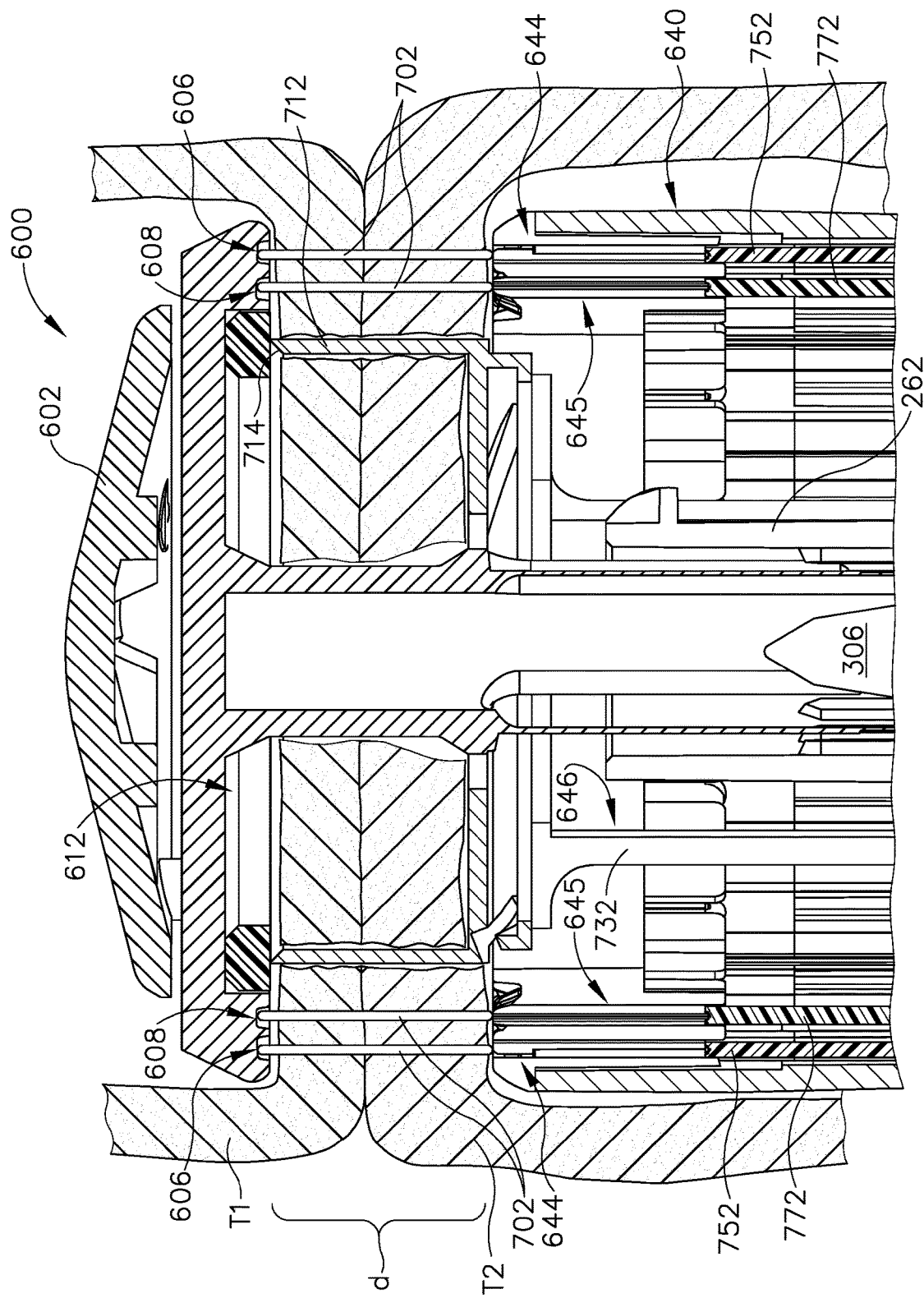
FIG. 51F depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the blade assembly of FIG. 20 is in the fired position.

Next, as shown in FIG. 50F, control circuit (117) may instruct motor (118) to actuate intermediate drive shaft (226) to drive reciprocating drive assembly (400) from the third proximal position to a third distal position within blade actuation pathway (386). Driving forks (426) actuate corresponding firing legs (732) of blade assembly (730) distally. As can be seen in FIG. 51F, blade member (712) is actuated distally in response to driving forks (426) actuating from the third proximal position to the third distal position. Distal cutting edge (714) of blade assembly (710) sever tissue from tubular anatomical structures (T1, T2) interior in relation to staples (702), thereby removing excess tissue. It should be understood that at this point, all staples (702) have been fired and blade assembly (710) has severed excess tissue.

Figure 50G:
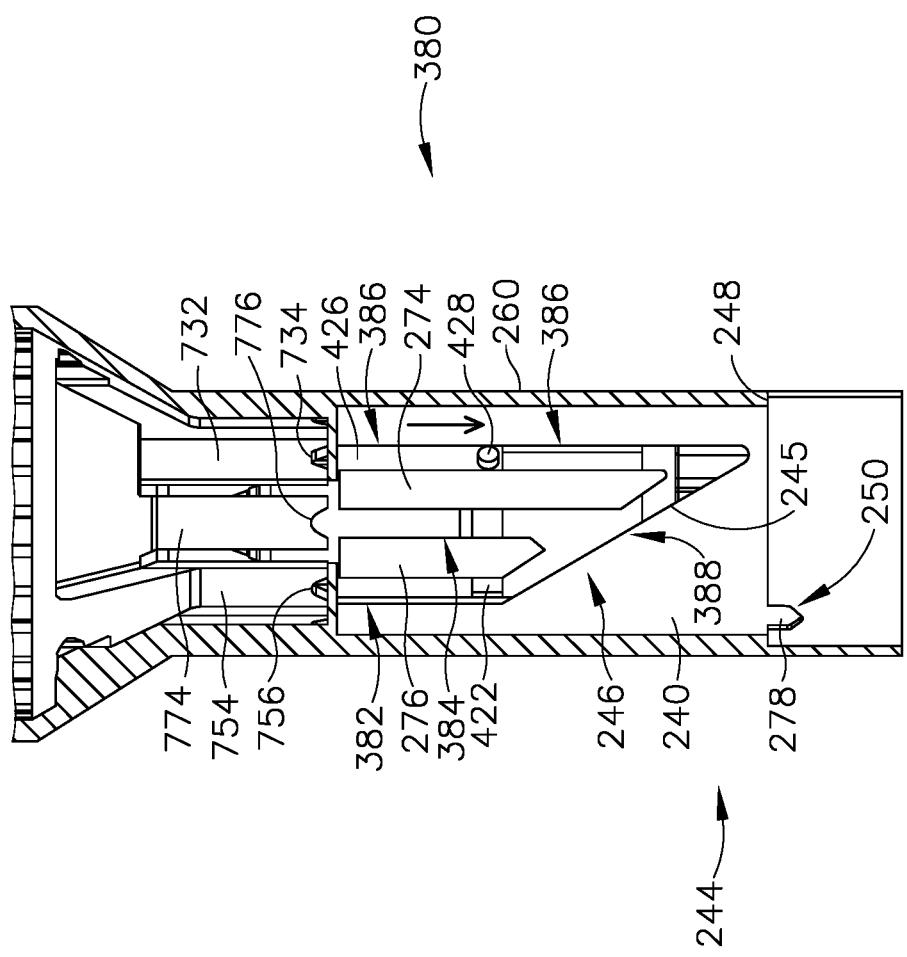
FIG. 50G depicts an elevational side view of a portion of the shaft assembly of FIG. 11 and the end effector of FIG. 11, with certain portions omitted for clarity, where the driving member of FIG. 50A is in the third rotational position aligned with the blade assembly of FIG. 20, where the blade assembly is in a post-fired position.
Figure 51G:
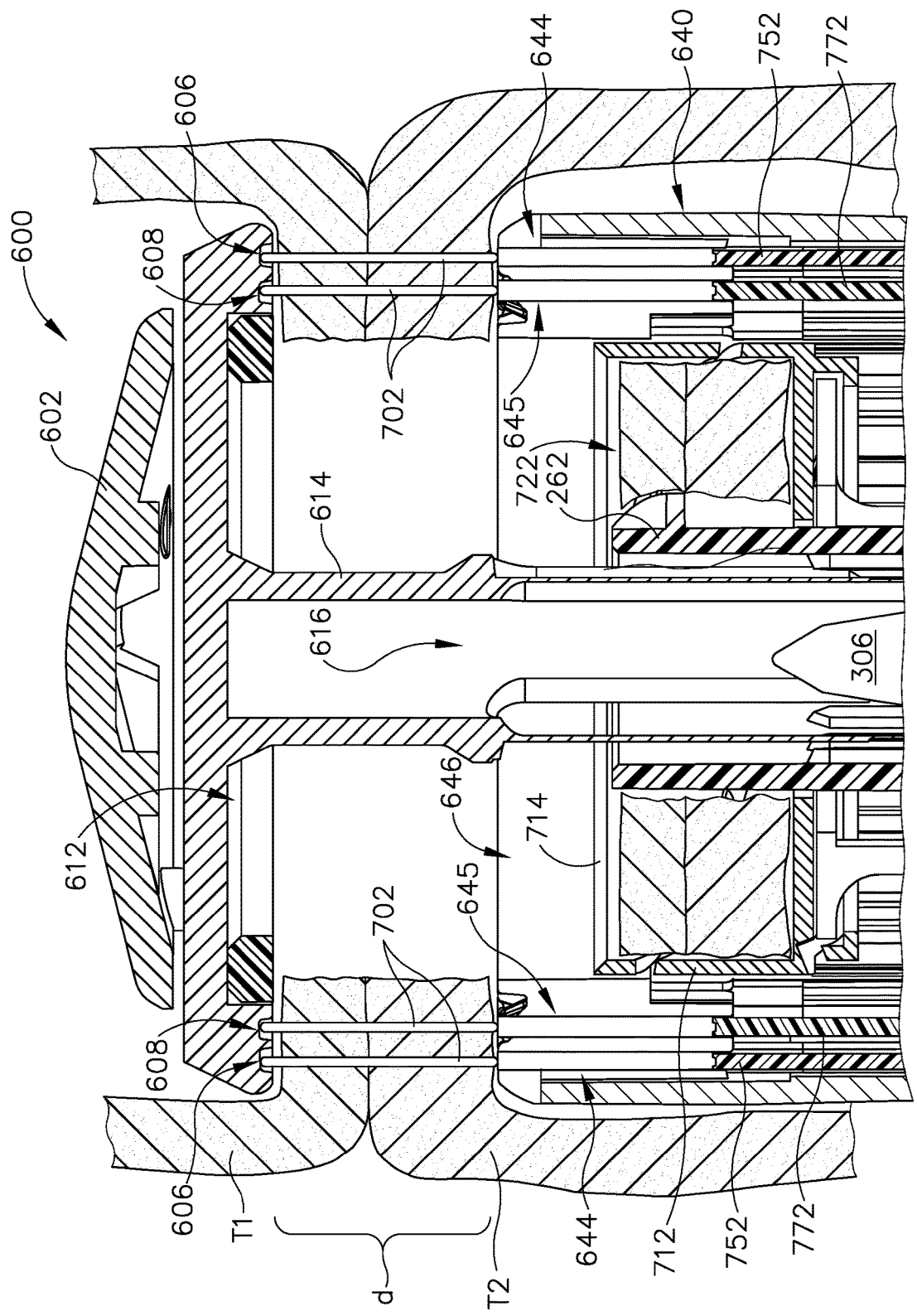
FIG. 51G depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where tissue from the first and second anatomical passageways are captured between the anvil assembly and the shaft assembly, where the blade assembly of FIG. 20 severed and removed tissue within the interior of the driven staples of FIG. 51C and FIG. 51E.

Next, as shown in FIG. 50G, control circuit (117) may instruct motor (118) to actuate intermediate drive shaft (226) to drive reciprocating drive assembly (400) from the third distal position back to the initial, first proximal position. As shown in FIG. 51G, blade assembly (710) may retract toward the pre-fired position with excess tissue within tissue cavity housing (722).

Figure 51H:
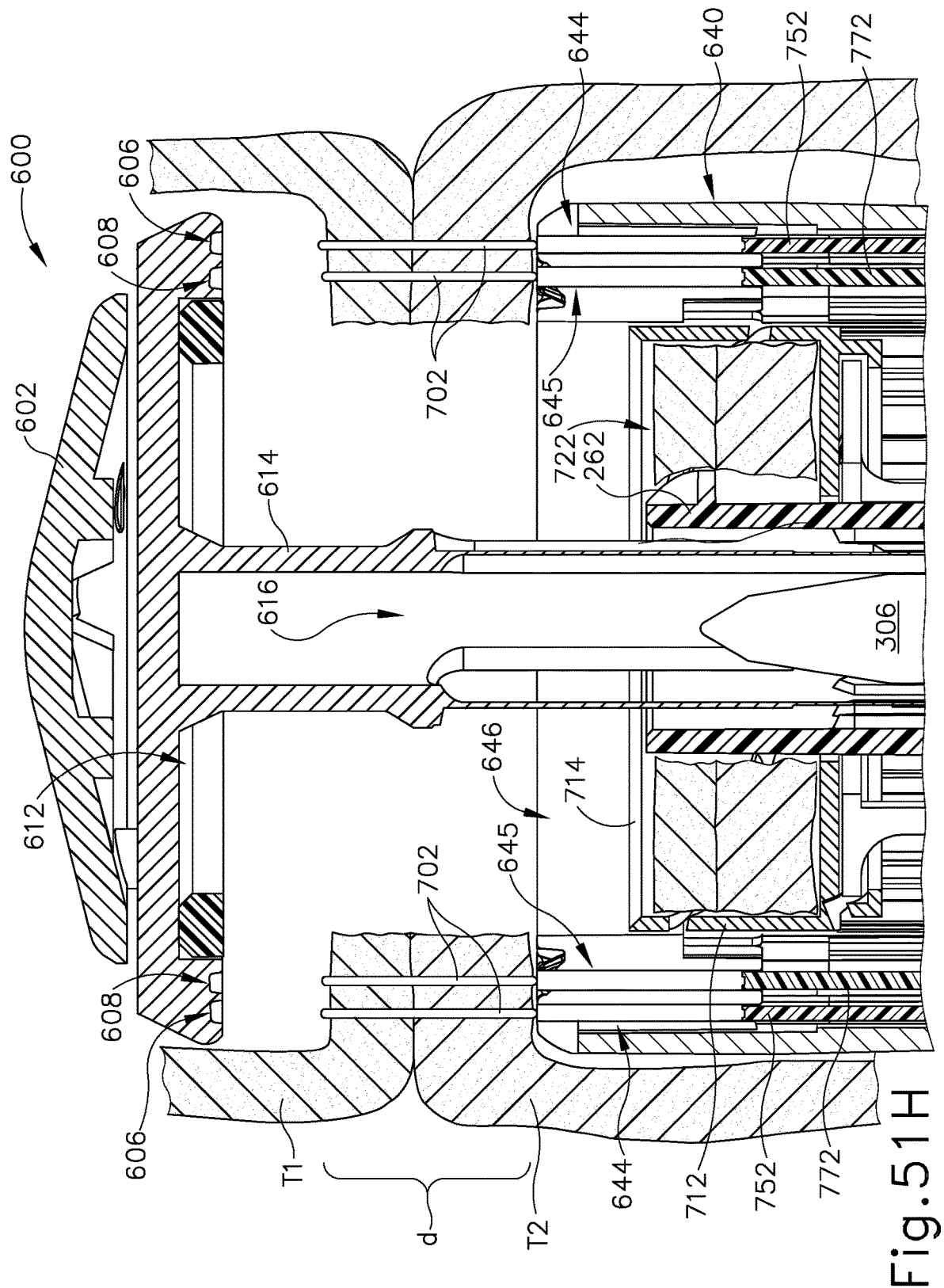
FIG. 51H depicts a cross-sectional side view of the anvil assembly of FIG. 10, taken along line 51-51 of FIG. 9, with the anvil assembly inserted within one anatomical passageway of a patient, and a portion of the shaft assembly of FIG. 11 inserted within a second anatomical passageway of a patient, where the anvil assembly is actuated distally from the newly stapled and severed tissue.
Figure 51I:
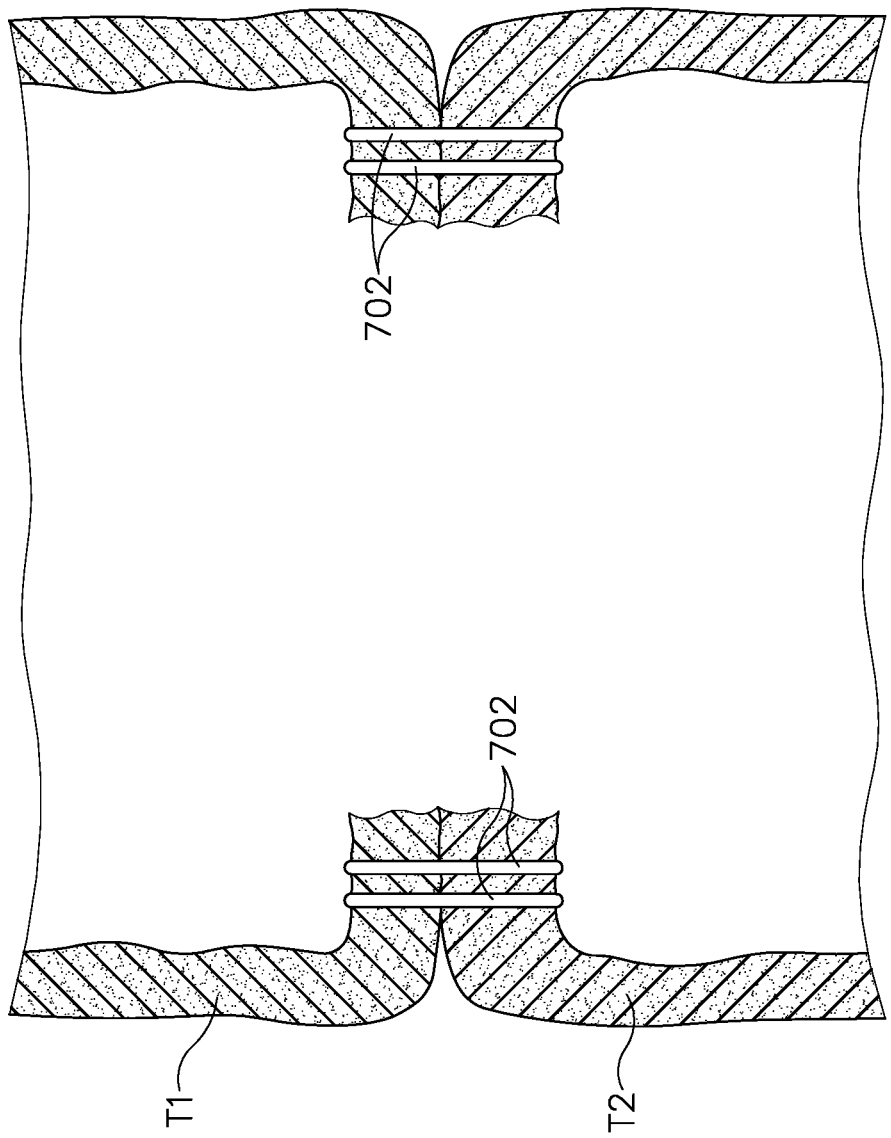
FIG. 51I depicts a cross sectional side view of the newly formed anatomical passageway, with the anvil assembly of FIG. 10 and the shaft assembly of FIG. 11 removed, leaving a newly formed anastomosis between the first anatomical passageway of a patient and the second anatomical passageway of a patient.

With intermediate drive shaft (226) back at the location required to drive reciprocating drive assembly (400) to the first proximal position, control circuit (117) may then instruct motor (118) to actuate intermediate drive shaft (226) to the position where sector flange (504) is longitudinally aligned with clutch engagement notch (324) of drive arm (322). A clinician may then then pivot closure trigger (32) from the actuated pivotal position to the non-actuated pivotal position in accordance with the teachings herein. As described above, with closure trigger (32) in the non-actuated pivotal position, clutch assembly (500) connects intermediate firing shaft (226) with trocar assembly (300). Therefore, a clinician may activate control rocker (112) to drive trocar (302) distally such that tissue of tubular anatomical structures (T1, T2) between proximal surface (604) of anvil and distally presented deck surface (642) of deck member (640) is released, as shown in FIG. 51H. Next, a clinician may remove interchangeable circular stapler attachment (150) from the surgical site, leaving a newly formed end-to-end anastomosis, as shown in FIG. 51I.

In the current example, reciprocating drive assembly (400) is configured to drive outer staple driver (750), inner staple driver assembly (770), and blade assembly (710) in sequential order independently of each other. However, it should be apparent that one having ordinary skill in the art may modify reciprocating drive assembly (400), distal outer sheath (240), distal housing (260), and end effector (158) to drive inner staple drive assembly (770) prior to driving outer staple driver (750), then drive blade assembly (710). Additionally, one having ordinary skill in the art may modify interchangeable circular stapler attachment (150) to fire either one of outer staple driver (750) and inner staple driver assembly (770) simultaneously with drive blade assembly (710) after a first row of annular staples is formed. While in the current example, staples (702) were independently driven in sequential order determined on and inner and outer annular array of staples, any other suitable sequential order may be used as would be apparent to one having ordinary skill in the art in view of the teachings herein. For example, staples (702) may be fired in circumferential sections, circumferential patterns, etc. Other, similar modifications regarding actuation of stapling and cutting assembly (700) will be apparent to one having ordinary skill in the art in view of the teachings herein.

As mentioned above, camming face (245) of drive assembly pathway is configured to properly orient driving member (420) of reciprocating drive assembly (400) based on the longitudinal position of reciprocating driver assembly (400) to align driving forks (426) with corresponding members of outer staple driver (450), inner staple driver assembly (470) and blade assembly (410). In particular, guide pin (428) of driving member (420) may travel within connecting channel (388) to rotate driving member (420) to properly orient driving member (420). In some instances, reciprocating drive assembly (400) may actuate too far proximally, thereby over rotating guide pin (428) such that guide pin (428) is not properly aligned with first stapling channel (382) or second stapling channel (384) before driving member (420) actuates outer staple driver (450) or inner stapler driver assembly (470), respectively. If this occurs, driving member (420) may be prevented from driving outer staple driver (750) or inner staple driver assembly (770) due to this misalignment. Therefore, may be desirable to prevent guide pin (428) from traveling too far within drive assembly pathway (380) such that guide pin (428) may not over rotate driving member (420) before traveling within first stapling pathway (382) or second stapling pathway (384).

FIGS. 52A-52E show an alternative drive assembly pathway (980) that may be implemented into shaft assembly (156) in replacement of drive assembly pathway (380) described above. Drive assembly pathway (980) includes a first stapling pathway (982), a second stapling pathway (984), a blade actuation pathway (986), and a connecting channel (988), which are substantially similar to first stapling pathway (382), second stapling pathway (384), and blade actuation pathway (386), and connecting channel (388), respectively, with differences described below. Therefore, first stapling pathway (982) is configured to receive guide pin (428) of driving member (420) while driving member (420) actuates outer staple driver (750). Second stapling pathway (984) is configured to receive guide pin (428) of driving member (420) while driving member (420) actuates inner staple driver assembly (770). Blade actuation pathway (986) is configured to receive guide pin (428) of driving member (420) while driving member (420) actuates blade assembly (710). Connecting channel (988) includes a camming face (945) configured to cam against guide pin (428) to rotate driving member (420) to properly align pin (428) with first stapling pathway (982), second stapling pathway (984), and blade actuation pathway (986).

Figure 52A:
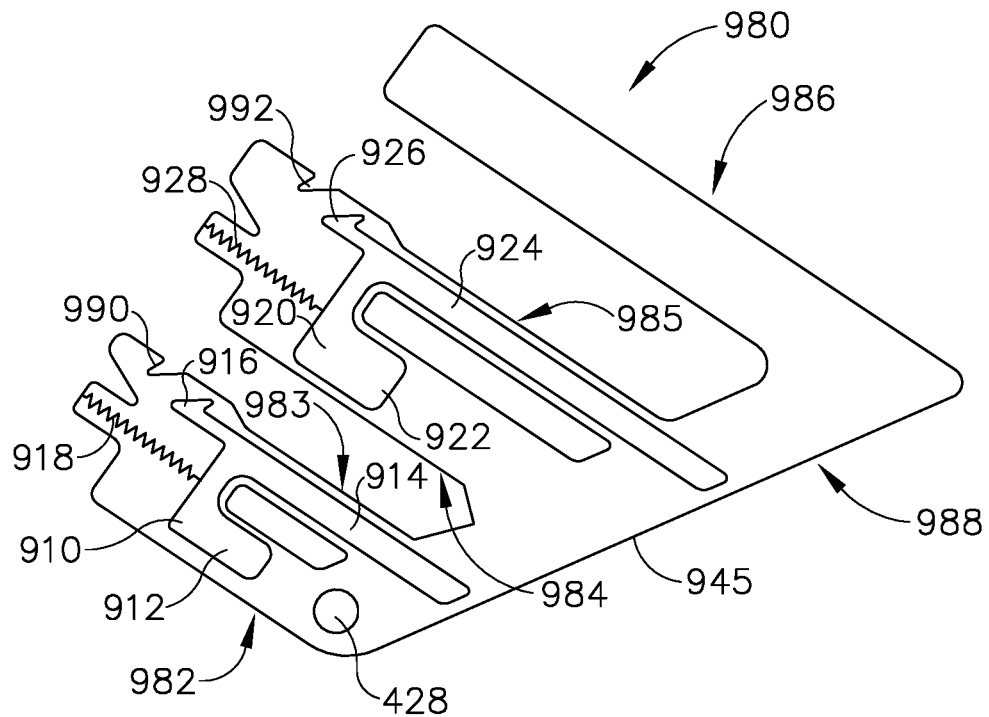
FIG. 52A depicts an elevational side view of a portion of an alternative shaft assembly, with certain portions omitted for clarity, where the driving member of FIG. 50A is in a first rotational position aligned with the outer staple driver of FIG. 17, where the outer staple driver is in a pre-fired position.

However, drive assembly pathway (980) also includes a first stop channel (983), a second stop channel (985), a first stop member (910), a second stop member (920), a first catch (990), and a second catch (992). First stop member (910) includes a camming member (912), a stopping member (912), a latch (916), and a bias member (918). Camming member (912) is slidably disposed within first stapling pathway (982) and unitarily attached to both stopping member (914), and latch (916). Stopping member (914) is slidably disposed within first stop channel (983). Bias member (918) biases camming member (912), stopping member (914) and latch (916) toward the position shown in FIG. 52A. As also seen in FIG. 52A, a proximal end of stopping member (914) is within connecting channel (988) while guide pin (428) is in the first proximal, pre-fired position (i.e. before firing outer staple driver (750)). The proximal end of stopping member (914) within connecting channel (988) may prevent guide pin (428) from accidentally over rotating into misalignment with first stapling pathway (982) prior to driving member (420) actuating outer staple driver (750) in accordance with the description above. Therefore, if a clinician accidentally attempts to proximally actuate driving member (920) such that guide pin (428) tries to cam against camming face (945), prior to driving member (420) actuating outer staple driver (750), guide pin (428) will be stopped by contacting the proximal end of stopping member (914).

Figure 52B:
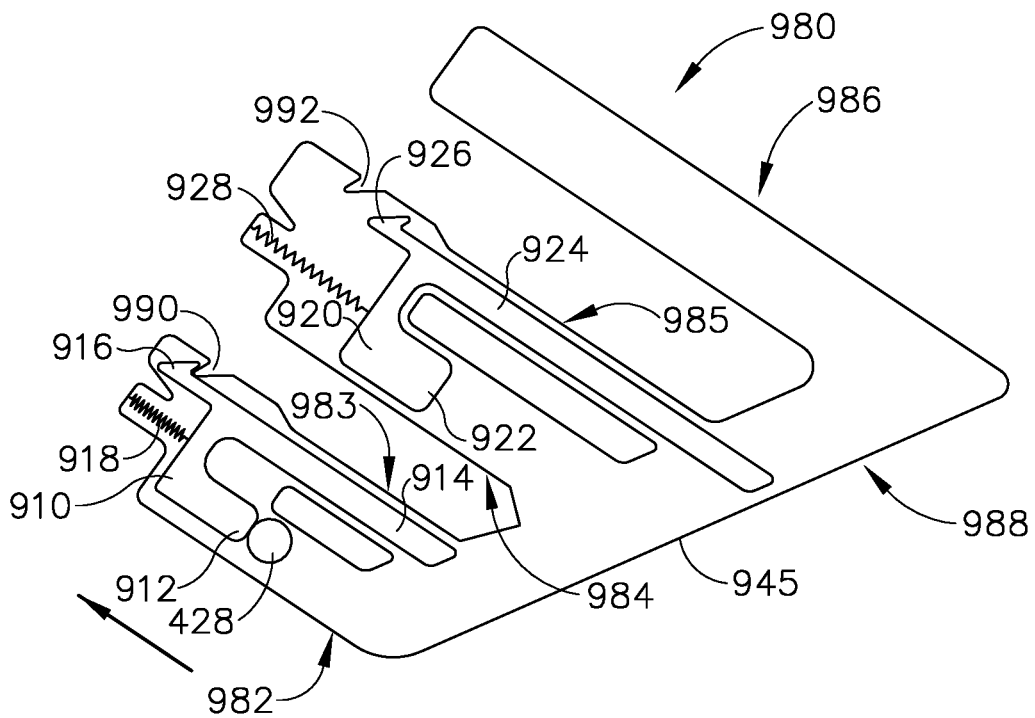
FIG. 52B depicts an elevational side view of a portion of the shaft assembly of FIG. 52A, with certain portions omitted for clarity, where the driving member of FIG. 50A is in the first rotational position aligned with the outer staple driver of FIG. 17, where the outer staple driver is in a fired position.

As seen in FIG. 52B, once driving member (420) suitably actuates outer staple driver (750), guide pin (428) drives against camming member (912) to distally drive camming member (912), stopping member (914), and latch (916). As this point, stopping member (914) slides within firs stop channel (983) such that the proximal end of stopping member (914) no longer obstructs connecting channel (988). Therefore, guide pin (428) may now rotate past stopping member (914) toward second stapling pathway (984). Additionally, latch (916) is actuated distally to interact with catch (990). Latch (916) interacts with catch (990) such that biasing member (918) may no longer bias the proximal end of stopping member (914) within connecting channel (918). Therefore, when guide pin (428) no longer abuts against camming member (912), camming member (912), stopping member (914), and latch (916) will remain in the distal position shown in FIG. 52B.

Figure 52C:
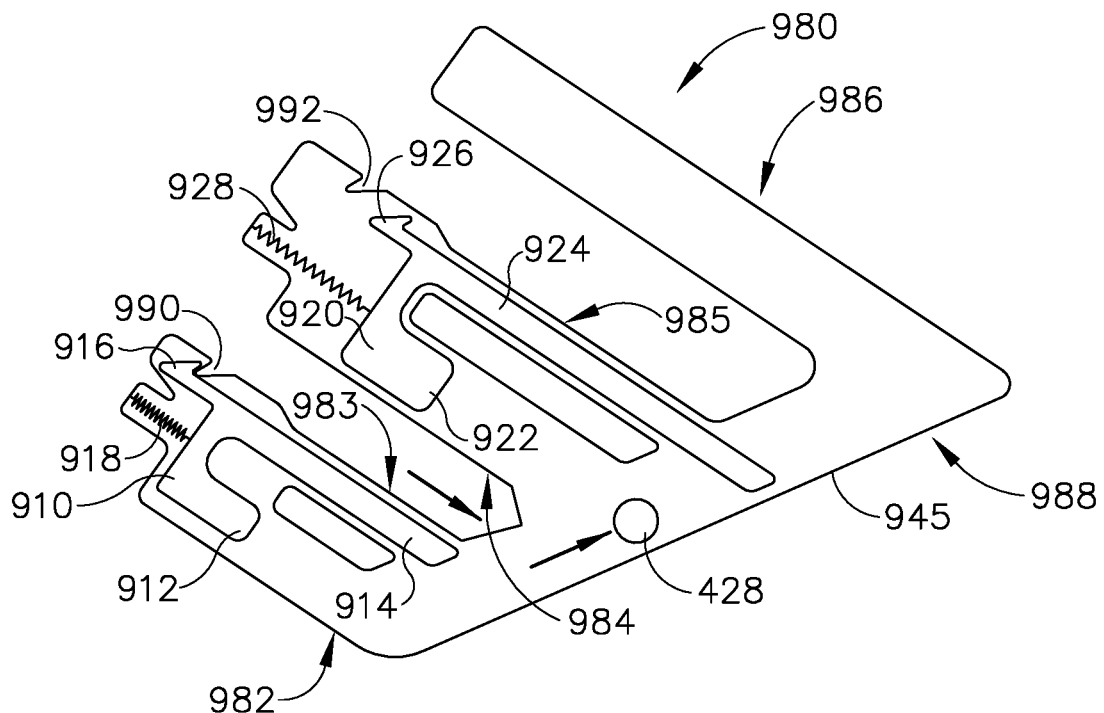
FIG. 52C depicts an elevational side view of a portion of the shaft assembly of FIG. 52A, with certain portions omitted for clarity, where the driving member of FIG. 50A is in a second rotational position aligned with the inner staple driver assembly of FIG. 18, where the inner staple driver assembly is in a pre-fired position.

Next, guide pin (428) may retract proximally, as shown in FIG. 52C, to cam against camming face (945) to rotate and align with second stapling pathway (984). Second stop member (920) includes a camming member (922), a stopping member (922), a latch (926), and a bias member (928). Camming member (922) is slidably disposed within second stapling pathway (984) and unitarily attached to both stopping member (924), and latch (926). Stopping member (924) is slidably disposed within second stop channel (985). Bias member (928) biases camming member (922), stopping member (924) and latch (926) toward the position shown in FIG. 52C. As also seen in FIG. 52C, a proximal end of stopping member (924) is within connecting channel (988) while guide pin (428) is in the second proximal, pre-fired position (i.e. before firing inner staple driver assembly (770)). The proximal end of stopping member (924) within connecting channel (988) may prevent guide pin (428) from accidentally over rotating into misalignment with second stapling pathway (984) prior to driving member (420) actuating inner staple driver assembly (770) in accordance with the description above. Therefore, if a clinician accidently attempts to proximally actuate driving member (920) such that guide pin (428) tries to cam against camming face (945), prior to driving member (420) actuating inner staple driver assembly (770), guide pin (428) will be stopped by contacting the proximal end of stopping member (924).

Figure 52D:
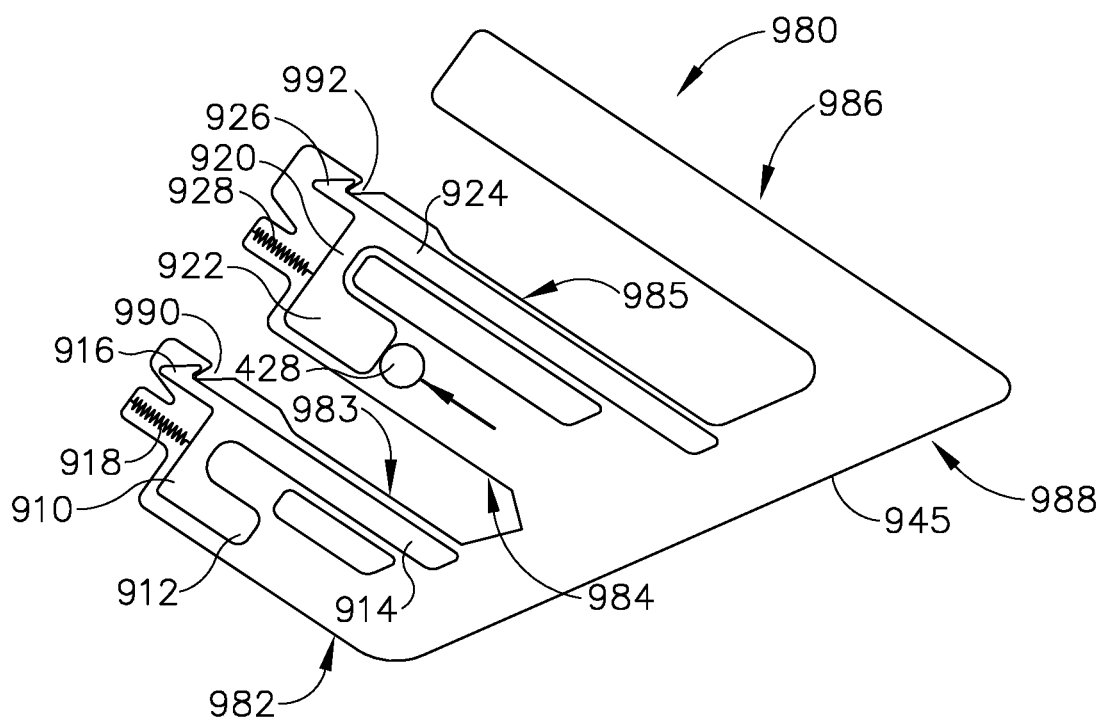
FIG. 52D depicts an elevational side view of a portion of the shaft assembly of FIG. 52A, with certain portions omitted for clarity, where the driving member of FIG. 50A is in the second rotational position aligned with the inner staple driver assembly of FIG. 18, where the inner staple driver assembly is in a fired position.

As seen in FIG. 52D, once driving member (420) suitably actuates inner staple driver assembly (770), guide pin (428) drives against camming member (922) to distally drive camming member (922), stopping member (924), and latch (926). As this point, stopping member (924) slides within second stop channel (985) such that the proximal end of stopping member (924) no longer obstructs connecting channel (988). Therefore, guide pin (428) may now rotate past stopping member (924) toward blade actuation pathway (986). Additionally, latch (926) is actuated distally to interact with catch (992). Latch (926) interacts with catch (992) such that biasing member (928) may no longer bias the proximal end of stopping member (924) within connecting channel (918). Therefore, when guide pin (428) no longer abuts against camming member (922), camming member (922), stopping member (924), and latch (926) will remain in the distal position shown in FIG. 52D.

Figure 52E:
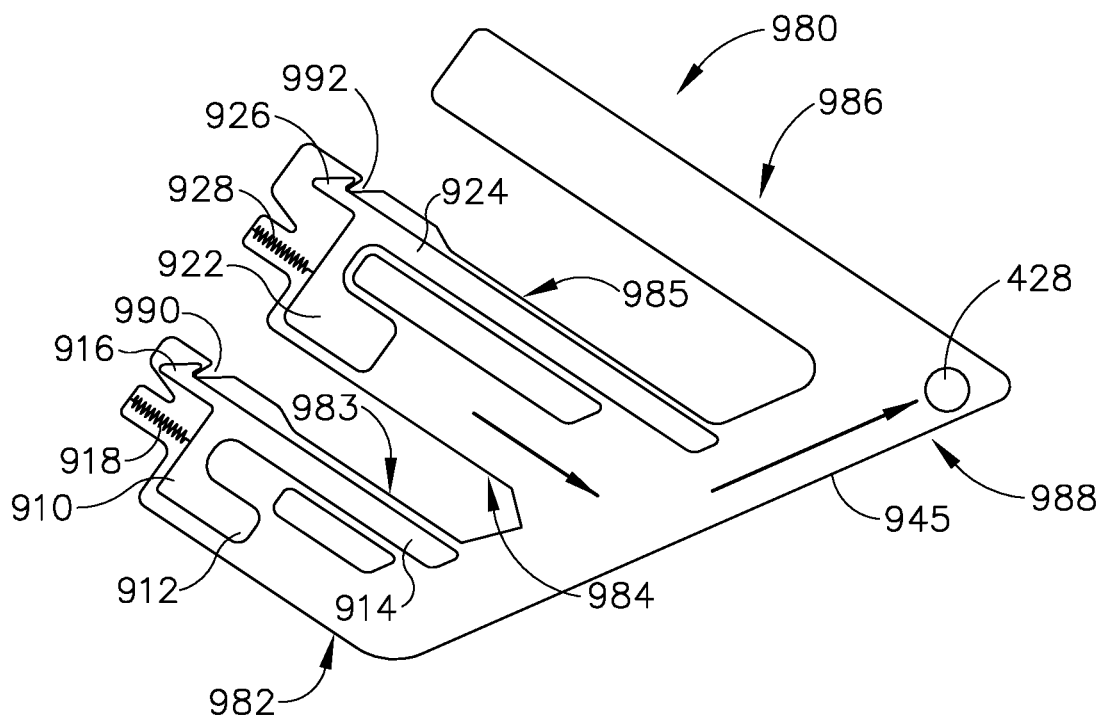
FIG. 52E depicts an elevational side view of a portion of the shaft assembly of FIG. 52A, with certain portions omitted for clarity, where the driving member of FIG. 50A is in a third rotational position aligned with the blade assembly of FIG. 20, where the blade assembly is in a pre-fired position.

Next, guide pin (428) may retract proximally, as shown in FIG. 52E, to cam against camming face (945) to rotate and align with blade actuation pathway (986). Driving member (420) may then actuate blade assembly (710) in accordance with the teachings above.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly, wherein the shaft assembly comprises: (i) an outer sheath, and (ii) a staple driving mechanism slidably housed within the outer sheath; (b) an end effector, wherein the end effector comprises: (i) a staple deck defining a plurality of staple openings in at least one annular array, wherein each staple opening in the plurality of staple openings houses a staple, (ii) an anvil configured to actuate relative to the staple deck to compress tissue between the staple deck and the anvil, (iii) a first staple driver, wherein the staple driving mechanism is configured to actuate the first staple driver to fire a first staple of the plurality of staples against the anvil, and (iv) a second staple driver, wherein the staple driving mechanism is configured to actuate the second staple driver independently of the first staple driver to fire a second staple of the plurality of staples against the anvil; and (c) an electrically powered drive assembly operable to actuate at least the first and second staple drivers.

Example 2

The apparatus of Example 1, wherein the end effector further comprise a blade assembly configured to sever tissue after the first staple driver is fired by the staple driving mechanism.

Example 3

The apparatus of any one or more of Examples 1 through 2, wherein the staple driving mechanism comprises: (i) a distally presented driver configured to actuate the first staple driver and the second staple driver, and (ii) an actuation member configured to actuate the distally presented driver, wherein the distally presented driver is rotatably coupled to the actuation member.

Example 4

The apparatus of Example 3, wherein the outer sheath defines a guide channel, wherein a first portion of the distally presented driver is disposed within the guide channel, wherein the distally presented driver is configured to rotate relative to the actuation member based on the longitudinal position of the actuation member within the guide channel.

Example 5

The apparatus of Example 4, wherein the guide channel comprises a first staple driving channel, a second staple driving channel, and a connecting channel in communication with both the first staple driving channel and the second staple driving channel.

Example 6

The apparatus of Example 5, wherein the connecting channel includes a camming surface configured to cam against the first portion of the distally present driver to rotate the distally presented driver relative to the actuation member.

Example 7

The apparatus of Example 6, wherein the first staple driver comprises a first firing leg configured to align with the distally presented driver while the first portion of the distally presented driver is disposed within the first staple driving channel of the guide channel.

Example 8

The apparatus of Example 7, wherein the second staple driver comprise a second firing leg configured to align with the distally presented driver while the first portion of the distally presented driver is disposed within the second staple driving channel of the guide channel.

Example 9

The apparatus of Example 8, wherein the end effector further comprises a blade assembly configure to sever tissue, wherein the blade assembly comprises a third firing leg, wherein the guide channel defines a blade driving channel in communication with the camming surface, wherein the third firing leg is configured to align with the distally presented driver while the first portion of the distally presented driver is disposed within the blade driving channel.

Example 10

The apparatus of any one or more of Examples 1 through 9, wherein the anvil comprises a first annular array of staple forming pockets and a second annular array of staple forming pockets, wherein the first staple driver is configured to fire the first staple against a first staple forming pocket of the first annular array of staple forming pockets, wherein the second staple driver is configured to fire the second staple against a second staple forming pocket of the second annular array of staple forming pockets.

Example 11

The apparatus of Example 1, wherein the shaft assembly further comprises a longitudinally reciprocating member, wherein the longitudinally reciprocating member is configured to (i) advance through a first distal stroke and thereby drive the first staple driver without driving the second staple driver, (ii) retract proximally after advancing through the first distal strike, and (iii) advance through a second distal stroke and thereby drive the second staple driver without driving the first staple driver.

Example 12

The apparatus of any one or more of Examples 1 through 11, where the shaft assembly further comprises a trocar assembly slidably housed within the shaft assembly, wherein the trocar assembly comprises a trocar configured to selectively couple with the anvil.

Example 13

The apparatus of Example 12, wherein the trocar assembly further comprises a longitudinal locking assembly configured to lock the trocar assembly relative to the shaft assembly.

Example 14

The apparatus of claim 12, further comprising a handle assembly configured to selectively couple with the shaft assembly.

Example 15

The apparatus of Example 14, wherein the electrically powered drive assembly is configured to actuate the trocar assembly and the staple driving mechanism.

Example 16

The apparatus of Example 15, wherein the shaft assembly comprises an intermediate firing shaft configured to couple the trocar assembly and the staple driving mechanism with the electrically powered drive assembly.

Example 17

The apparatus of Example 16, further comprising a clutch assembly, wherein the clutch assembly is configured to selectively disengage the trocar assembly with the intermediate firing shaft.

Example 18

An apparatus comprising: (a) a shaft assembly, wherein the shaft assembly comprises: (i) an outer sheath defining a longitudinal axis, (ii) a staple actuation assembly slidably housed within the outer sheath, wherein the staple actuation assembly is configured to rotate from a first angular position to a second angular position relative to the longitudinal axis, and (iii) a trocar assembly slidably housed within the outer sheath; (b) an end effector configured to drive a plurality staples into tissue, wherein the end effector comprises: (i) a staple deck defining a plurality of staple openings, wherein each staple opening in the plurality of staple opening houses a corresponding staple, (ii) an anvil configured to couple with the trocar assembly, wherein trocar assembly is configured to actuate the anvil toward the staple deck to compress tissue between the anvil and the staple deck, (iii) a first staple driver configured to drive a first corresponding staple through a first staple opening of the plurality of staple opening, wherein the staple actuation assembly is configured to translate within the outer sheath at the first angular position to drive the first staple driver, and (iv) a second staple driver configured to drive a second corresponding staple through a second staple opening of the plurality of staple opening, wherein the staple actuation assembly is configured to translate within the outer sheath at the second angular position to drive the second staple driver; and (c) an electrically powered drive assembly operable to actuate at least the first and second staple drivers.

Example 19

The apparatus of Example 18, wherein the outer sheath defines a guide channel configured to cam against the staple actuation assembly to rotate the staple actuation assembly form the first rotational position to the second rotational position.

Example 20

An apparatus, comprising: (a) a shaft assembly, wherein the shaft assembly comprises: (i) an outer sheath defining a guide channel, and (ii) a staple driving mechanism slidably housed within the outer sheath, wherein a placement pin of the staple driving mechanism is housed within the guide channel, wherein the staple driving mechanism is configured to rotate from a first rotational position to a second rotational position based on a location of the placement pin of the staple driving mechanism within the guide channel; (b) an end effector, wherein the end effector comprises: (i) a staple deck defining a plurality of staple openings, wherein each staple opening in the plurality of staple openings houses a staple, wherein the staple deck is fixed to the shaft assembly, (ii) an anvil configured to actuate relative to the staple deck to compress tissue between the staple deck and the anvil, and (iii) a first staple driver configured to actuate from a first pre-fired position to a first fired position, wherein the first staple driver is configured to fire a first staple through a first staple opening against the anvil in the fired position, wherein the staple driving mechanism is configured to longitudinally translate within the outer sheath to drive the first staple driver from the first pre-fired position to the first fired position in the first rotational position, and (iv) a second staple driver configured to actuate from a second pre-fired position to a second fired position, wherein the second staple drive is configured to fire a second staple through a second staple opening against the anvil in the first position, wherein the staple driving mechanism is configured longitudinally translate within the outer sheath to drive the second staple driver from the second pre-fired position to the second fired position in the second rotational position; and (c) an electrically powered drive assembly operable to actuate at least the first and second staple drivers.

IV. Miscellaneous

Any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, entitled "Apparatus and Method to Determine End of Life of Battery Powered Surgical Instrument," filed on Jun. 27, 2017, issued as U.S. Pat. No. 10,835,218 on Nov. 17, 2020, the disclosure of which is incorporated by reference herein. Various suitable ways in which the teachings herein may be combined with the teachings of U.S. patent application Ser. No. 15/634,385 filed on Jun. 27, 2017, issued as U.S. Pat. No. 10,835,218 on Nov. 17, 2020, will be apparent to those of ordinary skill in the art in view of the teachings herein.

In addition to the foregoing, the teachings herein may be readily combined with the teachings of U.S. patent application Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent application Ser. No. 15/634,418 filed on Jun. 27, 2017, issued as U.S. Pat. No. 10,163,309 on Dec. 25, 2018, will be apparent to those of ordinary skill in the art in view of the teachings herein.

In addition to the foregoing, the teachings herein may be readily combined with the teachings of U.S. patent application Ser. No. 15,634,436, entitled "Battery Pack with Integrated Circuit Providing Sleep Mode to Battery Pack and Associated Surgical Instrument," filed on Jun. 27 2017, issued as U.S. Pat. No. 10,639,018 on May 5, 2020, the disclosure of which is incorporated by reference herein. Various suitable ways in which the teachings herein may be combined with the teachings of U.S. patent application Ser. No. 15,634,436 filed on Jun. 27, 2017, issued as U.S. Pat. No. 10,639,018 on May 5, 2020, will be apparent to those of ordinary skill in the art in view of the teachings herein.

In addition to the foregoing, the teachings herein may be readily combined with the teachings of U.S. patent application Ser. No. 15/634,452, entitled "Battery Powered Surgical Instrument with Dual Power Utilization Circuits for Dual Modes," filed on Jun. 27, 2017, issued as U.S. Pat. No. 10,511,065 on Dec. 17, 2019, the disclosure of which is incorporated by reference herein. Various suitable ways in which the teachings herein may be combined with the teachings of U.S. patent application Ser. No. 15/634,452 filed on Jun. 27, 2017, issued as U.S. Pat. No. 10,511,065 on Dec. 17, 2019, will be apparent to those of ordinary skill in the art in view of the teachings herein.

In addition to the foregoing, the teachings herein may be readily combined with the teachings of U.S. patent application Ser. No. 15/634,475, entitled "Powered Surgical Instrument with Latching Feature Preventing Removal of Battery Pack," filed on Jun. 27, 2017, issued as U.S. Pat. No. 10,987,103 on Apr. 27, 2021, the disclosure of which is incorporated by reference herein. Various suitable ways in which the teachings herein may be combined with the teachings of U.S. patent application Ser. No. 15/634,475 filed on Jun. 27, 2017, issued as U.S. Pat. No. 10,987,103 on Apr. 27, 2021, will be apparent to those of ordinary skill in the art in view of the teachings herein.

In addition to the foregoing, the teachings herein may be readily combined with the teachings of U.S. patent application Ser. No. 15/634,497, entitled "Modular Powered Electrical Connection for Surgical Instrument with Features to Prevent Electrical Discharge" filed on Jun. 27, 2017, issued as U.S. Pat. No. 10,667,812 on Jun. 2, 2020, the disclosure of which is incorporated by reference herein. Various suitable ways in which the teachings herein may be combined with the teachings of U.S. patent application Ser. No. 15/634,497 filed on Jun. 27, 2017, issued as U.S. Pat. No. 10,677,812 on Jun. 2, 2020, will be apparent to those of ordinary skill in the art in view of the teachings herein.

In addition to the foregoing, the teachings herein may be readily combined with the teachings of U.S. patent application Ser. No. 15/634,524, entitled "Powered Surgical Instrument with Independent Selectively Applied Rotary and Linear Drivetrains," filed on Jun. 27, 2017, issued as U.S. Pat. No. 10,888,324 on Jan. 12, 2021, the disclosure of which is incorporated by reference herein. Various suitable ways in which the teachings herein may be combined with the teachings of U.S. patent application Ser. No. 15/634,524 filed on Jun. 27, 2017, issued as U.S. Pat. No. 10,888,324 on Jan. 12, 2021 will be apparent to those of ordinary skill in the art in view of the teachings herein.

In addition to the foregoing, the teachings herein may be readily combined with the teachings of U.S. patent application Ser. No. 15/634,620, entitled "Surgical Stapler with Independently Actuated Drivers to Provide Varying Staple Heights," filed on Jun. 27, 2017, issued as U.S. Pat. No. 10,828,029 on Nov. 10, 2020, the disclosure of which is incorporated by reference herein. Various suitable ways in which the teachings herein may be combined with the teachings of U.S. patent application Ser. No. 15/634,620 filed on Jun. 27, 2017, issued as U.S. Pat. No. 10,828,029 on Nov. 10, 2020, will be apparent to those of ordinary skill in the art in view of the teachings herein.

In addition to the foregoing, the teachings herein may be readily combined with the teachings of U.S. patent application Ser. No. 15/634,589, entitled "Surgical Instrument Handle Assembly with Feature to Clean Electrical Contacts at Modular Shaft Interface," filed on Jun. 27, 2017, issued as U.S. Pat. No. 10,090,616 on Oct. 2, 2018, the disclosure of which is incorporated by reference herein. Various suitable ways in which the teachings herein may be combined with the teachings of U.S. patent application Ser. No. 15/634,589 filed on Jun. 27, 2017, issued as U.S. Pat. No. 10,090,616 on Oct. 2, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) a shaft assembly, wherein the shaft assembly comprises:
 (i) an outer sheath, and
 (ii) a staple driving mechanism slidably housed within the outer sheath;
(b) an end effector, wherein the end effector comprises:
 (i) a staple deck defining a plurality of staple openings in at least one annular array, wherein each staple opening in the plurality of staple openings houses a staple,
 (ii) an anvil configured to actuate relative to the staple deck to compress tissue between the staple deck and the anvil,
 (iii) a first staple driver, wherein the staple driving mechanism is configured to actuate the first staple driver to fire a first staple of the plurality of staples against the anvil, and
 (iv) a second staple driver, wherein the staple driving mechanism is configured to actuate the second staple driver independently and relative to the first staple driver to fire a second staple of the plurality of staples against the anvil; and
(c) an electrically powered drive assembly operable to actuate at least the first and second staple drivers.

2. The apparatus of claim 1, wherein the end effector further comprises a blade assembly configured to sever tissue after the first staple driver is fired by the staple driving mechanism.

3. The apparatus of claim 1, wherein the staple driving mechanism comprises:
  (i) a distally presented driver configured to actuate the first staple driver and the second staple driver, and
  (ii) an actuation member configured to actuate the distally presented driver, wherein the distally presented driver is rotatably coupled to the actuation member.

4. The apparatus of claim 3, wherein the outer sheath defines a guide channel, wherein a first portion of the distally presented driver is disposed within the guide channel, wherein the distally presented driver is configured to rotate relative to the actuation member based on the longitudinal position of the actuation member within the guide channel.

5. The apparatus of claim 4, wherein the guide channel comprises a first staple driving channel, a second staple driving channel, and a connecting channel in communication with both the first staple driving channel and the second staple driving channel.

6. The apparatus of claim 5, wherein the connecting channel includes a camming surface configured to cam against the first portion of the distally present driver to rotate the distally presented driver relative to the actuation member.

7. The apparatus of claim 6, wherein the first staple driver comprises a first firing leg configured to align with the distally presented driver while the first portion of the distally presented driver is disposed within the first staple driving channel of the guide channel.

8. The apparatus of claim 7, wherein the second staple driver comprises a second firing leg configured to align with the distally presented driver while the first portion of the distally presented driver is disposed within the second staple driving channel of the guide channel.

9. The apparatus of claim 8, wherein the end effector further comprises a blade assembly configure to sever tissue, wherein the blade assembly comprises a third firing leg, wherein the guide channel defines a blade driving channel in communication with the camming surface, wherein the third firing leg is configured to align with the distally presented driver while the first portion of the distally presented driver is disposed within the blade driving channel.

10. The apparatus of claim 1, wherein the anvil comprises a first annular array of staple forming pockets and a second annular array of staple forming pockets, wherein the first staple driver is configured to fire the first staple against a first staple forming pocket of the first annular array of staple forming pockets, wherein the second staple driver is configured to fire the second staple against a second staple forming pocket of the second annular array of staple forming pockets.

11. The apparatus of claim 1, wherein the shaft assembly further comprises a longitudinally reciprocating member, wherein the longitudinally reciprocating member is configured to:
  (i) advance through a first distal stroke and thereby drive the first staple driver without driving the second staple driver,
  (ii) retract proximally after advancing through the first distal stroke, and
  (iii) advance through a second distal stroke and thereby drive the second staple driver without driving the first staple driver.

12. The apparatus of claim 1, where the shaft assembly further comprises a trocar assembly slidably housed within the shaft assembly, wherein the trocar assembly comprises a trocar configured to selectively couple with the anvil.

13. The apparatus of claim 12, wherein the trocar assembly further comprises a longitudinal locking assembly configured to lock the trocar assembly relative to the shaft assembly.

14. The apparatus of claim 12, further comprising a handle assembly configured to selectively couple with the shaft assembly.

15. The apparatus of claim 14, wherein the electrically powered drive assembly is configured to actuate the trocar assembly and the staple driving mechanism.

16. The apparatus of claim 15, wherein the shaft assembly comprises an intermediate firing shaft configured to couple the trocar assembly and the staple driving mechanism with the electrically powered drive assembly.

17. The apparatus of claim 16, further comprising a clutch assembly, wherein the clutch assembly is configured to selectively disengage the trocar assembly with the intermediate firing shaft.

18. An apparatus, comprising:
  (a) a shaft assembly; and
  (b) an end effector at a distal end of the shaft assembly, wherein the end effector comprises:
    (i) a staple deck defining a plurality of staple openings arranged in an annular array, wherein the staple openings are configured to house a plurality of staples,
    (ii) an anvil movable relative to the staple deck to compress tissue against the staple deck,
    (iii) a first staple driver, wherein the first staple driver is actuatable to fire a first staple of the plurality of staples toward the anvil, and
    (iv) a second staple driver, wherein the second staple driver is actuatable independently of the first staple driver to fire a second staple of the plurality of staples toward the anvil such that the second staple driver is configured to fire the second staple after the first staple has been fired.

19. The apparatus of claim 18, further comprising a motor operable to drive the first staple driver and the second staple driver.

20. An apparatus, comprising:
  (a) a shaft assembly comprising a reciprocating driver; and
  (b) an end effector at a distal end of the shaft assembly, wherein the end effector comprises:
    (i) a staple deck defining a plurality of staple openings, wherein the staple openings are configured to house a plurality of staples,
    (ii) an anvil movable relative to the staple deck to compress tissue against the staple deck,
    (iii) a first staple driver, wherein the first staple driver is actuatable to fire a first staple of the plurality of staples toward the anvil in response to a first firing stroke of the reciprocating driver,
    (iv) a second staple driver, wherein the second staple driver is actuatable independently of the first staple driver to fire a second staple of the plurality of staples toward the anvil in response to a second firing stroke to the reciprocating driver, and
    (v) a blade member, wherein the blade member is actuatable independently of the first staple driver and the second staple driver to cut tissue compressed between the anvil and the staple deck.

\* \* \* \* \*